(12) United States Patent
Peri et al.

(10) Patent No.: US 11,944,526 B2
(45) Date of Patent: Apr. 2, 2024

(54) ABSORBENT CORES HAVING MATERIAL FREE AREAS

(71) Applicant: The Procter & Gamble Company, Cincinnati, OH (US)

(72) Inventors: Andrea Andrew Peri, Kronberg (DE); Aniruddha Chatterjee, Kelkheim (DE); Peter Dziezok, Hochheim (DE); Bruno Johannes Ehrnsperger, Bad Soden (DE); Juliane Kamphus, Schwalbach (DE); Marion Lutsche, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 85 days.

(21) Appl. No.: 17/482,657

(22) Filed: Sep. 23, 2021

(65) Prior Publication Data
US 2022/0008264 A1   Jan. 13, 2022

Related U.S. Application Data

(63) Continuation of application No. 16/159,780, filed on Oct. 15, 2018, now Pat. No. 11,154,437, which is a
(Continued)

(30) Foreign Application Priority Data

Sep. 19, 2013  (EP) ..................................... 13185212
May 13, 2014  (EP) ..................................... 14168157

(51) Int. Cl.
*A61F 13/15*   (2006.01)
*A61F 13/532*  (2006.01)
(Continued)

(52) U.S. Cl.
CPC ........ *A61F 13/5323* (2013.01); *A61F 13/534* (2013.01); *A61F 13/535* (2013.01);
(Continued)

(58) Field of Classification Search
CPC .. A61F 13/5323; A61F 13/534; A61F 13/535; A61F 13/539; A61F 2013/53051;
(Continued)

(56) References Cited

U.S. PATENT DOCUMENTS 1,733,997 A   10/1929  Steven
1,734,499 A   11/1929  Davis
(Continued)

FOREIGN PATENT DOCUMENTS

CA    2001370    4/1990
CA    2291997    6/2000
(Continued)

OTHER PUBLICATIONS

"Super Absorbent Polymers Aqua Keep", Sumitomo Seika, May 31, 2012, 4 Pages.
(Continued)

*Primary Examiner* — Jacqueline F Stephens
(74) *Attorney, Agent, or Firm* — Daniel S. Albrecht; Sarah M. DeCristofaro

(57) ABSTRACT

An absorbent core, for use in an absorbent article, including a core wrap enclosing an absorbent material and including superabsorbent polymer particles. The core wrap includes a top side and a bottom side, and the absorbent core includes one or more area(s) substantially free of absorbent material through which the top side of the core wrap is attached to the bottom side of the core wrap, so that when the absorbent material swells the core wrap forms one or more channel(s) along the area(s) substantially free of absorbent material. The superabsorbent polymer particles have a time to reach
(Continued)

an uptake of 20 g/g (T20) of less than 240 s as measured according to the K(t) test method.

20 Claims, 9 Drawing Sheets

Related U.S. Application Data continuation of application No. 14/462,621, filed on Aug. 19, 2014, now Pat. No. 10,130,527.

(51) Int. Cl.

| | | |
|---|---|---|
| *A61F 13/534* | (2006.01) | |
| *A61F 13/535* | (2006.01) | |
| *A61F 13/539* | (2006.01) | |
| *A61L 15/42* | (2006.01) | |
| *A61L 15/58* | (2006.01) | |
| *A61L 15/60* | (2006.01) | |
| *C08F 120/06* | (2006.01) | |
| *C08F 220/06* | (2006.01) | |
| *C08J 3/24* | (2006.01) | |
| *C08L 33/02* | (2006.01) | |
| *A61F 13/53* | (2006.01) | |

(52) U.S. Cl.
CPC ............ *A61F 13/539* (2013.01); *A61L 15/42* (2013.01); *A61L 15/58* (2013.01); *A61L 15/60* (2013.01); *C08F 120/06* (2013.01); *C08F 220/06* (2013.01); *C08J 3/245* (2013.01); *C08L 33/02* (2013.01); *A61F 2013/530481* (2013.01); *A61F 2013/53051* (2013.01); *A61F 2013/530715* (2013.01); *A61F 2013/53472* (2013.01); *C08J 2333/02* (2013.01)

(58) Field of Classification Search
CPC .......... A61F 2013/530715; A61F 2013/53472; A61L 15/58; A61L 15/60; A61L 15/42; C08F 120/06; C08F 220/06; C08J 3/245
See application file for complete search history.

(56) References Cited

U.S. PATENT DOCUMENTS

| | | |
|---|---|---|
| 1,989,283 A | 1/1935 | Limacher |
| 2,058,509 A | 10/1936 | David |
| 2,271,676 A | 2/1942 | Elna |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Rose |
| 2,570,963 A | 10/1951 | Mesmer |
| 2,583,553 A | 1/1952 | Faure |
| 2,705,957 A | 4/1955 | Virginia |
| 2,788,003 A | 4/1957 | Norden |
| 2,788,786 A | 4/1957 | Dexter |
| 2,798,489 A | 7/1957 | Mayes |
| 2,807,263 A | 9/1957 | Mae |
| 2,830,589 A | 4/1958 | Doner |
| 2,890,700 A | 6/1959 | Lonberg-holm |
| 2,890,701 A | 6/1959 | Mary |
| 2,898,912 A | 8/1959 | Jane |
| 2,931,361 A | 4/1960 | Alice |
| 2,977,957 A | 4/1961 | Joseph |
| 3,071,138 A | 1/1963 | Gustavo |
| 3,180,335 A | 4/1965 | Duncan et al. |
| 3,207,158 A | 9/1965 | Kazuko et al. |
| 3,227,160 A | 1/1966 | Margaret |
| 3,386,442 A | 6/1968 | Reinhardt |
| 3,411,504 A | 11/1968 | Glassman |
| 3,561,446 A | 2/1971 | Jones, Sr. |
| 3,572,342 A | 3/1971 | Lindquist |
| 3,572,432 A | 3/1971 | Aulick |
| 3,575,174 A | 4/1971 | Mogor |
| 3,578,155 A | 5/1971 | Small et al. |
| 3,606,887 A | 9/1971 | Roeder |
| 3,610,244 A | 10/1971 | Jones, Sr. |
| 3,618,608 A | 11/1971 | Brink |
| 3,642,001 A | 2/1972 | Sabee |
| 3,653,381 A | 4/1972 | Warnken |
| 3,670,731 A | 6/1972 | Harmon |
| 3,688,767 A | 9/1972 | Goldstein |
| 3,710,797 A | 1/1973 | Marsan |
| 3,731,688 A | 5/1973 | Litt et al. |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand |
| 3,828,784 A | 8/1974 | Zoephel |
| 3,840,418 A | 10/1974 | Sabee |
| 3,847,702 A | 11/1974 | Jones |
| 3,848,594 A | 11/1974 | Buell |
| 3,848,595 A | 11/1974 | Endres |
| 3,848,597 A | 11/1974 | Endres |
| 3,860,003 A | 1/1975 | Buell |
| 3,863,637 A | 2/1975 | Macdonald et al. |
| 3,882,870 A | 5/1975 | Hathaway |
| 3,884,234 A | 5/1975 | Taylor |
| 3,900,032 A | 8/1975 | Heurlen |
| 3,911,173 A | 10/1975 | Sprague, Jr. |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,055,180 A | 10/1977 | Karami |
| 4,074,508 A | 2/1978 | Reid |
| 4,079,739 A | 3/1978 | Whitehead |
| 4,084,592 A | 4/1978 | Tritsch |
| 4,100,922 A | 7/1978 | Hernandez |
| 4,232,674 A | 11/1980 | Melican |
| 4,257,418 A | 3/1981 | Hessner |
| 4,259,220 A | 3/1981 | Bunnelle et al. |
| 4,287,153 A | 9/1981 | Towsend |
| 4,296,750 A | 10/1981 | Woon et al. |
| 4,315,508 A | 2/1982 | Bolick |
| 4,324,246 A | 4/1982 | Mullane et al. |
| 4,340,706 A | 7/1982 | Obayashi et al. |
| 4,341,216 A | 7/1982 | Obenour |
| 4,342,314 A | 8/1982 | Radel et al. |
| 4,360,021 A | 11/1982 | Stima |
| 4,381,783 A | 5/1983 | Elias |
| 4,388,075 A | 6/1983 | Mesek et al. |
| 4,410,571 A | 10/1983 | Korpman |
| 4,461,621 A | 7/1984 | Karami et al. |
| 4,463,045 A | 7/1984 | Ahr |
| 4,469,710 A | 9/1984 | Rielley et al. |
| 4,475,912 A | 10/1984 | Coates |
| 4,490,148 A | 12/1984 | Beckestrom |
| 4,507,438 A | 3/1985 | Obayashi et al. |
| 4,515,595 A | 5/1985 | Kievit |
| 4,527,990 A | 7/1985 | Sigl |
| 4,541,871 A | 9/1985 | Obayashi et al. |
| 4,551,191 A | 11/1985 | Kock et al. |
| 4,573,986 A | 3/1986 | Minetola |
| 4,578,072 A | 3/1986 | Lancaster |
| 4,578,702 A | 3/1986 | Campbell, III |
| 4,585,448 A | 4/1986 | Enloe |
| 4,585,450 A | 4/1986 | Rosch et al. |
| 4,589,878 A | 5/1986 | Mitrani |

(56) References Cited

U.S. PATENT DOCUMENTS

| | | |
|---|---|---|
| 4,596,568 A | 6/1986 | Flug |
| 4,601,717 A | 7/1986 | Blevins |
| 4,606,964 A | 8/1986 | Wideman |
| 4,609,518 A | 9/1986 | Curro et al. |
| 4,610,678 A | 9/1986 | Weisman |
| 4,623,342 A | 11/1986 | Ito et al. |
| 4,624,666 A | 11/1986 | Derossett et al. |
| 4,629,643 A | 12/1986 | Curro |
| 4,636,207 A | 1/1987 | Buell |
| 4,641,381 A | 2/1987 | Heran et al. |
| 4,646,510 A | 3/1987 | Mcintyre |
| 4,662,875 A | 5/1987 | Hirotsu |
| 4,666,983 A | 5/1987 | Tsubakimoto et al. |
| 4,670,011 A | 6/1987 | Mesek |
| 4,670,012 A | 6/1987 | Johnson |
| 4,680,030 A | 7/1987 | Coates et al. |
| 4,681,579 A | 7/1987 | Toussant et al. |
| 4,681,581 A | 7/1987 | Coates |
| 4,681,793 A | 7/1987 | Linman et al. |
| 4,690,680 A | 9/1987 | Higgins |
| 4,695,278 A | 9/1987 | Lawson |
| 4,699,622 A | 10/1987 | Toussant |
| 4,704,115 A | 11/1987 | Buell |
| 4,704,116 A | 11/1987 | Enloe |
| 4,710,189 A | 12/1987 | Lash |
| 4,720,321 A | 1/1988 | Smith |
| 4,731,066 A | 3/1988 | Korpman |
| 4,731,070 A | 3/1988 | Koci |
| RE32,649 E | 4/1988 | Brandt et al. |
| 4,741,941 A | 5/1988 | Englebert |
| 4,747,846 A | 5/1988 | Boland et al. |
| 4,753,648 A | 6/1988 | Jackson |
| 4,773,905 A | 9/1988 | Molee et al. |
| 4,784,892 A | 11/1988 | Storey et al. |
| 4,785,996 A | 11/1988 | Ziecker |
| 4,787,896 A | 11/1988 | Houghton et al. |
| 4,795,454 A | 1/1989 | Dragoo |
| 4,800,102 A | 1/1989 | Takada |
| 4,802,884 A | 2/1989 | Froeidh |
| 4,806,408 A | 2/1989 | Pierre et al. |
| 4,806,598 A | 2/1989 | Morman |
| 4,808,176 A | 2/1989 | Kielpikowski |
| 4,808,178 A | 2/1989 | Aziz |
| 4,826,880 A | 5/1989 | Lesniak |
| 4,834,735 A | 5/1989 | Alemany |
| 4,834,740 A | 5/1989 | Suzuki et al. |
| 4,834,742 A | 5/1989 | Wilson et al. |
| 4,838,886 A | 6/1989 | Kent |
| 4,842,666 A | 6/1989 | Werenicz |
| 4,846,815 A | 7/1989 | Scripps |
| 4,846,825 A | 7/1989 | Enloe et al. |
| 4,848,815 A | 7/1989 | Molloy |
| 4,861,652 A | 8/1989 | Lippert et al. |
| 4,869,724 A | 9/1989 | Scripps |
| 4,886,697 A | 12/1989 | Perdelwitz, Jr. et al. |
| 4,888,231 A | 12/1989 | Angstadt |
| 4,892,528 A | 1/1990 | Suzuki |
| 4,892,535 A | 1/1990 | Bjoernberg et al. |
| 4,892,536 A | 1/1990 | Desmarais |
| 4,894,060 A | 1/1990 | Nestegard |
| 4,894,277 A | 1/1990 | Akasaki |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz |
| 4,936,839 A | 6/1990 | Molee et al. |
| 4,940,463 A | 7/1990 | Leathers et al. |
| 4,940,464 A | 7/1990 | Van |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson |
| 4,966,809 A | 10/1990 | Tanaka et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen |
| 5,071,414 A | 12/1991 | Elliott |
| 5,072,687 A | 12/1991 | Mitchell et al. |
| 5,085,654 A | 2/1992 | Buell |
| 5,087,255 A | 2/1992 | Sims |
| 5,092,861 A | 3/1992 | Nomura |
| 5,102,597 A | 4/1992 | Berg et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron |
| D329,697 S | 9/1992 | Fahrenkrug et al. |
| 5,143,679 A | 9/1992 | Weber |
| 5,147,343 A | 9/1992 | Kellenberger |
| 5,147,345 A | 9/1992 | Lavon |
| 5,149,334 A | 9/1992 | Berg et al. |
| 5,149,335 A | 9/1992 | Kellenberger |
| 5,151,091 A | 9/1992 | Glaug et al. |
| 5,151,092 A | 9/1992 | Buell |
| 5,156,793 A | 10/1992 | Buell |
| 5,167,653 A | 12/1992 | Igaue et al. |
| 5,167,897 A | 12/1992 | Weber |
| 5,175,046 A | 12/1992 | Nguyen |
| 5,180,622 A | 1/1993 | Lahrman et al. |
| 5,188,624 A | 2/1993 | Brunnenkant et al. |
| 5,190,563 A | 3/1993 | Herron et al. |
| 5,190,606 A | 3/1993 | Merkatoris et al. |
| 5,204,997 A | 4/1993 | Suzuki et al. |
| 5,213,817 A | 5/1993 | Pelley |
| 5,221,274 A | 6/1993 | Buell |
| 5,235,515 A | 8/1993 | Ungpiyakul et al. |
| 5,242,436 A | 9/1993 | Weil |
| 5,246,431 A | 9/1993 | Minetola et al. |
| 5,246,432 A | 9/1993 | Suzuki et al. |
| 5,246,433 A | 9/1993 | Hasse |
| 5,248,309 A | 9/1993 | Serbiak |
| 5,260,345 A | 11/1993 | Desmarais |
| 5,269,775 A | 12/1993 | Freeland |
| 5,281,683 A | 1/1994 | Yano et al. |
| H1298 H | 4/1994 | Ahr et al. |
| 5,300,565 A | 4/1994 | Berg |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | Lavon et al. |
| 5,366,782 A | 11/1994 | Curro et al. |
| 5,382,610 A | 1/1995 | Harada et al. |
| 5,387,207 A | 2/1995 | Dyer |
| 5,387,208 A | 2/1995 | Ashton |
| 5,387,209 A | 2/1995 | Yamamoto et al. |
| 5,389,095 A | 2/1995 | Suzuki et al. |
| 5,397,316 A | 3/1995 | Young |
| 5,397,317 A | 3/1995 | Thomas |
| 5,399,175 A | 3/1995 | Glaug et al. |
| 5,401,792 A | 3/1995 | Gaddam et al. |
| 5,409,771 A | 4/1995 | Dahmen et al. |
| H1440 H | 5/1995 | New et al. |
| 5,411,497 A | 5/1995 | Tanzer |
| 5,415,644 A | 5/1995 | Enloe |
| 5,425,725 A | 6/1995 | Tanzer |
| 5,429,630 A | 7/1995 | Beal et al. |
| 5,433,715 A | 7/1995 | Tanzer |
| 5,451,219 A | 9/1995 | Suzuki et al. |
| 5,451,442 A | 9/1995 | Pieniak et al. |
| 5,460,622 A | 10/1995 | Dragoo et al. |
| 5,460,623 A | 10/1995 | Emenaker et al. |
| 5,462,541 A | 10/1995 | Bruemmer et al. |
| 5,476,458 A | 12/1995 | Glaug et al. |
| 5,486,166 A | 1/1996 | Bishop et al. |
| 5,486,167 A | 1/1996 | Dragoo et al. |

(56) References Cited

U.S. PATENT DOCUMENTS

| | | |
|---|---|---|
| 5,487,736 A | 1/1996 | Van |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell |
| 5,507,736 A | 4/1996 | Clear |
| 5,507,895 A | 4/1996 | Suekane |
| 5,509,915 A | 4/1996 | Hanson |
| 5,514,104 A | 5/1996 | Cole et al. |
| 5,518,801 A | 5/1996 | Chappell |
| 5,520,674 A | 5/1996 | Lavon et al. |
| 5,522,810 A | 6/1996 | Allen, Jr. et al. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe |
| 5,559,335 A | 9/1996 | Zeng et al. |
| 5,560,878 A | 10/1996 | Dragoo et al. |
| 5,562,634 A | 10/1996 | Flumene et al. |
| 5,562,646 A | 10/1996 | Goldman |
| 5,569,234 A | 10/1996 | Buell |
| 5,571,096 A | 11/1996 | Dobrin |
| 5,574,121 A | 11/1996 | Irie et al. |
| 5,575,783 A | 11/1996 | Clear |
| 5,580,411 A | 12/1996 | Nease |
| 5,584,829 A | 12/1996 | Lavash et al. |
| 5,586,979 A | 12/1996 | Thomas |
| 5,591,152 A | 1/1997 | Buell |
| 5,591,155 A | 1/1997 | Nishikawa |
| 5,593,399 A | 1/1997 | Tanzer |
| 5,599,335 A | 2/1997 | Goldman |
| 5,601,542 A | 2/1997 | Melius |
| 5,607,414 A | 3/1997 | Richards |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,609,588 A | 3/1997 | Dipalma et al. |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur et al. |
| 5,624,424 A | 4/1997 | Saisaka et al. |
| 5,625,222 A | 4/1997 | Yoneda |
| 5,626,571 A | 5/1997 | Young et al. |
| 5,628,741 A | 5/1997 | Buell et al. |
| 5,628,845 A | 5/1997 | Murray et al. |
| 5,635,191 A | 6/1997 | Roe |
| 5,635,271 A | 6/1997 | Zafiroglu |
| 5,637,106 A | 6/1997 | Mitchell et al. |
| 5,643,238 A | 7/1997 | Baker |
| 5,643,243 A | 7/1997 | Klemp |
| 5,643,588 A | 7/1997 | Roe |
| 5,649,914 A | 7/1997 | Glaug et al. |
| 5,650,214 A | 7/1997 | Anderson et al. |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,662,758 A | 9/1997 | Hamilton et al. |
| 5,669,894 A | 9/1997 | Goldman |
| 5,674,215 A | 10/1997 | Roennberg |
| 5,681,300 A | 10/1997 | Ahr |
| 5,683,374 A | 11/1997 | Yamamoto et al. |
| 5,685,874 A | 11/1997 | Buell et al. |
| 5,690,624 A | 11/1997 | Sasaki et al. |
| 5,690,627 A | 11/1997 | Clear et al. |
| 5,691,035 A | 11/1997 | Chappell et al. |
| 5,691,036 A | 11/1997 | Lin et al. |
| 5,695,488 A | 12/1997 | Sosalla |
| 5,700,254 A | 12/1997 | Mcdowall |
| 5,702,376 A | 12/1997 | Glaug et al. |
| 5,713,881 A | 2/1998 | Rezai et al. |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | Mcfall |
| H1732 H | 6/1998 | Jhonson |
| 5,762,641 A | 6/1998 | Bewick-sonntag |
| 5,766,388 A | 6/1998 | Pelley et al. |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani et al. |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka et al. |
| 5,830,202 A | 11/1998 | Bogdanski et al. |
| 5,833,678 A | 11/1998 | Ashton et al. |
| 5,837,789 A | 11/1998 | Stockhausen et al. |
| 5,840,404 A | 11/1998 | Graff |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mizutani |
| 5,855,572 A | 1/1999 | Schmidt |
| 5,858,013 A | 1/1999 | Kling |
| 5,858,515 A | 1/1999 | Stokes et al. |
| 5,865,823 A | 2/1999 | Curro |
| 5,865,824 A | 2/1999 | Chen et al. |
| 5,873,868 A | 2/1999 | Nakahata |
| 5,876,391 A | 3/1999 | Roe et al. |
| 5,879,751 A | 3/1999 | Bogdanski |
| 5,891,118 A | 4/1999 | Toyoshima et al. |
| 5,891,544 A | 4/1999 | Chappell et al. |
| 5,897,545 A | 4/1999 | Kline |
| 5,904,673 A | 5/1999 | Roe et al. |
| 5,925,439 A | 7/1999 | Haubach |
| 5,928,184 A | 7/1999 | Etheredge et al. |
| 5,931,825 A | 8/1999 | Kuen et al. |
| 5,938,648 A | 8/1999 | Beck |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline |
| 5,964,743 A | 10/1999 | Abuto et al. |
| 5,968,025 A | 10/1999 | Roe |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles |
| 6,010,490 A | 1/2000 | Freeland et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,056,732 A | 5/2000 | Fujioka et al. |
| 6,060,115 A | 5/2000 | Borowski et al. |
| 6,068,620 A | 5/2000 | Chmielewski |
| 6,080,909 A | 6/2000 | Oesterdahl et al. |
| 6,083,210 A | 7/2000 | Young et al. |
| 6,090,994 A | 7/2000 | Chen |
| 6,091,336 A | 7/2000 | Zand et al. |
| 6,093,474 A | 7/2000 | Sironi |

(56) References Cited

U.S. PATENT DOCUMENTS

| | | |
|---|---|---|
| 6,099,515 A | 8/2000 | Sugito |
| 6,102,892 A | 8/2000 | Putzer et al. |
| 6,103,814 A | 8/2000 | Vandrongelen et al. |
| 6,107,537 A | 8/2000 | Elder |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak et al. |
| 6,143,821 A | 11/2000 | Houben |
| 6,152,908 A | 11/2000 | Widlund et al. |
| 6,156,023 A | 12/2000 | Yoshioka |
| 6,156,424 A | 12/2000 | Taylor |
| 6,160,197 A | 12/2000 | Lassen et al. |
| 6,165,160 A | 12/2000 | Suzuki |
| 6,174,302 B1 | 1/2001 | Kumasaka |
| 6,177,606 B1 | 1/2001 | Etheredge et al. |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Roennberg |
| 6,254,294 B1 | 7/2001 | Muhar |
| 6,258,996 B1 | 7/2001 | Goldman |
| 6,261,679 B1 | 7/2001 | Chen et al. |
| 6,264,639 B1 | 7/2001 | Sauer |
| 6,265,488 B1 | 7/2001 | Nagasuna et al. |
| 6,290,686 B1 | 9/2001 | Tanzer |
| 6,306,122 B1 | 10/2001 | Narawa et al. |
| 6,307,119 B1 | 10/2001 | Cammarota |
| 6,315,765 B1 | 11/2001 | Datta et al. |
| 6,319,239 B1 | 11/2001 | Daniels |
| 6,322,552 B1 | 11/2001 | Blenke et al. |
| 6,325,787 B1 | 12/2001 | Roe et al. |
| 6,326,525 B1 | 12/2001 | Hamajima et al. |
| 6,330,735 B1 | 12/2001 | Hahn et al. |
| 6,334,858 B1 | 1/2002 | Ronnberg et al. |
| 6,336,922 B1 | 1/2002 | Vangompel et al. |
| 6,340,611 B1 | 1/2002 | Shimizu et al. |
| 6,342,715 B1 | 1/2002 | Shimizu et al. |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin |
| 6,383,960 B1 | 5/2002 | Everett et al. |
| 6,394,989 B2 | 5/2002 | Mizutani |
| 6,402,729 B1 | 6/2002 | Boberg et al. |
| 6,402,731 B1 | 6/2002 | Suprise et al. |
| 6,403,857 B1 | 6/2002 | Gross et al. |
| 6,406,467 B1 | 6/2002 | Dilnik et al. |
| 6,409,883 B1 | 6/2002 | Makolin |
| 6,410,820 B1 | 6/2002 | Mcfall et al. |
| 6,410,822 B1 | 6/2002 | Mizutani |
| 6,413,248 B1 | 7/2002 | Mizutani |
| 6,413,249 B1 | 7/2002 | Turi et al. |
| 6,414,214 B1 | 7/2002 | Engelhardt et al. |
| 6,416,502 B1 | 7/2002 | Connelly et al. |
| 6,416,697 B1 | 7/2002 | Venturino et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline |
| 6,432,099 B2 | 8/2002 | Roennberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 | 10/2002 | Rosenfeld et al. |
| 6,461,034 B1 | 10/2002 | Cleveland |
| 6,461,342 B2 | 10/2002 | Tanji et al. |
| 6,461,343 B1 | 10/2002 | Schaefer et al. |
| 6,472,478 B1 | 10/2002 | Funk |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |
| 6,503,979 B1 | 1/2003 | Funk et al. |
| 6,506,186 B1 | 1/2003 | Roessler et al. |
| 6,506,961 B1 | 1/2003 | Levy |
| 6,515,195 B1 | 2/2003 | Lariviere et al. |
| 6,517,525 B1 | 2/2003 | Berthou et al. |
| 6,518,479 B1 | 2/2003 | Graef et al. |
| 6,520,947 B1 | 2/2003 | Tilly et al. |
| 6,521,811 B1 | 2/2003 | Lassen et al. |
| 6,521,812 B1 | 2/2003 | Graef et al. |
| 6,524,294 B1 | 2/2003 | Hilston et al. |
| 6,525,240 B1 | 2/2003 | Graef et al. |
| 6,528,698 B2 | 3/2003 | Mizutani et al. |
| 6,529,860 B1 | 3/2003 | Strumolo et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer et al. |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld et al. |
| 6,585,713 B1 | 7/2003 | Lemahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef et al. |
| 6,632,209 B1 | 10/2003 | Chmielewski |
| 6,632,504 B1 | 10/2003 | Gillespie |
| 6,645,569 B2 | 11/2003 | Cramer |
| 6,646,180 B1 | 11/2003 | Chmielewski |
| 6,648,869 B1 | 11/2003 | Gillies et al. |
| 6,648,870 B1 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya et al. |
| 6,667,424 B1 | 12/2003 | Hamilton |
| 6,670,522 B1 | 12/2003 | Graef et al. |
| 6,673,982 B1 | 1/2004 | Chen |
| 6,673,983 B1 | 1/2004 | Graef et al. |
| 6,673,985 B2 | 1/2004 | Mizutani et al. |
| 6,682,515 B1 | 1/2004 | Mizutani et al. |
| 6,682,516 B2 | 1/2004 | Johnston et al. |
| 6,689,115 B1 | 2/2004 | Coenen et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen et al. |
| 6,705,465 B2 | 3/2004 | Ling et al. |
| 6,706,129 B2 | 3/2004 | Ando et al. |
| 6,706,943 B2 | 3/2004 | Onishi et al. |
| 6,710,224 B2 | 3/2004 | Chmielewski et al. |
| 6,710,225 B1 | 3/2004 | Everett et al. |

(56) References Cited

U.S. PATENT DOCUMENTS

| | | |
|---|---|---|
| 6,716,205 B2 | 4/2004 | Coenen et al. |
| 6,716,441 B1 | 4/2004 | Osborne et al. |
| 6,717,029 B2 | 4/2004 | Baker |
| 6,726,668 B2 | 4/2004 | Underhill et al. |
| 6,726,792 B1 | 4/2004 | Johnson et al. |
| 6,730,387 B2 | 5/2004 | Rezai et al. |
| 6,734,335 B1 | 5/2004 | Graef et al. |
| 6,746,976 B1 | 6/2004 | Urankar et al. |
| 6,790,798 B1 | 9/2004 | Suzuki |
| 6,802,834 B2 | 10/2004 | Melius et al. |
| 6,809,158 B2 | 10/2004 | Ikeuchi et al. |
| 6,811,642 B2 | 11/2004 | Ochi |
| 6,818,083 B2 | 11/2004 | Mcamish et al. |
| 6,818,166 B2 | 11/2004 | Edwardson et al. |
| 6,830,800 B2 | 12/2004 | Curro et al. |
| 6,832,905 B2 | 12/2004 | Delzer et al. |
| 6,840,929 B2 | 1/2005 | Kurata |
| 6,846,374 B2 | 1/2005 | Coenen et al. |
| 6,858,771 B2 | 2/2005 | Yoshimasa et al. |
| 6,863,933 B2 | 3/2005 | Cramer |
| 6,863,960 B2 | 3/2005 | Curro et al. |
| 6,867,345 B2 | 3/2005 | Shimoe et al. |
| 6,867,346 B1 | 3/2005 | Dopps et al. |
| 6,878,433 B2 | 4/2005 | Curro |
| 6,878,647 B1 | 4/2005 | Rezai |
| 6,880,211 B2 | 4/2005 | Jackson et al. |
| 6,891,080 B2 | 5/2005 | Minato et al. |
| 6,904,865 B2 | 6/2005 | Klofta et al. |
| 6,911,574 B1 | 6/2005 | Mizutani |
| 6,923,797 B2 | 8/2005 | Shinohara et al. |
| 6,923,926 B2 | 8/2005 | Walter et al. |
| 6,926,703 B2 | 8/2005 | Sugito et al. |
| 6,929,629 B2 | 8/2005 | Drevik et al. |
| 6,939,914 B2 | 9/2005 | Qin et al. |
| 6,946,585 B2 | 9/2005 | London |
| 6,953,451 B2 | 10/2005 | Berba et al. |
| 6,955,733 B2 | 10/2005 | Miller |
| 6,962,578 B1 | 11/2005 | Lavon |
| 6,962,645 B2 | 11/2005 | Graef et al. |
| 6,965,058 B1 | 11/2005 | Raidel |
| 6,969,781 B2 | 11/2005 | Graef et al. |
| 6,972,010 B2 | 12/2005 | Pesce et al. |
| 6,972,011 B2 | 12/2005 | Mori |
| 6,979,564 B2 | 12/2005 | Glucksmann et al. |
| 6,982,052 B2 | 1/2006 | Daniels et al. |
| 7,001,167 B2 | 2/2006 | Venturino et al. |
| 7,014,632 B2 | 3/2006 | Takino et al. |
| 7,015,370 B2 | 3/2006 | Watanabe et al. |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita et al. |
| 7,067,711 B2 | 6/2006 | Kuroda et al. |
| 7,073,373 B2 | 7/2006 | La |
| 7,078,583 B2 | 7/2006 | Kudo et al. |
| 7,090,665 B2 | 8/2006 | Ohashi et al. |
| 7,108,759 B2 | 9/2006 | You et al. |
| 7,108,916 B2 | 9/2006 | Ehrnsperger |
| 7,112,621 B2 | 9/2006 | Rohrbaugh |
| 7,122,713 B2 | 10/2006 | Komatsu et al. |
| 7,125,470 B2 | 10/2006 | Graef et al. |
| 7,132,585 B2 | 11/2006 | Kudo et al. |
| 7,147,628 B2 | 12/2006 | Drevik |
| 7,150,729 B2 | 12/2006 | Shimada et al. |
| 7,154,019 B2 | 12/2006 | Mishima et al. |
| 7,160,281 B2 | 1/2007 | Leminh et al. |
| 7,163,528 B2 | 1/2007 | Christon |
| 7,166,190 B2 | 1/2007 | Graef et al. |
| 7,169,136 B2 | 1/2007 | Otsubo et al. |
| 7,183,360 B2 | 2/2007 | Daniel et al. |
| 7,189,888 B2 | 3/2007 | Wang et al. |
| 7,196,241 B2 | 3/2007 | Kinoshita et al. |
| 7,199,211 B2 | 4/2007 | Popp et al. |
| 7,204,830 B2 | 4/2007 | Mishima et al. |
| 7,207,978 B2 | 4/2007 | Takino et al. |
| 7,219,403 B2 | 5/2007 | Miyamoto et al. |
| 7,220,251 B2 | 5/2007 | Otsubo et al. |
| 7,241,280 B2 | 7/2007 | Christon et al. |
| 7,250,481 B2 | 7/2007 | Jaworek et al. |
| 7,252,657 B2 | 8/2007 | Mishima et al. |
| 7,265,258 B2 | 9/2007 | Hamilton |
| 7,270,651 B2 | 9/2007 | Adams |
| 7,285,178 B2 | 10/2007 | Mischler |
| 7,306,582 B2 | 12/2007 | Adams |
| 7,311,696 B2 | 12/2007 | Christon et al. |
| 7,311,968 B2 | 12/2007 | Ehrnsperger et al. |
| 7,312,372 B2 | 12/2007 | Miyama et al. |
| 7,318,820 B2 | 1/2008 | Lavon et al. |
| 7,329,244 B2 | 2/2008 | Otsubo et al. |
| 7,329,246 B2 | 2/2008 | Kinoshita et al. |
| 7,335,810 B2 | 2/2008 | Yoshimasa et al. |
| 7,377,914 B2 | 5/2008 | Lavon |
| 7,429,689 B2 | 9/2008 | Chen |
| 7,435,244 B2 | 10/2008 | Schroer, Jr. et al. |
| 7,465,373 B2 | 12/2008 | Graef et al. |
| 7,500,969 B2 | 3/2009 | Mishima et al. |
| 7,504,552 B2 | 3/2009 | Tamura et al. |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi et al. |
| 7,550,646 B2 | 6/2009 | Tamura et al. |
| 7,563,257 B2 | 7/2009 | Nakajima et al. |
| 7,588,561 B2 | 9/2009 | Kenmochi et al. |
| 7,594,904 B2 | 9/2009 | Rosenfeld et al. |
| 7,598,428 B2 | 10/2009 | Gustavsson et al. |
| 7,625,363 B2 | 12/2009 | Yoshimasa et al. |
| 7,641,642 B2 | 1/2010 | Murai et al. |
| 7,648,490 B2 | 1/2010 | Kuroda et al. |
| 7,652,111 B2 | 1/2010 | Hermeling et al. |
| 7,666,173 B2 | 2/2010 | Mishima et al. |
| 7,666,174 B2 | 2/2010 | Onishi et al. |
| 7,686,790 B2 | 3/2010 | Rasmussen et al. |
| 7,687,596 B2 | 3/2010 | Hermeling et al. |
| 7,695,461 B2 | 4/2010 | Rosenfeld et al. |
| 7,696,402 B2 | 4/2010 | Nishikawa et al. |
| 7,708,725 B2 | 5/2010 | Tamagawa et al. |
| 7,717,150 B2 | 5/2010 | Manabe et al. |
| 7,718,844 B2 | 5/2010 | Olson |
| 7,722,587 B2 | 5/2010 | Suzuki et al. |
| 7,722,590 B2 | 5/2010 | Tsuji et al. |
| 7,727,217 B2 | 6/2010 | Hancock-cooke |
| 7,736,351 B2 | 6/2010 | Nigam et al. |
| 7,737,324 B2 | 6/2010 | Lavon et al. |
| 7,744,576 B2 | 6/2010 | Busam |
| 7,744,578 B2 | 6/2010 | Tanio et al. |
| 7,750,203 B2 | 7/2010 | Becker et al. |
| 7,754,822 B2 | 7/2010 | Daniel et al. |
| 7,754,940 B2 | 7/2010 | Brisebois et al. |
| 7,759,540 B2 | 7/2010 | Litvay et al. |
| 7,763,004 B2 | 7/2010 | Lavon |
| 7,767,875 B2 | 8/2010 | Olson et al. |
| 7,767,876 B2 | 8/2010 | Davis et al. |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld et al. |
| 7,825,291 B2 | 11/2010 | Elfsberg et al. |
| 7,838,722 B2 | 11/2010 | Blessing et al. |
| 7,850,672 B2 | 12/2010 | Guidotti et al. |
| 7,851,667 B2 | 12/2010 | Becker et al. |
| 7,855,314 B2 | 12/2010 | Hanao et al. |
| 7,857,797 B2 | 12/2010 | Kudo et al. |
| 7,858,842 B2 | 12/2010 | Komatsu et al. |
| 7,884,259 B2 | 2/2011 | Hanao et al. |
| 7,888,549 B2 | 2/2011 | Jansson et al. |
| 7,910,797 B2 | 3/2011 | Nandrea et al. |
| 7,931,636 B2 | 4/2011 | Lavon et al. |
| 7,935,207 B2 | 5/2011 | Zhao et al. |
| 7,935,861 B2 | 5/2011 | Suzuki |
| 7,938,813 B2 | 5/2011 | Wang et al. |
| 7,942,858 B2 | 5/2011 | Francoeur et al. |
| 7,951,126 B2 | 5/2011 | Nanjyo et al. |

(56) References Cited

U.S. PATENT DOCUMENTS

| | | | |
|---|---|---|---|
| 7,956,236 B2 | 6/2011 | Ponomarenko et al. |
| 7,959,620 B2 | 6/2011 | Miura et al. |
| 7,982,091 B2 | 7/2011 | Konawa |
| 7,993,319 B2 | 8/2011 | Sperl |
| 8,017,827 B2 | 9/2011 | Hundorf et al. |
| 8,029,486 B2 | 10/2011 | Nakajima et al. |
| 8,030,536 B2 | 10/2011 | Ponomarenko et al. |
| 8,034,991 B2 | 10/2011 | Bruzadin et al. |
| 8,039,684 B2 | 10/2011 | Guidotti et al. |
| 8,052,454 B2 | 11/2011 | Polnyi |
| 8,057,620 B2 | 11/2011 | Perego et al. |
| 8,109,915 B2 | 2/2012 | Shimoe et al. |
| 8,124,828 B2 * | 2/2012 | Kline et al. |
| 8,133,212 B2 | 3/2012 | Takada |
| 8,148,598 B2 | 4/2012 | Tsang et al. |
| 8,163,124 B2 | 4/2012 | Moriura et al. |
| 8,167,862 B2 | 5/2012 | Digiacomantonio et al. |
| 8,173,858 B2 | 5/2012 | Kuroda et al. |
| 8,178,747 B2 | 5/2012 | Venturino et al. |
| 8,183,430 B2 | 5/2012 | Haakansson et al. |
| 8,186,296 B2 | 5/2012 | Brown |
| 8,187,239 B2 | 5/2012 | Lavon |
| 8,187,240 B2 | 5/2012 | Busam et al. |
| 8,198,506 B2 | 6/2012 | Venturino et al. |
| 8,211,815 B2 | 7/2012 | Baker et al. |
| 8,236,715 B2 | 8/2012 | Schmidt et al. |
| 8,237,012 B2 | 8/2012 | Miyama et al. |
| 8,246,594 B2 | 8/2012 | Sperl et al. |
| 8,258,367 B2 | 9/2012 | Lawson et al. |
| 8,268,424 B1 | 9/2012 | Suzuki et al. |
| 8,273,943 B2 | 9/2012 | Noda et al. |
| 8,282,617 B2 | 10/2012 | Kaneda |
| 8,283,516 B2 | 10/2012 | Litvay |
| 8,317,766 B2 | 11/2012 | Naoto et al. |
| 8,317,768 B2 | 11/2012 | Larsson |
| 8,319,005 B2 | 11/2012 | Becker et al. |
| 8,343,123 B2 | 1/2013 | Noda et al. |
| 8,343,296 B2 | 1/2013 | Blessing et al. |
| 8,360,977 B2 | 1/2013 | Marttila et al. |
| 8,361,047 B2 | 1/2013 | Mukai et al. |
| 8,377,025 B2 | 2/2013 | Nakajima et al. |
| 8,450,555 B2 | 5/2013 | Nhan et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,569,571 B2 | 10/2013 | Kline et al. |
| 8,581,019 B2 | 11/2013 | Carlucci et al. |
| 8,603,058 B2 | 12/2013 | Sperl et al. |
| 8,604,270 B2 | 12/2013 | Venturino et al. |
| 8,633,347 B2 | 1/2014 | Bianco et al. |
| 8,664,468 B2 | 3/2014 | Lawson et al. |
| 8,674,170 B2 | 3/2014 | Busam et al. |
| 8,734,417 B2 | 5/2014 | Lavon et al. |
| 8,766,031 B2 | 7/2014 | Becker et al. |
| 8,772,570 B2 | 7/2014 | Kawakami et al. |
| 8,784,594 B2 | 7/2014 | Blessing et al. |
| 8,785,715 B2 | 7/2014 | Wright et al. |
| 8,791,318 B2 | 7/2014 | Becker et al. |
| 8,936,584 B2 | 1/2015 | Zander et al. |
| 9,056,034 B2 | 6/2015 | Akiyama |
| 9,326,896 B2 | 5/2016 | Schäfer et al. |
| 10,130,527 B2 | 11/2018 | Peri et al. |
| 11,154,437 B2 * | 10/2021 | Peri .................. A61F 13/534 |
| 2001/0007065 A1 | 7/2001 | Blanchard et al. |
| 2001/0008964 A1 | 7/2001 | Kurata et al. |
| 2001/0016548 A1 | 8/2001 | Kugler et al. |
| 2001/0020157 A1 | 9/2001 | Mizutani et al. |
| 2001/0037101 A1 | 11/2001 | Allan et al. |
| 2001/0044610 A1 | 11/2001 | Kim et al. |
| 2002/0007167 A1 | 1/2002 | Dan et al. |
| 2002/0007169 A1 | 1/2002 | Graef |
| 2002/0016122 A1 | 2/2002 | Curro |
| 2002/0045881 A1 | 4/2002 | Kusibojoska et al. |
| 2002/0056516 A1 | 5/2002 | Ochi |
| 2002/0058919 A1 | 5/2002 | Hamilton et al. |
| 2002/0062112 A1 | 5/2002 | Mizutani |
| 2002/0062115 A1 | 5/2002 | Wada et al. |
| 2002/0062116 A1 | 5/2002 | Mizutani et al. |
| 2002/0065498 A1 | 5/2002 | Ohashi et al. |
| 2002/0072471 A1 | 6/2002 | Ikeuchi et al. |
| 2002/0082575 A1 | 6/2002 | Dan et al. |
| 2002/0087139 A1 | 7/2002 | Coenen et al. |
| 2002/0095126 A1 | 7/2002 | Inoue et al. |
| 2002/0095127 A1 | 7/2002 | Fish et al. |
| 2002/0102392 A1 | 8/2002 | Fish et al. |
| 2002/0115969 A1 | 8/2002 | Mori et al. |
| 2002/0115972 A1 | 8/2002 | Dabi et al. |
| 2002/0121848 A1 | 9/2002 | Lee et al. |
| 2002/0123728 A1 | 9/2002 | Graef et al. |
| 2002/0123848 A1 | 9/2002 | Schneiderman et al. |
| 2002/0151634 A1 | 10/2002 | Rohrbaugh et al. |
| 2002/0151861 A1 | 10/2002 | Klemp et al. |
| 2002/0173767 A1 | 11/2002 | Coenen |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada |
| 2003/0084983 A1 | 5/2003 | Rangachari et al. |
| 2003/0088223 A1 | 5/2003 | Vogt et al. |
| 2003/0105190 A1 | 6/2003 | Diehl |
| 2003/0109839 A1 | 6/2003 | Costea |
| 2003/0114811 A1 | 6/2003 | Christon |
| 2003/0114816 A1 | 6/2003 | Underhill et al. |
| 2003/0114818 A1 | 6/2003 | Benecke |
| 2003/0115969 A1 | 6/2003 | Koyano |
| 2003/0120235 A1 | 6/2003 | Boulanger |
| 2003/0120249 A1 | 6/2003 | Wulz et al. |
| 2003/0135176 A1 | 7/2003 | Delzer et al. |
| 2003/0135177 A1 | 7/2003 | Baker |
| 2003/0135181 A1 | 7/2003 | Chen |
| 2003/0135182 A1 | 7/2003 | Woon |
| 2003/0139712 A1 | 7/2003 | Dodge et al. |
| 2003/0139715 A1 | 7/2003 | Dodge et al. |
| 2003/0139718 A1 | 7/2003 | Graef et al. |
| 2003/0144642 A1 | 7/2003 | Dopps et al. |
| 2003/0144644 A1 | 7/2003 | Murai |
| 2003/0148684 A1 | 8/2003 | Cramer et al. |
| 2003/0148694 A1 | 8/2003 | Ghiam |
| 2003/0158530 A1 | 8/2003 | Diehl et al. |
| 2003/0158531 A1 | 8/2003 | Chmielewski |
| 2003/0158532 A1 | 8/2003 | Magee |
| 2003/0167045 A1 | 9/2003 | Graef et al. |
| 2003/0171727 A1 | 9/2003 | Graef et al. |
| 2003/0208175 A1 | 11/2003 | Gross et al. |
| 2003/0225385 A1 | 12/2003 | Glaug et al. |
| 2003/0233082 A1 | 12/2003 | Kline |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett et al. |
| 2004/0063367 A1 | 4/2004 | Dodge et al. |
| 2004/0064113 A1 | 4/2004 | Erdman |
| 2004/0064115 A1 | 4/2004 | Arora et al. |
| 2004/0064116 A1 | 4/2004 | Arora et al. |
| 2004/0064125 A1 | 4/2004 | Justmann et al. |
| 2004/0065420 A1 | 4/2004 | Graef et al. |
| 2004/0082928 A1 | 4/2004 | Pesce et al. |
| 2004/0097895 A1 | 5/2004 | Busam |
| 2004/0122411 A1 | 6/2004 | Hancock-cooke |
| 2004/0127131 A1 | 7/2004 | Potnis |
| 2004/0127871 A1 | 7/2004 | Odorzynski et al. |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko |
| 2004/0162536 A1 | 8/2004 | Becker |
| 2004/0167486 A1 | 8/2004 | Busam |
| 2004/0167489 A1 | 8/2004 | Kellenberger et al. |
| 2004/0170813 A1 | 9/2004 | Digiacomantonio |
| 2004/0193127 A1 | 9/2004 | Hansson et al. |
| 2004/0214499 A1 | 10/2004 | Qin et al. |

(56) References Cited

U.S. PATENT DOCUMENTS

| | | |
|---|---|---|
| 2004/0215160 A1 | 10/2004 | Chmielewski et al. |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0236455 A1 | 11/2004 | Woltman et al. |
| 2004/0243078 A1 | 12/2004 | Guidotti et al. |
| 2004/0249355 A1 | 12/2004 | Tanio |
| 2004/0260259 A1 | 12/2004 | Baker |
| 2005/0001929 A1 | 1/2005 | Ochial et al. |
| 2005/0004543 A1 | 1/2005 | Schroer et al. |
| 2005/0004548 A1 | 1/2005 | Otsubo et al. |
| 2005/0008839 A1 | 1/2005 | Cramer |
| 2005/0018258 A1 | 1/2005 | Miyagi et al. |
| 2005/0038401 A1 | 2/2005 | Suzuki et al. |
| 2005/0070867 A1 | 3/2005 | Beruda et al. |
| 2005/0085784 A1 | 4/2005 | Leminh et al. |
| 2005/0090789 A1 | 4/2005 | Graef et al. |
| 2005/0101929 A1 | 5/2005 | Waksmundzki et al. |
| 2005/0137543 A1 | 6/2005 | Underhill et al. |
| 2005/0148258 A1 | 7/2005 | Chakravarty et al. |
| 2005/0148961 A1 | 7/2005 | Sosalla |
| 2005/0148990 A1 | 7/2005 | Shimoe et al. |
| 2005/0154363 A1 | 7/2005 | Minato et al. |
| 2005/0159720 A1 | 7/2005 | Gentilcore |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | Lavon et al. |
| 2005/0215752 A1 | 9/2005 | Popp et al. |
| 2005/0217791 A1 | 10/2005 | Costello |
| 2005/0229543 A1 | 10/2005 | Tippey |
| 2005/0234414 A1 | 10/2005 | Liu |
| 2005/0245684 A1 | 11/2005 | Daniel et al. |
| 2005/0288645 A1 | 12/2005 | Lavon |
| 2005/0288646 A1 | 12/2005 | Lavon |
| 2006/0004334 A1 | 1/2006 | Schlinz et al. |
| 2006/0021695 A1 | 2/2006 | Blessing |
| 2006/0024433 A1 | 2/2006 | Blessing |
| 2006/0069367 A1 | 3/2006 | Waksmundzki et al. |
| 2006/0069371 A1 | 3/2006 | Ohashi |
| 2006/0073969 A1 | 4/2006 | Torii et al. |
| 2006/0081348 A1 | 4/2006 | Graef et al. |
| 2006/0129114 A1 | 6/2006 | Mason, Jr. et al. |
| 2006/0142724 A1 | 6/2006 | Watanabe et al. |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo |
| 2006/0202380 A1 | 9/2006 | Bentley et al. |
| 2006/0206091 A1 | 9/2006 | Cole et al. |
| 2006/0211828 A1 | 9/2006 | Daniel et al. |
| 2006/0240229 A1 | 10/2006 | Ehrnsperger et al. |
| 2006/0264860 A1 | 11/2006 | Lavon |
| 2006/0264861 A1 | 11/2006 | Lavon et al. |
| 2006/0271010 A1 | 11/2006 | Lavon |
| 2007/0027436 A1 | 2/2007 | Nakagawa et al. |
| 2007/0032770 A1 | 2/2007 | Lavon et al. |
| 2007/0043191 A1 | 2/2007 | Hermeling et al. |
| 2007/0043330 A1 | 2/2007 | Lankhof |
| 2007/0044903 A1 | 3/2007 | Wisneski et al. |
| 2007/0049892 A1 | 3/2007 | Lord et al. |
| 2007/0049897 A1 | 3/2007 | Lavon et al. |
| 2007/0073253 A1 | 3/2007 | Miyama et al. |
| 2007/0078422 A1 | 4/2007 | Glaug et al. |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto et al. |
| 2007/0106013 A1 | 5/2007 | Adachi et al. |
| 2007/0118087 A1 | 5/2007 | Flohr |
| 2007/0123834 A1 | 5/2007 | Mcdowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug et al. |
| 2007/0219521 A1 | 9/2007 | Hird |
| 2007/0219523 A1 | 9/2007 | Bruun et al. |
| 2007/0239125 A9 | 10/2007 | Erdman et al. |
| 2007/0244455 A1 | 10/2007 | Hansson et al. |
| 2007/0246147 A1 | 10/2007 | Venturino et al. |
| 2007/0255245 A1 | 11/2007 | Asp et al. |
| 2007/0282288 A1 | 12/2007 | Noda et al. |
| 2007/0282290 A1 | 12/2007 | Cole et al. |
| 2007/0282291 A1 | 12/2007 | Cole et al. |
| 2007/0287971 A1 | 12/2007 | Roe et al. |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda et al. |
| 2008/0125735 A1 | 5/2008 | Busam et al. |
| 2008/0132864 A1 | 6/2008 | Lawson et al. |
| 2008/0208154 A1 | 8/2008 | Oetjen |
| 2008/0221538 A1 | 9/2008 | Zhao |
| 2008/0221539 A1 | 9/2008 | Zhao |
| 2008/0228158 A1 | 9/2008 | Sue et al. |
| 2008/0262459 A1 | 10/2008 | Kamoto et al. |
| 2008/0268194 A1 | 10/2008 | Kim et al. |
| 2008/0269705 A1 | 10/2008 | Kainth et al. |
| 2008/0274227 A1 | 11/2008 | Boatman et al. |
| 2008/0281287 A1 | 11/2008 | Marcelo et al. |
| 2008/0294140 A1 | 11/2008 | Ecker et al. |
| 2008/0312617 A1 | 12/2008 | Hundorf |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf |
| 2008/0312623 A1 | 12/2008 | Hundorf et al. |
| 2008/0312624 A1 | 12/2008 | Hundorf |
| 2008/0312625 A1 | 12/2008 | Hundorf et al. |
| 2008/0312627 A1 | 12/2008 | Takeuchi et al. |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0058994 A1 | 3/2009 | Kao et al. |
| 2009/0062760 A1 | 3/2009 | Wright et al. |
| 2009/0112173 A1 | 4/2009 | Bissah et al. |
| 2009/0112175 A1 | 4/2009 | Bissah et al. |
| 2009/0157022 A1 | 6/2009 | Macdonald et al. |
| 2009/0192035 A1 | 7/2009 | Stueven et al. |
| 2009/0240220 A1 | 9/2009 | Macdonald et al. |
| 2009/0247977 A1 | 10/2009 | Takeuchi |
| 2009/0258994 A1 | 10/2009 | Stueven et al. |
| 2009/0270825 A1 | 10/2009 | Wciorka et al. |
| 2009/0275470 A1 | 11/2009 | Nagasawa et al. |
| 2009/0298963 A1 | 12/2009 | Matsumoto et al. |
| 2009/0299312 A1 | 12/2009 | Macdonald et al. |
| 2009/0306618 A1 | 12/2009 | Kudo et al. |
| 2009/0318884 A1 | 12/2009 | Meyer et al. |
| 2009/0326494 A1 | 12/2009 | Uchida et al. |
| 2009/0326497 A1 | 12/2009 | Schmidt |
| 2010/0051166 A1 | 3/2010 | Hundorf |
| 2010/0062165 A1 | 3/2010 | Suzuki et al. |
| 2010/0062934 A1 | 3/2010 | Suzuki et al. |
| 2010/0063470 A1 | 3/2010 | Suzuki et al. |
| 2010/0068520 A1 | 3/2010 | Stueven |
| 2010/0100065 A1 | 4/2010 | De et al. |
| 2010/0115237 A1 | 5/2010 | Brewer et al. |
| 2010/0121296 A1 | 5/2010 | Noda et al. |
| 2010/0137773 A1 | 6/2010 | Gross et al. |
| 2010/0137823 A1 | 6/2010 | Corneliusson et al. |
| 2010/0198179 A1 | 8/2010 | Noda et al. |
| 2010/0228210 A1 | 9/2010 | Busam |
| 2010/0241096 A1 | 9/2010 | Lavon et al. |
| 2010/0241097 A1 | 9/2010 | Nigam et al. |
| 2010/0262099 A1 | 10/2010 | Klofta |
| 2010/0262104 A1 | 10/2010 | Carlucci et al. |

(56) References Cited

U.S. PATENT DOCUMENTS

| | | |
|---|---|---|
| 2010/0274208 A1 | 10/2010 | Gabrielii et al. |
| 2010/0274210 A1 | 10/2010 | Noda et al. |
| 2010/0305537 A1 | 12/2010 | Ashton |
| 2010/0312208 A1 | 12/2010 | Bond et al. |
| 2010/0324521 A1 | 12/2010 | Mukai et al. |
| 2010/0324523 A1 | 12/2010 | Mukai et al. |
| 2011/0034603 A1 | 2/2011 | Fujino et al. |
| 2011/0041999 A1 | 2/2011 | Hundorf et al. |
| 2011/0046592 A1 | 2/2011 | Nishikawa et al. |
| 2011/0060301 A1 | 3/2011 | Nishikawa et al. |
| 2011/0060303 A1 | 3/2011 | Bissah et al. |
| 2011/0066127 A1 | 3/2011 | Kuwano et al. |
| 2011/0071486 A1 | 3/2011 | Harada et al. |
| 2011/0092944 A1 | 4/2011 | Sagisaka et al. |
| 2011/0112498 A1 | 5/2011 | Nhan et al. |
| 2011/0125120 A1 | 5/2011 | Nishitani et al. |
| 2011/0130732 A1 | 6/2011 | Jackels et al. |
| 2011/0130737 A1 | 6/2011 | Sagisaka et al. |
| 2011/0137276 A1 | 6/2011 | Yoshikawa |
| 2011/0144602 A1 | 6/2011 | Long |
| 2011/0144604 A1 | 6/2011 | Noda et al. |
| 2011/0144606 A1 | 6/2011 | Nandrea et al. |
| 2011/0152813 A1 | 6/2011 | Ellingson |
| 2011/0166540 A1 | 7/2011 | Yang |
| 2011/0172630 A1 | 7/2011 | Nomoto et al. |
| 2011/0174430 A1 | 7/2011 | Zhao et al. |
| 2011/0196330 A1 | 8/2011 | Hammons |
| 2011/0208147 A1 | 8/2011 | Kawakami et al. |
| 2011/0250413 A1 | 10/2011 | Lu |
| 2011/0268932 A1 | 11/2011 | Catalan |
| 2011/0274834 A1 | 11/2011 | Brown et al. |
| 2011/0288513 A1 | 11/2011 | Hundorf et al. |
| 2011/0288514 A1 | 11/2011 | Kuroda et al. |
| 2011/0295222 A1 | 12/2011 | Becker et al. |
| 2011/0319846 A1 | 12/2011 | Rinnert et al. |
| 2011/0319848 A1 | 12/2011 | Mckiernan |
| 2011/0319851 A1 | 12/2011 | Kudo et al. |
| 2012/0004633 A1 | 1/2012 | R. Marcelo |
| 2012/0016326 A1 | 1/2012 | Brennan et al. |
| 2012/0022479 A1 | 1/2012 | Cotton |
| 2012/0035566 A1 | 2/2012 | Sagisaka et al. |
| 2012/0035576 A1 | 2/2012 | Ichikawa et al. |
| 2012/0064792 A1 | 3/2012 | Bauduin |
| 2012/0071848 A1 | 3/2012 | Zhang et al. |
| 2012/0165771 A1 | 6/2012 | Ruman et al. |
| 2012/0165776 A1 | 6/2012 | Mcgregor |
| 2012/0170779 A1 | 7/2012 | Hildebrandt |
| 2012/0175056 A1 | 7/2012 | Tsang et al. |
| 2012/0184934 A1 | 7/2012 | Venturino et al. |
| 2012/0220972 A1 | 8/2012 | Kawamura et al. |
| 2012/0232514 A1 | 9/2012 | Baker et al. |
| 2012/0238977 A1 | 9/2012 | Oku et al. |
| 2012/0253306 A1 | 10/2012 | Otsubo et al. |
| 2012/0256750 A1 | 10/2012 | Novak |
| 2012/0271262 A1 | 10/2012 | Venturino et al. |
| 2012/0312491 A1 | 12/2012 | Jackels |
| 2012/0316046 A1 | 12/2012 | Jackels et al. |
| 2012/0316523 A1 | 12/2012 | Hippe |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0316530 A1 | 12/2012 | Armstrong-ostle et al. |
| 2012/0323195 A1 | 12/2012 | Ehrnsperger et al. |
| 2012/0323201 A1 | 12/2012 | Bissah et al. |
| 2012/0323202 A1 | 12/2012 | Bissah et al. |
| 2013/0035656 A1 | 2/2013 | Moriya et al. |
| 2013/0041334 A1 | 2/2013 | Prioleau et al. |
| 2013/0178811 A1 | 7/2013 | Kikuchi et al. |
| 2013/0211354 A1 | 8/2013 | Tsuji et al. |
| 2013/0211358 A1 | 8/2013 | Kikkawa et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van |
| 2013/0240125 A1 | 9/2013 | Heinz et al. |
| 2013/0310784 A1 | 11/2013 | Bryant |
| 2014/0005622 A1 | 1/2014 | Wirtz |
| 2014/0005623 A1 | 1/2014 | Wirtz et al. |
| 2014/0027066 A1 | 1/2014 | Jackels et al. |
| 2014/0039437 A1 | 2/2014 | Van De Maele |
| 2014/0045683 A1 | 2/2014 | Loick et al. |
| 2014/0102183 A1 | 4/2014 | Agami et al. |
| 2014/0121623 A1 | 5/2014 | Kirby |
| 2014/0121625 A1 | 5/2014 | Kirby et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti |
| 2014/0163503 A1 | 6/2014 | Arizti |
| 2014/0163506 A1 | 6/2014 | Roe |
| 2014/0163511 A1 | 6/2014 | Roe et al. |
| 2014/0171893 A1 | 6/2014 | Lawson et al. |
| 2014/0299815 A1 | 10/2014 | Ueda et al. |
| 2014/0318694 A1 | 10/2014 | Blessing et al. |
| 2014/0324007 A1 | 10/2014 | Hundorf et al. |
| 2014/0324008 A1 | 10/2014 | Hundorf et al. |
| 2014/0371701 A1 | 12/2014 | Bianchi |
| 2015/0065975 A1 | 3/2015 | Roe |
| 2015/0065981 A1 | 3/2015 | Roe |
| 2015/0065986 A1 | 3/2015 | Blessing et al. |
| 2015/0080821 A1 | 3/2015 | Peri et al. |
| 2015/0080837 A1 | 3/2015 | Rosati et al. |
| 2015/0080839 A1 | 3/2015 | Trapp et al. |
| 2015/0173967 A1 | 6/2015 | Kreuzer |
| 2015/0173968 A1 | 6/2015 | Joseph |
| 2015/0250662 A1 | 9/2015 | Isele et al. |
| 2015/0250663 A1 | 9/2015 | Wagner et al. |
| 2015/0273433 A1 | 10/2015 | Nakatsuru et al. |
| 2019/0046368 A1 | 2/2019 | Peri et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2702001 | 10/2010 |
| CA | 2712563 A1 | 3/2011 |
| CN | 1238171 A | 12/1999 |
| CN | 2362468 Y | 2/2000 |
| CN | 1371671 A | 10/2002 |
| CN | 2527254 Y | 12/2002 |
| CN | 2535020 Y | 2/2003 |
| CN | 2548609 Y | 5/2003 |
| CN | 1471380 A | 1/2004 |
| CN | 1539391 A | 10/2004 |
| CN | 1939242 | 4/2007 |
| CN | 101292930 | 10/2008 |
| CN | 201263750 Y | 7/2009 |
| CN | 201591689 U | 9/2010 |
| CN | 201855366 U | 6/2011 |
| DE | 3205931 C2 | 8/1985 |
| DE | 3608114 A1 | 9/1987 |
| DE | 19732499 | 2/1999 |
| DE | 10204937 A1 | 8/2003 |
| EP | 083022 | 7/1983 |
| EP | 149880 A2 | 7/1985 |
| EP | 203289 | 12/1986 |
| EP | 0203289 A2 | 12/1986 |
| EP | 0206208 A1 | 12/1986 |
| EP | 209561 | 1/1987 |
| EP | 297411 | 1/1989 |
| EP | 374542 | 6/1990 |
| EP | 0403832 A1 | 12/1990 |
| EP | 481322 | 4/1992 |
| EP | 530438 A1 | 3/1993 |
| EP | 547847 | 6/1993 |
| EP | 555346 | 8/1993 |
| EP | 559476 A1 | 9/1993 |
| EP | 304957 B2 | 4/1994 |
| EP | 591647 | 4/1994 |
| EP | 597273 | 5/1994 |

(56) References Cited

FOREIGN PATENT DOCUMENTS

| | | |
|---|---|---|
| EP | 601610 | 6/1994 |
| EP | 632068 A1 | 1/1995 |
| EP | 0640330 A1 | 3/1995 |
| EP | 0668066 | 9/1995 |
| EP | 685214 | 12/1995 |
| EP | 687453 | 12/1995 |
| EP | 0689817 A2 | 1/1996 |
| EP | 0691133 | 1/1996 |
| EP | 0700673 A1 | 3/1996 |
| EP | 0394274 | 7/1996 |
| EP | 394274 B2 | 7/1996 |
| EP | 0724418 A1 | 8/1996 |
| EP | 0725613 A1 | 8/1996 |
| EP | 725615 | 8/1996 |
| EP | 0725616 A1 | 8/1996 |
| EP | 0737055 A1 | 10/1996 |
| EP | 758543 | 2/1997 |
| EP | 0761194 | 3/1997 |
| EP | 769284 | 4/1997 |
| EP | 0778762 A1 | 6/1997 |
| EP | 0781537 A1 | 7/1997 |
| EP | 783877 | 7/1997 |
| EP | 787472 | 8/1997 |
| EP | 788874 | 8/1997 |
| EP | 0790839 A1 | 8/1997 |
| EP | 0796068 A2 | 9/1997 |
| EP | 799004 | 10/1997 |
| EP | 822794 | 2/1998 |
| EP | 826351 | 3/1998 |
| EP | 844861 | 6/1998 |
| EP | 863733 | 9/1998 |
| EP | 971751 | 9/1998 |
| EP | 875224 | 11/1998 |
| EP | 0875224 A1 | 11/1998 |
| EP | 880955 | 12/1998 |
| EP | 891758 | 1/1999 |
| EP | 0893115 | 1/1999 |
| EP | 724418 B1 | 3/1999 |
| EP | 725613 B1 | 3/1999 |
| EP | 725616 B1 | 3/1999 |
| EP | 904755 | 3/1999 |
| EP | 916327 | 5/1999 |
| EP | 0916327 A1 | 5/1999 |
| EP | 925769 | 6/1999 |
| EP | 933074 | 8/1999 |
| EP | 937736 A2 | 8/1999 |
| EP | 941157 | 9/1999 |
| EP | 947549 | 10/1999 |
| EP | 951887 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 | 3/2000 |
| EP | 0988846 | 3/2000 |
| EP | 1005847 B1 | 6/2000 |
| EP | 1008333 A3 | 6/2000 |
| EP | 1018999 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |
| EP | 1071388 | 1/2001 |
| EP | 1078618 | 2/2001 |
| EP | 1088537 A2 | 4/2001 |
| EP | 796068 B1 | 5/2001 |
| EP | 752892 B1 | 7/2001 |
| EP | 1116479 A2 | 7/2001 |
| EP | 1132069 | 9/2001 |
| EP | 1173128 | 1/2002 |
| EP | 1184018 | 3/2002 |
| EP | 1199059 | 4/2002 |
| EP | 1199327 A2 | 4/2002 |
| EP | 1208824 | 5/2002 |
| EP | 0793469 | 6/2002 |
| EP | 793469 B1 | 6/2002 |
| EP | 1210925 | 6/2002 |
| EP | 1224922 | 7/2002 |
| EP | 1225857 | 7/2002 |
| EP | 1253231 | 10/2002 |
| EP | 1262531 A1 | 12/2002 |
| EP | 0737056 | 1/2003 |
| EP | 1275358 | 1/2003 |
| EP | 1275361 | 1/2003 |
| EP | 1293187 | 3/2003 |
| EP | 1339368 | 9/2003 |
| EP | 1374817 | 1/2004 |
| EP | 1388334 | 2/2004 |
| EP | 1402863 | 3/2004 |
| EP | 962208 | 8/2004 |
| EP | 1447066 A1 | 8/2004 |
| EP | 1447067 A1 | 8/2004 |
| EP | 1460987 | 9/2004 |
| EP | 963749 | 11/2004 |
| EP | 1263374 B1 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 0984 | 10/2005 |
| EP | 1586289 | 10/2005 |
| EP | 1588723 | 10/2005 |
| EP | 1605882 | 12/2005 |
| EP | 1609448 | 12/2005 |
| EP | 1019003 B1 | 1/2006 |
| EP | 1621166 | 2/2006 |
| EP | 1621167 A2 | 2/2006 |
| EP | 1632206 | 3/2006 |
| EP | 1642556 | 4/2006 |
| EP | 1403419 | 5/2006 |
| EP | 1656162 | 5/2006 |
| EP | 1669046 | 6/2006 |
| EP | 1019002 B1 | 8/2006 |
| EP | 1688114 | 8/2006 |
| EP | 1690556 A2 | 8/2006 |
| EP | 2314265 | 8/2006 |
| EP | 1723939 | 11/2006 |
| EP | 1192312 B1 | 12/2006 |
| EP | 1013252 B1 | 1/2007 |
| EP | 1738727 | 1/2007 |
| EP | 1754461 | 2/2007 |
| EP | 1787611 | 5/2007 |
| EP | 1175194 B1 | 6/2007 |
| EP | 1813238 | 8/2007 |
| EP | 1304986 B1 | 11/2007 |
| EP | 1332742 B1 | 6/2008 |
| EP | 2008626 | 12/2008 |
| EP | 2055279 A1 | 5/2009 |
| EP | 0980 | 6/2009 |
| EP | 2093049 | 8/2009 |
| EP | 2130522 | 12/2009 |
| EP | 1621165 | 4/2010 |
| EP | 1196122 B2 | 11/2011 |
| EP | 2399944 A1 | 12/2011 |
| EP | 2444046 A1 | 4/2012 |
| EP | 2532328 | 12/2012 |
| EP | 2532329 A1 | 12/2012 |
| EP | 2532332 A1 | 12/2012 |
| EP | 2535027 A1 * | 12/2012 | ............ A61F 13/15 |
| EP | 2535027 A1 | 12/2012 |
| EP | 2586409 A1 | 5/2013 |
| EP | 2656826 | 10/2013 |
| EP | 2679210 A1 | 1/2014 |
| EP | 2740449 | 6/2014 |
| EP | 2740450 A1 | 6/2014 |
| EP | 2740452 A1 | 6/2014 |
| EP | 2944376 A1 | 11/2015 |
| ES | 2213491 | 8/2004 |
| FR | 2566631 | 1/1986 |
| FR | 2583377 | 12/1986 |

(56) References Cited

FOREIGN PATENT DOCUMENTS

| | | |
|---|---|---|
| FR | 2612770 | 9/1988 |
| FR | 2810234 | 12/2001 |
| GB | 1307441 A | 2/1973 |
| GB | 1333081 A | 10/1973 |
| GB | 1513055 A | 6/1978 |
| GB | 2101468 | 1/1983 |
| GB | 2170108 A | 7/1986 |
| GB | 2262873 | 7/1993 |
| GB | 2288540 A | 10/1995 |
| GB | 2354449 A1 | 3/2001 |
| GB | 2452260 A | 3/2009 |
| GB | 2452260 A * | 3/2009 ............. A61F 13/42 |
| GR | 851769 B | 11/1985 |
| IN | 212479 | 3/2007 |
| IN | 208543 | 8/2007 |
| JP | 5572928 | 5/1980 |
| JP | 598322 | 1/1984 |
| JP | 63148323 U | 9/1988 |
| JP | 2107250 | 4/1990 |
| JP | 03224481 | 10/1991 |
| JP | 04122256 | 4/1992 |
| JP | 04341368 | 11/1992 |
| JP | 06191505 | 7/1994 |
| JP | 06269475 A | 9/1994 |
| JP | 07124193 | 5/1995 |
| JP | 08215629 | 8/1996 |
| JP | H10295728 A | 11/1998 |
| JP | 10328232 | 12/1998 |
| JP | 11033056 | 2/1999 |
| JP | 11318980 | 11/1999 |
| JP | 11320742 | 11/1999 |
| JP | 2000232985 A | 8/2000 |
| JP | 2000238161 A | 9/2000 |
| JP | 2001037810 A | 2/2001 |
| JP | 2001046435 A | 2/2001 |
| JP | 2001120597 A | 5/2001 |
| JP | 2001158074 A | 6/2001 |
| JP | 2001178768 A | 7/2001 |
| JP | 2001198157 A | 7/2001 |
| JP | 2001224626 A | 8/2001 |
| JP | 2001258935 A | 9/2001 |
| JP | 2001277394 A | 10/2001 |
| JP | 2001301857 A | 10/2001 |
| JP | 03420481 | 11/2001 |
| JP | 2001321397 A | 11/2001 |
| JP | 2001353174 A | 12/2001 |
| JP | 2002052042 A | 2/2002 |
| JP | 2002065718 A | 3/2002 |
| JP | 2002113800 A | 4/2002 |
| JP | 2002165832 A | 6/2002 |
| JP | 2002165836 A | 6/2002 |
| JP | 2002178429 A | 6/2002 |
| JP | 2002272769 A | 9/2002 |
| JP | 2002320641 A | 11/2002 |
| JP | 2002325792 A | 11/2002 |
| JP | 2002325799 A | 11/2002 |
| JP | 2002369841 A | 12/2002 |
| JP | 2003126140 A | 5/2003 |
| JP | 2003153955 A | 5/2003 |
| JP | 2003265523 A | 9/2003 |
| JP | 2003265524 A | 9/2003 |
| JP | 2003275237 A | 9/2003 |
| JP | 2003325563 A | 11/2003 |
| JP | 2004089269 A | 3/2004 |
| JP | 03566012 | 6/2004 |
| JP | 03568146 | 6/2004 |
| JP | 2004222868 A | 8/2004 |
| JP | 03616077 | 11/2004 |
| JP | 2004337314 A | 12/2004 |
| JP | 2004337385 A | 12/2004 |
| JP | 2004350864 A | 12/2004 |
| JP | 03640475 | 1/2005 |
| JP | 2005000312 A | 1/2005 |
| JP | 03660816 | 3/2005 |
| JP | 03676219 | 5/2005 |
| JP | 2005118339 A | 5/2005 |
| JP | 03688403 | 6/2005 |
| JP | 03705943 | 8/2005 |
| JP | 03719819 | 9/2005 |
| JP | 03724963 | 9/2005 |
| JP | 03725008 | 9/2005 |
| JP | 03737376 | 11/2005 |
| JP | 2006014792 A | 1/2006 |
| JP | 03781617 | 3/2006 |
| JP | 2006110329 A | 4/2006 |
| JP | 2006513824 A | 4/2006 |
| JP | 03801449 | 5/2006 |
| JP | 2006116036 A | 5/2006 |
| JP | 03850102 | 9/2006 |
| JP | 03850207 | 9/2006 |
| JP | 03856941 | 9/2006 |
| JP | 03868628 | 10/2006 |
| JP | 03874499 | 11/2006 |
| JP | 03877702 | 11/2006 |
| JP | 2006325639 A | 12/2006 |
| JP | 2006346021 A | 12/2006 |
| JP | 03904356 | 1/2007 |
| JP | 2007007455 A | 1/2007 |
| JP | 2007007456 A | 1/2007 |
| JP | 03926042 | 3/2007 |
| JP | 03934855 | 3/2007 |
| JP | 2007089906 A | 4/2007 |
| JP | 2007105198 A | 4/2007 |
| JP | 2007130504 A | 5/2007 |
| JP | 2007152033 A | 6/2007 |
| JP | 03986210 | 7/2007 |
| JP | 03986222 | 7/2007 |
| JP | 2007167453 A | 7/2007 |
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 | 11/2007 |
| JP | 04058281 | 12/2007 |
| JP | 04061086 | 12/2007 |
| JP | 04092319 | 3/2008 |
| JP | 2008080150 A | 4/2008 |
| JP | 2008093289 A | 4/2008 |
| JP | 04124322 | 5/2008 |
| JP | 2008119081 A | 5/2008 |
| JP | 2008136739 A | 6/2008 |
| JP | 2008136877 A | 6/2008 |
| JP | 04148594 | 7/2008 |
| JP | 04148620 | 7/2008 |
| JP | 2008154606 A | 7/2008 |
| JP | 04162609 | 8/2008 |
| JP | 04162637 | 8/2008 |
| JP | 04166923 | 8/2008 |
| JP | 04167406 | 8/2008 |
| JP | 04173723 | 8/2008 |
| JP | 4177770 B2 | 8/2008 |
| JP | 04190675 | 9/2008 |
| JP | 04190693 | 9/2008 |
| JP | 04208338 | 10/2008 |
| JP | 2008246089 A | 10/2008 |
| JP | 04230971 | 12/2008 |
| JP | 2008295475 A | 12/2008 |
| JP | 2008295713 A | 12/2008 |
| JP | 04261593 | 2/2009 |
| JP | 2009028186 A | 2/2009 |
| JP | 2009082481 A | 4/2009 |
| JP | 2009112590 A | 5/2009 |
| JP | 2009136601 A | 6/2009 |
| JP | 2009142401 A | 7/2009 |
| JP | 04322228 | 8/2009 |
| JP | 2009201878 A | 9/2009 |
| JP | 04392936 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 A | 1/2010 |
| JP | 04458702 | 2/2010 |
| JP | 04459013 | 2/2010 |

(56) References Cited

FOREIGN PATENT DOCUMENTS

| | | |
|---|---|---|
| JP | 2010022560 A | 2/2010 |
| JP | 04481325 | 3/2010 |
| JP | 2010046155 A | 3/2010 |
| JP | 2010051654 A | 3/2010 |
| JP | 2010063814 A | 3/2010 |
| JP | 2010063944 A | 3/2010 |
| JP | 04492957 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 A | 6/2010 |
| JP | 2010131297 A | 6/2010 |
| JP | 2010136917 A | 6/2010 |
| JP | 2010136973 A | 6/2010 |
| JP | 04540563 | 7/2010 |
| JP | 4577766 B2 | 9/2010 |
| JP | 04587947 | 9/2010 |
| JP | 2010194124 A | 9/2010 |
| JP | 2010194218 A | 9/2010 |
| JP | 2010201093 A | 9/2010 |
| JP | 2010221067 A | 10/2010 |
| JP | 04620299 | 11/2010 |
| JP | 04627472 | 11/2010 |
| JP | 04627473 | 11/2010 |
| JP | 04638087 | 12/2010 |
| JP | 04652626 | 12/2010 |
| JP | 2010273842 A | 12/2010 |
| JP | 2010284418 A | 12/2010 |
| JP | 2011000480 A | 1/2011 |
| JP | 2011030700 A | 2/2011 |
| JP | 04693574 | 3/2011 |
| JP | 2011067484 A | 4/2011 |
| JP | 2011072720 A | 4/2011 |
| JP | 2011104014 A | 6/2011 |
| JP | 2011104122 A | 6/2011 |
| JP | 2011120661 A | 6/2011 |
| JP | 2011125360 A | 6/2011 |
| JP | 2011125537 A | 6/2011 |
| JP | 2011517703 A | 6/2011 |
| JP | 04776516 | 7/2011 |
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 A | 8/2011 |
| JP | 04824882 | 9/2011 |
| JP | 4850272 B2 | 10/2011 |
| JP | 04855533 | 11/2011 |
| JP | 2011239858 A | 12/2011 |
| JP | 2011240050 A | 12/2011 |
| JP | 04931572 | 2/2012 |
| JP | 04953618 | 3/2012 |
| JP | 04969437 | 4/2012 |
| JP | 04969640 | 4/2012 |
| JP | 4971491 B2 | 4/2012 |
| JP | 04974524 | 4/2012 |
| JP | 04979780 | 4/2012 |
| JP | 04937225 | 5/2012 |
| JP | 2012100886 A | 5/2012 |
| JP | 05016020 | 6/2012 |
| JP | 05027364 | 6/2012 |
| JP | 5715806 B2 | 6/2012 |
| JP | 2012115378 A | 6/2012 |
| JP | 05031082 | 7/2012 |
| JP | 05042351 | 7/2012 |
| JP | 05043569 | 7/2012 |
| JP | 05043591 | 7/2012 |
| JP | 05046488 | 7/2012 |
| JP | 2012125452 A | 7/2012 |
| JP | 2012125625 A | 7/2012 |
| JP | 05053765 | 8/2012 |
| JP | 05070275 | 8/2012 |
| JP | 05079931 B1 | 9/2012 |
| JP | 05080189 | 9/2012 |
| JP | 05084442 | 9/2012 |
| JP | 05084476 | 9/2012 |
| JP | 5085770 B2 | 9/2012 |
| JP | 05089269 | 9/2012 |
| JP | 2012179286 A | 9/2012 |
| JP | 05113146 | 10/2012 |
| JP | 05129536 | 11/2012 |
| JP | 2012223230 A | 11/2012 |
| JP | 2012223231 A | 11/2012 |
| JP | 05105884 | 12/2012 |
| JP | 5291238 B1 | 6/2013 |
| KR | 20010005620 A | 1/2001 |
| KR | 20020035634 A | 11/2002 |
| KR | 20080028771 A | 1/2008 |
| SE | 9400916 | 3/1994 |
| SE | 9704893 | 12/1997 |
| WO | 9015830 A1 | 12/1990 |
| WO | 9219198 A1 | 11/1992 |
| WO | 9321237 A1 | 10/1993 |
| WO | 9321879 A1 | 11/1993 |
| WO | 9510996 A1 | 4/1995 |
| WO | 9511652 A1 | 5/1995 |
| WO | 9514453 | 6/1995 |
| WO | 9515139 A1 | 6/1995 |
| WO | 9516424 A1 | 6/1995 |
| WO | 9516746 A1 | 6/1995 |
| WO | 9519753 A1 | 7/1995 |
| WO | 9521596 A1 | 8/1995 |
| WO | 9524173 A1 | 9/1995 |
| WO | 9526209 A1 | 10/1995 |
| WO | 9529657 A1 | 11/1995 |
| WO | 9532698 A1 | 12/1995 |
| WO | 9534329 A1 | 12/1995 |
| WO | 9616624 | 6/1996 |
| WO | 9619173 A1 | 6/1996 |
| WO | 96029967 | 10/1996 |
| WO | 9711659 A1 | 4/1997 |
| WO | 9717922 A1 | 5/1997 |
| WO | 9724096 A1 | 7/1997 |
| WO | 9816179 A1 | 4/1998 |
| WO | 9816180 A1 | 4/1998 |
| WO | 9843684 A1 | 10/1998 |
| WO | 9913813 A1 | 3/1999 |
| WO | 9934841 A1 | 7/1999 |
| WO | 9951178 A1 | 10/1999 |
| WO | 200000235 | 1/2000 |
| WO | 200032145 | 6/2000 |
| WO | 200059430 A1 | 10/2000 |
| WO | 200115647 | 3/2001 |
| WO | 200126596 | 4/2001 |
| WO | 0135886 A1 | 5/2001 |
| WO | 200207663 | 1/2002 |
| WO | 200232962 | 4/2002 |
| WO | 02064877 A1 | 8/2002 |
| WO | 02067809 A2 | 9/2002 |
| WO | 2003009794 | 2/2003 |
| WO | 2003039402 | 5/2003 |
| WO | 2003053297 | 7/2003 |
| WO | 03079946 A2 | 10/2003 |
| WO | 03101622 | 12/2003 |
| WO | 2003105738 | 12/2003 |
| WO | 2004021946 A1 | 3/2004 |
| WO | 2004049995 A1 | 6/2004 |
| WO | 2004071539 A3 | 8/2004 |
| WO | 2004084784 A1 | 10/2004 |
| WO | 2004105664 A1 | 12/2004 |
| WO | 2005012406 A1 | 2/2005 |
| WO | 2005018694 A1 | 3/2005 |
| WO | 2005087164 A1 | 9/2005 |
| WO | 2005102237 A1 | 11/2005 |
| WO | 2006038922 A1 | 4/2006 |
| WO | 2006059922 A1 | 6/2006 |

(56) References Cited

FOREIGN PATENT DOCUMENTS

| | | |
|---|---|---|
| WO | 2006062258 A2 | 6/2006 |
| WO | 2006066029 A1 | 6/2006 |
| WO | 2006083584 | 8/2006 |
| WO | 2006104024 A1 | 10/2006 |
| WO | 2006134904 A1 | 12/2006 |
| WO | 2006134906 A1 | 12/2006 |
| WO | 2007000315 A1 | 1/2007 |
| WO | 2007046052 A1 | 4/2007 |
| WO | 2007047598 A1 | 4/2007 |
| WO | 2007049725 A1 | 5/2007 |
| WO | 2007061035 A1 | 5/2007 |
| WO | 2007141744 A1 | 12/2007 |
| WO | 2007142145 A1 | 12/2007 |
| WO | 2007148502 A1 | 12/2007 |
| WO | 2008018922 A1 | 2/2008 |
| WO | 2008065945 A1 | 6/2008 |
| WO | 2008146749 A1 | 12/2008 |
| WO | 2008155699 A1 | 12/2008 |
| WO | 2009004941 A1 | 1/2009 |
| WO | 2009005114 A1 | 1/2009 |
| WO | 2009005431 A1 | 1/2009 |
| WO | 2009011717 A1 | 1/2009 |
| WO | 2009041223 A1 | 4/2009 |
| WO | 2009080611 | 7/2009 |
| WO | 2009096108 A1 | 8/2009 |
| WO | 2009107435 A1 | 9/2009 |
| WO | 2009122830 A1 | 10/2009 |
| WO | 2009139248 A1 | 11/2009 |
| WO | 2009139255 A1 | 11/2009 |
| WO | 2009152018 A1 | 12/2009 |
| WO | 2009155264 | 12/2009 |
| WO | 2009155265 | 12/2009 |
| WO | 2010071508 A1 | 6/2010 |
| WO | 2010074319 A1 | 7/2010 |
| WO | 2010107096 A1 | 9/2010 |
| WO | 2010114052 A1 | 10/2010 |
| WO | 2010117015 A1 | 10/2010 |
| WO | 2010118272 A1 | 10/2010 |
| WO | 201153044 | 5/2011 |
| WO | 2011118725 A1 | 9/2011 |
| WO | 2011118842 A1 | 9/2011 |
| WO | 2011145653 A1 | 11/2011 |
| WO | 2011150955 A1 | 12/2011 |
| WO | 2011163582 A1 | 12/2011 |
| WO | 2012002252 A1 | 1/2012 |
| WO | 2012014436 A1 | 2/2012 |
| WO | 2012017764 A1 | 2/2012 |
| WO | 2012035787 A1 | 3/2012 |
| WO | 2012042908 A1 | 4/2012 |
| WO | 2012043077 A1 | 4/2012 |
| WO | 2012043078 A1 | 4/2012 |
| WO | 2012043082 A1 | 4/2012 |
| WO | 2012052172 A1 | 4/2012 |
| WO | 2012067216 A1 | 5/2012 |
| WO | 2012073499 A1 | 6/2012 |
| WO | 2012074466 A1 | 6/2012 |
| WO | 201291016 | 7/2012 |
| WO | 2012090508 A1 | 7/2012 |
| WO | 2012101934 A1 | 8/2012 |
| WO | 2012102034 A1 | 8/2012 |
| WO | 2012117824 A1 | 9/2012 |
| WO | 2012132460 A1 | 10/2012 |
| WO | 2012170778 A1 | 12/2012 |
| WO | 2012170779 A1 | 12/2012 |
| WO | 2012170781 A1 | 12/2012 |
| WO | 2012170783 A1 | 12/2012 |
| WO | 2012170808 A1 | 12/2012 |
| WO | 2012174026 A1 | 12/2012 |
| WO | 2012177400 A1 | 12/2012 |
| WO | 2013001788 A1 | 1/2013 |
| WO | 2013021651 A1 | 2/2013 |
| WO | 2013046701 A1 | 4/2013 |
| WO | 2013056978 | 4/2013 |
| WO | 2013060733 A1 | 5/2013 |
| WO | 2013077074 A1 | 5/2013 |
| WO | 2013078109 A1 | 5/2013 |
| WO | 2013125216 A1 | 8/2013 |
| WO | 2014004283 A1 | 1/2014 |
| WO | 2014073636 A1 | 5/2014 |
| WO | 2014078247 A2 | 5/2014 |
| WO | 2014093310 A1 | 6/2014 |
| WO | 2014170859 A1 | 10/2014 |
| WO | 2015095514 A3 | 9/2015 |
| WO | 2016040091 A1 | 3/2016 |

OTHER PUBLICATIONS

Extended EP Search Report and Search Opinion for 14168157.7 dated Jun. 17, 2014, 07 pages.
Third Party Opposition for 14168157.7 dated Jun. 17, 2019, 30 pages.
Third Party Opposition for 18159482.1 dated Oct. 4, 2022, 23 pages.
Email exchange in May 2019 with a General Manager Sales &amp; Marketing, Sumitomo Seika Europe S.A./N.V., 2 pages.
Extract from Opposition Division Decision EP2813201, dated Feb. 6, 2020; 8 pages.
Sustainability Report, Edana The Voice of Nonwovens, 4th Edition, 2015, 48 pages.
Test report: Properties of superabsorbent (AGM) materials extracted from commercially marketed absorbent articles—Dr Juliane Kamphus, Jan. 18, 2018; 2 pages.
All Office Actions, U.S. Appl. No. 14/462,621, dated Aug. 19, 2014.
All Office Actions, U.S. Appl. No. 16/159,780, dated Oct. 15, 2018.
PCT Search Report and Written Opinion for PCT/US2014/051584 dated Jul. 10, 2014; 12 Pages.
Extended European Search Report and Search Opinion; Application No. 13185212.1; dated Mar. 21, 2014; 9 pages.
Extended European Search Report and Search Opinion; Application No. 18159482.1; dated May 4, 2018; 11 pages.

* cited by examiner

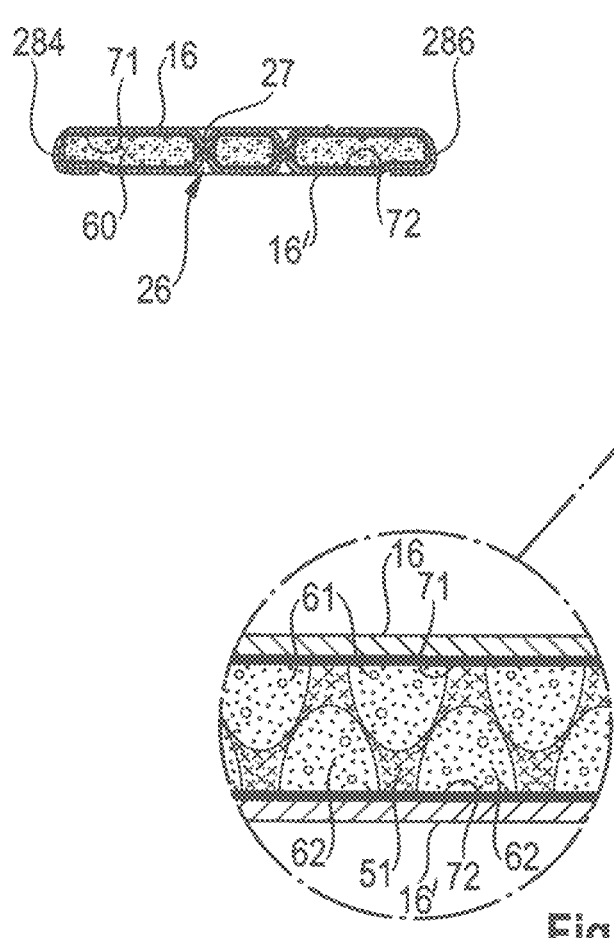
Fig. 2
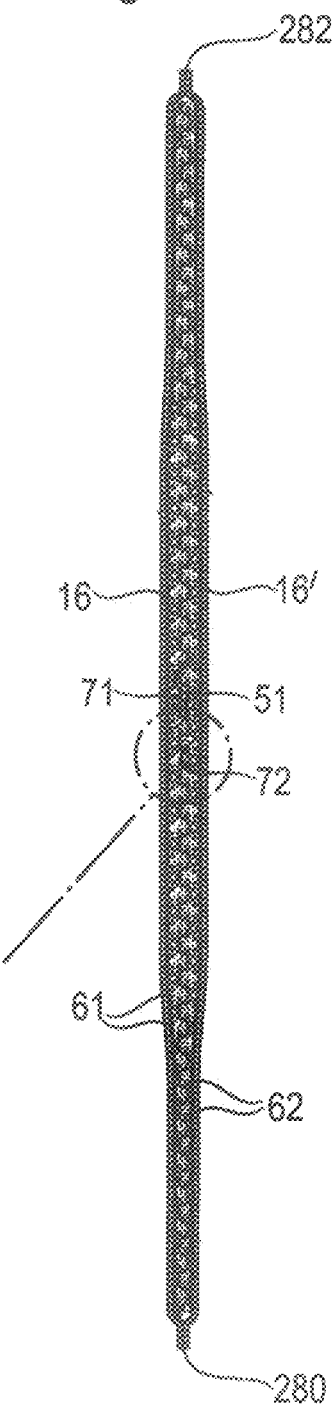
Fig. 3
Fig. 4

Fig. 10
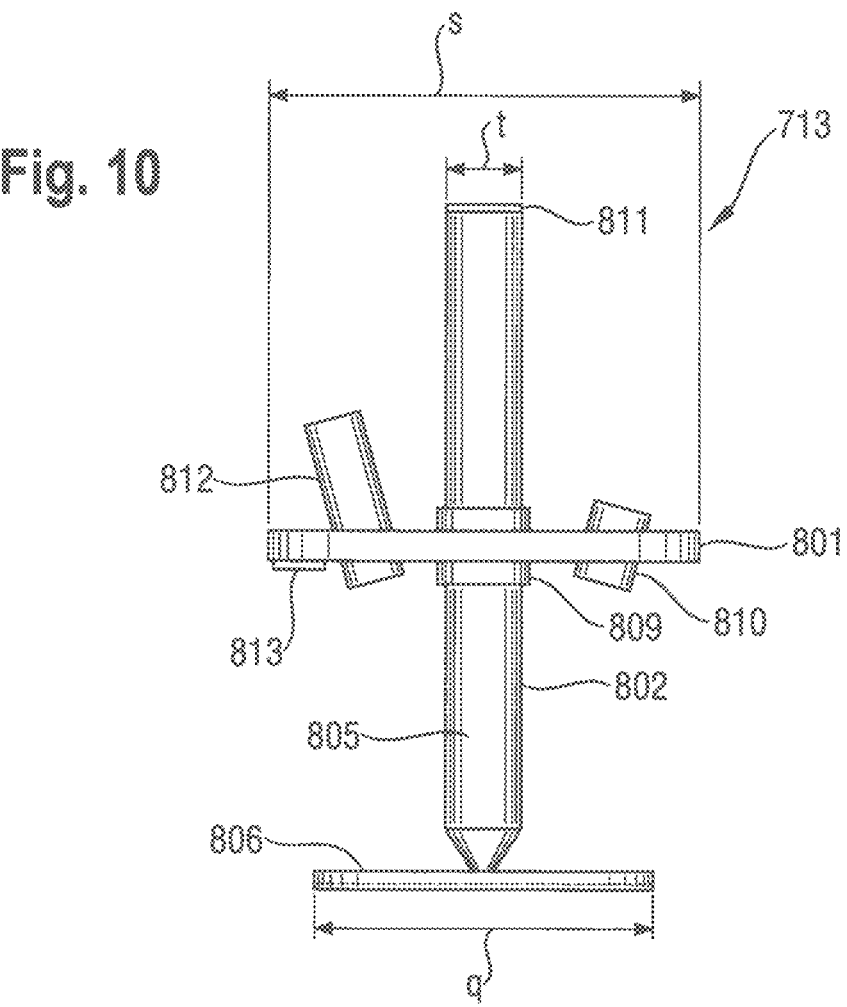
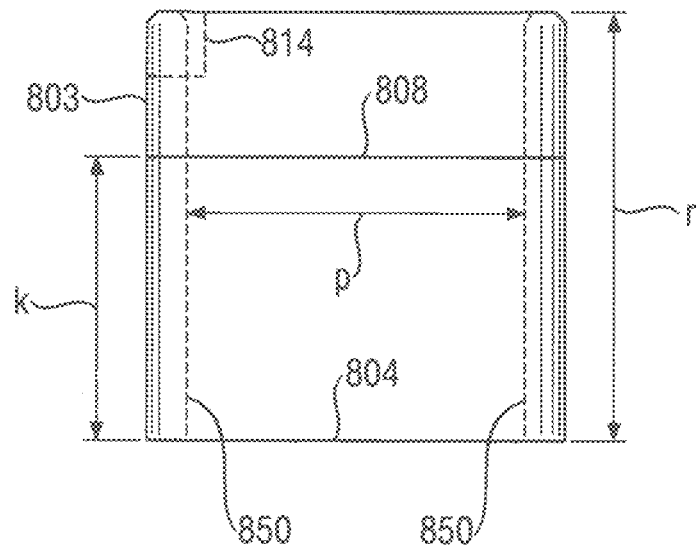

ABSORBENT CORES HAVING MATERIAL FREE AREAS

FIELD OF THE INVENTION

The invention provides absorbent cores for use in absorbent hygiene articles such as, but not limited to, baby diapers, training pants, feminine hygiene sanitary pads and adult incontinence products.

BACKGROUND OF THE INVENTION

Absorbent articles for personal hygiene of the type indicated above are designed to absorb and contain body exudates, in particular large quantity of urine. These absorbent articles comprise several layers providing different functions, for example a topsheet, a backsheet and in-between an absorbent core, among other layers. The function of the absorbent core is typically to absorb and retain the exudates for a prolonged amount of time, minimize re-wet to keep the wearer dry and avoid soiling of clothes or bed sheets.

The majority of currently marketed absorbent articles comprise as absorbent material a blend of comminuted wood pulp with superabsorbent polymers (SAP) in particulate form, also called absorbent gelling materials (AGM), see for example U.S. Pat. No. 5,151,092 (Buell). Absorbent articles having a core consisting essentially of SAP as absorbent material (so called "airfelt-free" cores) have also been proposed (see e.g. WO2008/155699 (Hundorf), WO95/11652 (Tanzer), WO2012/052172 (Van Malderen)). Absorbent cores with slits or grooves have also been proposed, typically to increase the fluid acquisition properties of the core or to act as a folding guide.

WO2012/170778 (Rosati et al., see also WO2012/170779, WO2012/170781 and WO2012/170808) discloses absorbent structures that comprise superabsorbent polymers, optionally a cellulosic material, and at least a pair of substantially longitudinally extending channels. The core wrap can be adhesively bonded through the channels to form a channel bond. The channel bonds may be permanent, so that their integrity is at least partially maintained both in dry and wet state. As the absorbent structure absorbs liquid and swells, the absorbent structure takes a three-dimensional shape with the channels becoming visible. The channels are indicated to provide improved fit and/or better liquid acquisition/transportation, and/or improved performance throughout the use of the absorbent structure. Any superabsorbent polymer particles known from the superabsorbent literature are indicated to be suitable.

The properties of superabsorbent polymers have been characterized in various ways. The absorbent capacity (CRC) in grams of liquid per gram of superabsorbent particles has been used, as well as their absorption speed as measured by the Free Swell Rate (FSR) and their permeability as measured by the Urine Permeability Measurement (UPM) test.

International patent application WO2012/174,026A1 discloses the K(t) method which can be used to determine the time dependent effective permeability (K(t)) and the uptake kinetics (T20) of a gel layer formed from hydrogel-forming superabsorbent polymer particles under a confining pressure. The application indicates that these SAP can be used to reduce leakage, especially at the first gush, i.e. when the article starts to be wetted.

It has now been found that although the absorption properties of conventional SAP may not be negatively impacted at first gush when used in a core with channels, the liquid absorption of the SAP can be significantly reduced in the following gushes after the fluid has been already absorbed in these cores comprising channels compared to cores without channels. Without wishing to be bound by theory, the inventors believe that the three-dimensional channels which are formed as the SAP absorbs a fluid can create a resistance to swelling for the superabsorbent polymers and reduce their swelling kinetics. As the channels otherwise facilitate the distribution of the fluid along the core, it was on contrary expected that any conventional SAP could be used in these cores. Accordingly the inventors have found that for absorbent cores comprising such channels it can be advantageous to use these SAP having a T20 of below 240 s to maintain sufficient speed of absorption beyond first gush.

SUMMARY OF THE INVENTION

The present invention is for absorbent cores as defined in the claims and absorbent articles comprising these absorbent cores. The absorbent cores of the invention comprise in particular a core wrap enclosing an absorbent material comprising superabsorbent polymer particles, wherein the core wrap comprises a top side and a bottom side. The absorbent core comprises one or more area(s) substantially free of absorbent material through which the top side of the core wrap is attached to the bottom side of the core wrap, so that when the absorbent material swells the core wrap forms a channel along each area substantially free of absorbent material. The superabsorbent polymer particles have a time to reach an uptake of 20 g/g (T20) of less than 240 s as measured according to the K(t) test method described herein.

BRIEF DESCRIPTION OF THE DRAWINGS

FIG. 2 is a transversal cross-section of the embodiment of FIG. 1 at the crotch point (C);

FIG. 3 is a longitudinal cross-section of the embodiment of FIG. 1;

FIG. 4 is a close-up view of a part of FIG. 3

FIG. 10 is a cross-sectional side view of a piston/cylinder assembly for use in conducting the Dynamic Effective Permeability and Uptake Kinetics Measurement Test

DETAILED DESCRIPTION OF THE INVENTION

Introduction

Figure 1:
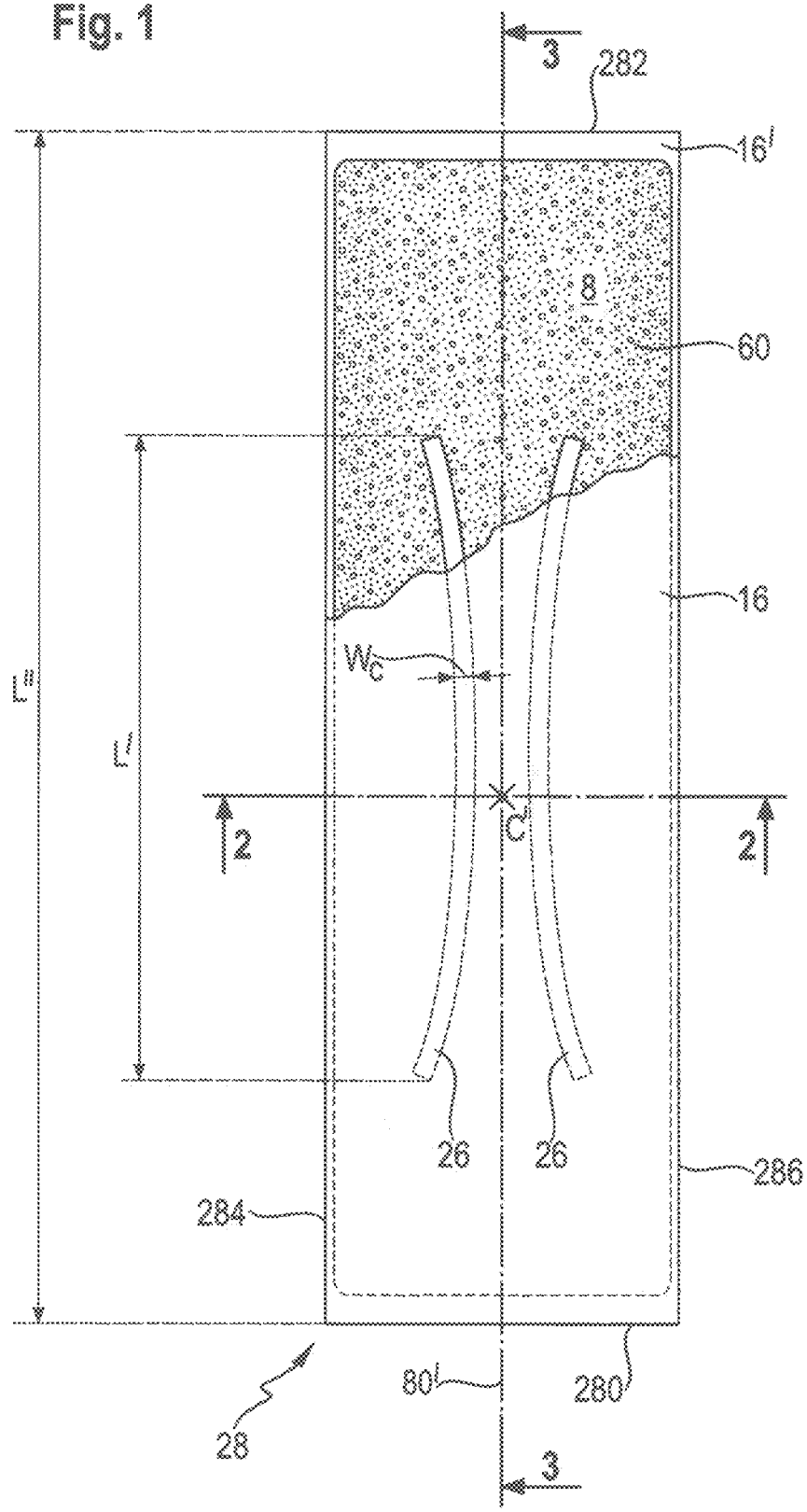
FIG. 1 is a top view of an embodiment of an absorbent core according to the invention with the topside layer of the core wrap partially removed.

As used herein, the term "absorbent articles for personal hygiene" refers to disposable devices such as baby diapers, infant training pants, adult incontinence products or feminine hygiene sanitary pads, and the like which are placed against or in proximity to the body of the wearer to absorb and contain exudates discharged from the body. The absorbent articles of the invention will be further illustrated in the below description and in the Figures in the form of a taped diaper. Nothing in this description should be however considered limiting the scope of the claims unless explicitly indicated otherwise.

A "nonwoven web" as used herein means a manufactured sheet, web or batting of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter ($g/m^2$ or gsm).

The term "joined" or "bonded" or "attached", as used herein, encompasses configurations whereby an element is directly secured to another element by affixing the element directly to the other element e.g. by gluing, and configurations whereby an element is indirectly secured to another element by affixing the element to intermediate member(s) which in turn are affixed to the other element.

"Comprise," "comprising," and "comprises" are open ended terms, each specifies the presence of what follows, e.g., a component, but does not preclude the presence of other features, e.g., elements, steps, components known in the art, or disclosed herein. These terms based on the verb "comprise" should be read as encompassing the narrower terms "consisting of" which excludes any element, step, or ingredient not specified and "consisting essentially of" which limits the scope of an element to the specified materials or steps and those that do not materially affect the way the element performs its function. Any preferred or exemplary embodiments described below are not limiting the scope of the claims, unless specifically indicated to do so. The words "typically", "normally", "advantageously" and the likes also qualify elements which are not intended to limit the scope of the claims unless specifically indicated to do so.

General Description of the Absorbent Core 28

The absorbent core of the invention will be typically made to be used in an absorbent article of the type indicated before. The absorbent core may for example be made on-line and assembled directly with the remaining components of the article or may be off-line at another site and transported to the converting line. It is also possible to use the absorbent core directly as an absorbent article without further assembling of other components for applications which do not require other layers. Typically however the absorbent core will be assembled with other components such as a topsheet and a backsheet to form a finished hygiene article, as will be exemplary described further below for a diaper.

The absorbent core is typically the component of the article having the most absorbent capacity. The absorbent core of the invention comprises a core wrap enclosing an absorbent material, and may also comprise at least one adhesive. The absorbent material comprises a superabsorbent polymer in particulate forms (herein abbreviated as "SAP"). The absorbent material may comprise relatively high amount of SAP enclosed within the core wrap. By "absorbent material" it is meant a material which has some absorbency property or liquid retaining properties, such as SAP, cellulosic fibers as well as synthetic fibers. Typically, adhesives used in making absorbent cores have no absorbency properties and are not considered as absorbent material.

The SAP content may represent at least 70% or more (in particular at least 80%, at least 85%, at least 90%, at least 95% and up to 100%) by weight of the absorbent material enclosed in the core wrap. The core wrap itself is not considered as absorbent material for the purpose of assessing the percentage of SAP in the absorbent core. High amount of SAP provides a relatively thin core compared to conventional core typically comprising between 40-60% by weight of cellulose fibers. The absorbent core may be thin, for example having a thickness not exceeding 5 mm, e.g. from 0.2 mm to 4 mm, in particular from 0.5 to 3 mm, as measured with the Dry Absorbent Core Caliper Test disclosed therein.

An exemplary absorbent core 28 of the invention is shown in isolation in FIGS. 1-4 and will now be further described. The absorbent core shown and its description are purely for exemplary purpose and are not intended to limit the scope of the claims, unless otherwise stated. The absorbent core typically comprises a front side 280, a back side 282 and two longitudinal sides 284, 286 joining the front side 280 and the back side 282. The absorbent core also comprises a generally planar top side 16 and a generally planar bottom side 16' formed by the core wrap. The front side 280 of the core is the side of the core intended to be placed towards the front edge 10 of the absorbent article. The core may have a longitudinal axis 80' corresponding substantially to the longitudinal axis of the article 80, as seen from the top in a planar view as in FIG. 1. Typically the absorbent material will be advantageously distributed in higher amount towards the front side and middle portion of the core than towards the back side as more absorbency is required at the front. Typically the front and back sides of the core are shorter than the longitudinal sides of the core. The core wrap may be formed by two nonwoven material which may be at least partially sealed along the sides of the absorbent core. The first nonwoven may substantially form the whole of the top side of the core wrap and the second nonwoven substantially the whole of the bottom side 16' of the core wrap. The top side and first nonwoven are represented by the same number 16 on the drawings, the bottom side and the second nonwoven by number 16'. The core wrap may be at least partially sealed along its front side, back side and/or two longitudinal sides to improve the containment of the absorbent material during use.

The absorbent material may in particular comprises less than 10% weight percent of natural or synthetic fibers, or less than 5% weight percent, or even be substantially free of natural and/or synthetic fibers. The absorbent material may advantageously comprise little or no airfelt (cellulose) fibers, in particular the absorbent core may comprise less than 15%, 10%, 5% airfelt (cellulose) fibers by weight of the absorbent core, or even be substantially free of cellulose fibers.

Various absorbent core designs comprising high amount of SAP have been proposed in the past, see for example in U.S. Pat. No. 5,599,335 (Goldman), EP1,447,066 (Busam), WO95/11652 (Tanzer), US2008/0312622A1 (Hundorf), WO2012/052172 (Van Malderen) and WO2012/170778 (Rosati et al., see also WO2012/170779, WO2012/170781 and WO2012/170808).

The absorbent core 28 comprises at least one area 26 which is substantially free of absorbent material and through which the top side of the core wrap is attached to the bottom side of the core wrap. When the absorbent material absorbs a liquid, it swells in proportion and the core wrap gradually forms a channel 26' along the bonded area 26 substantially free of absorbent material.

The length L" of the absorbent core as measured along it axis 80' from the front side 280 to the back side 282 should be adapted for the intended article in which it will be used. For infant diapers, the length L" may for example range from 5 to 40 cm. The absorbent core comprises a crotch point C' defined as the point on the longitudinal axis 80' situated at a distance of two fifth (⅖) of L" starting from the front side 280 of the absorbent core. The individual components of the absorbent core will now be described in further details.

Core Wrap (16, 16')

The function of the core wrap is to enclose the absorbent material. Typical core wraps comprise two substrates 16, 16' which are attached to another, but the core wrap may also be made of a single substrate folded around the absorbent material, or may comprises several substrates. When two substrates are used, these may be typically attached to another along at least part of the periphery of the absorbent core. Typical attachments are the so-called C-wrap and sandwich wrap. In a C-wrap, as exemplarily shown in FIG. 2, the longitudinal and/or transversal edges of one of the substrate are folded over the other substrate to form flaps. These flaps are then bonded to the external surface of the other substrate, typically by gluing. In a sandwich wrap, as shown on FIG. 3, the edges of both substrates are attached, e.g. by gluing, to another in a flat configuration.

The core wrap may be formed by any materials suitable for enclosing the absorbent material. Typical substrate materials used in the production of conventional cores may be used, in particular nonwovens but also paper, tissues, films, wovens, or laminate of any of these. The core wrap may in particular be formed by a nonwoven web, such as a carded nonwoven, a spunbond nonwoven ("S") or a meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US2011/0268932A1, US2011/0319848A1 or US2011/0250413A1. Nonwoven materials provided from synthetic fibers may be used, such as PE, PET and in particular PP.

If the core wrap comprises a first substrate 16 and a second substrate 16' these may be made of the same type of material, or may be made of different materials or one of the substrate may be treated differently than the other to provide it with different properties. As the polymers used for nonwoven production are inherently hydrophobic, they are preferably coated with hydrophilic coatings if placed on the fluid receiving side of the absorbent core. It is advantageous that the top side 16 of the core wrap, i.e. the side placed closer to the wearer in the absorbent article, be more hydrophilic than the bottom side 16' of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g. as described in WO 02/064877.

Permanently hydrophilic nonwovens are also useful in some embodiments. Surface tension can be used to measure how permanently a certain hydrophilicity level is achieved. Liquid strike through can be used to measure the hydrophilicity level. The first and/or second substrate may in particular have a surface tension of at least 55, preferably at least 60 and most preferably at least 65 mN/m or higher when being wetted with saline solution. The substrate may also have a liquid strike through time of less than 5 seconds for a fifth gush of liquid. These values can be measured using the test methods described in U.S. Pat. No. 7,744,576B2 (Busam et al.): "Determination Of Surface Tension" and "Determination of Strike Through" respectively.

Hydrophilicity and wettability are typically defined in terms of contact angle and the strike through time of the fluids, for example through a nonwoven fabric. This is discussed in detail in the American Chemical Society publication entitled "Contact angle, wettability and adhesion", edited by Robert F. Gould (Copyright 1964). A substrate having a lower contact angle between the water and the surface of substrate may be said to be more hydrophilic than another.

The substrates may also be air-permeable. Films useful herein may therefore comprise micro-pores. The substrate may have for example an air-permeability of from 40 or from 50, to 300 or to 200 $m^3/(m^2 \times min)$, as determined by EDANA method 140-1-99 (125 Pa, 38.3 $cm^2$). The material of the core wrap may alternatively have a lower air-permeability, e.g. being non-air-permeable, for example to facilitate handling on a moving surface comprising vacuum.

The core wrap may be sealed along its longitudinal edges and/or its transversal edges. In a C-wrap configuration, for example, a first substrate 16 may be placed on one side of the core and extends around the core's longitudinal edges to partially wrap the opposed bottom side of the core (see FIG. 2). The second substrate 16' is typically present between the wrapped flaps of the first substrate 16 and the absorbent material 60. The flaps of the first substrate 16 may be glued to the second substrate 16' to provide a strong seal. This so called C-wrap construction can provide benefits such as improved resistance to bursting in a wet loaded state compared to a sandwich seal. The front side and back side of the core wrap may then also be sealed for example by gluing the first substrate and second substrate to another to provide complete enclosing of the absorbent material across the whole of the periphery of the core. For the front side and back side of the core the first and second substrate may extend and be joined together in a substantially planar direction, forming for these edges a so-called sandwich construction. In the so-called sandwich construction, the first and second substrates may also extend outwardly on all sides of the core and be sealed flat along the whole or parts of the periphery of the core typically by gluing and/or heat/pressure bonding. Typically neither first nor second substrates need to be shaped, so that they can be rectangularly cut for ease of production but of course other shapes are possible.

The terms "seal" and "enclosing" are to be understood in a broad sense. The seal does not need to be continuous along the whole periphery of the core wrap but may be discontinuous along part or the whole of it, such as formed by a series of seal points spaced on a line. Typically a seal may be formed by gluing and/or thermal bonding. The core wrap may also be formed by a single substrate which may enclose the absorbent material as in a parcel wrap and be for example sealed along the front side and back side of the core and one longitudinal seal.

Absorbent Material 60

The absorbent core 28 comprises an absorbent material 60 comprising superabsorbent polymer particles ("SAP"). The absorbent material may be for example applied as a continuous layer. The absorbent material may also be comprised of individual pockets or stripes of absorbent material enclosed within the core wrap. A continuous layer of absorbent material, in particular of SAP, may also be obtained by combining two absorbent layers having matching discontinuous absorbent material application pattern wherein the resulting layer is substantially continuously distributed across the absorbent particulate polymer material area, as taught in US2008/0312622A1 (Hundorf) for example. In this way, each absorbent material layer comprises a pattern having absorbent material areas and absorbent material-free areas, wherein the absorbent material areas of the first layer correspond substantially to the absorbent material-free areas of the second layer and vice versa. A microfibrous glue 51 as disclosed further below may be applied on each absorbent material layer to immobilize it on each substrate. As exemplary shown in FIGS. 3-4, the absorbent core 28 may thus comprise a first absorbent layer and a second absorbent layer, the first absorbent layer comprising a first substrate 16 and a first layer 61 of absorbent material, which may be 100% SAP, and the second absorbent layer comprising a second substrate 16' and a second layer 62 of absorbent material, which may also be 100% SAP. The first and second SAP layers may be applied as transversal stripes or "land areas" having the same width as the desired absorbent material deposition area 8 on their respective substrate before being combined. The stripes may advantageously comprise different amount of absorbent material to provide a profiled basis weight along the longitudinal axis and/or transversal axis of the core 80'. The first substrate 16 and the second substrate 16' may form the core wrap. An auxiliary glue 71, 72 may be applied between one or both substrates and the absorbent layers, as well as microfiber glue on each absorbent layer.

Superabsorbent Polymer Particles (SAP)

"Superabsorbent polymers" as used herein refer to absorbent material which are cross-linked polymeric materials that can absorb at least 10 times their weight of an aqueous 0.9% saline solution as measured using the Centrifuge Retention Capacity (CRC) test (EDANA method WSP 241.2-05E). These polymers are typically used in particulate forms ("SAP") so as to be flowable in the dry state. The term "particles" refers to granules, fibers, flakes, spheres, powders, platelets and other shapes and forms known to persons skilled in the art of superabsorbent polymer particles.

Typical particulate absorbent polymer materials are made of poly(meth)acrylic acid polymers. However, e.g. starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. The superabsorbent polymers can be internally cross-linked, i.e. the polymerization is carried out in the presence of compounds having two or more polymerizable groups which can be free-radically copolymerized into the polymer network. Exemplary superabsorbent polymer particles of the prior art are for example described in WO2006/083584, WO2007/047598, WO2007/046052, WO2009/155265, WO2009/155264.

Although it can be expected that SAP should experience a reduction in absorption speed beyond the first gush as the core becomes loaded, the inventors have found that this reduction was significantly more important in a core comprising channels compared to a similar core without channels. The present invention uses SAP having a time to reach an uptake of 20 g/g (T20) of less than 240 s as measured by the K(t) test method described in WO2012/174026A1 to solve this problem. The SAP may in particular have a T20 of less than 220 s, or less than 200 s, or less than 180 s, or less than 160 s. The time T20 may also be in particular of at least of 40 s, 60 s, 80 s, 100 s, 120 s or 140 s and any combinations of these values to form a range, e.g. of from 100 s to 200 s. WO2012/174,026A1 describes SAP having these properties and the method used to measure these parameters. An equipment used for this method is called 'Zeitabhängiger Durchlässigkeitsprüfstand' or 'Time Dependent Permeability Tester', Equipment No. 03-080578 and is commercially available at BRAUN GmbH, Frankfurter Str. 145, 61476 Kronberg, Germany and is detailed in the above mentioned application. Upon request, operating instructions, wiring diagrams and detailed technical drawings are also available.

The K(t) method is also useful to determine other SAP parameters, which may also be advantageously used in the present invention. The uptake of the SAP at 20 min (U20) may be in particular of at least 22 g/g, or at least 24 g/g, or at least 28 g/g or at least 30 g/g, or of from 28 g/g to 60 g/g, or of from 30 g/g to 50 g/g, or of from 30 g/g to 40 g/g as measured according to the K(t) test method disclosed in WO2012/174,026A1. The SAP may have an effective permeability at 20 minutes (K20) of at least $5\cdot10^{-8}$ cm$^2$, or at least $7\cdot10^{-8}$ cm$^2$, or at least $8.5\cdot10^{-8}$ cm$^2$, or of $5\cdot10^{-8}$ cm$^2$ to $1\cdot10^{-6}$ cm$^2$, or of $7\cdot10^{-8}$ cm$^2$ to $5\cdot10^{-7}$ cm$^2$, or of $8.5\cdot10^{-8}$ to $1\cdot10^{-7}$ cm$^2$ as measured according to the K(t) test method.

The SAP may also have a ratio between the minimum effective permeability and the permeability at 20 minutes (Kmin/K20 ratio) of more than 0.75, or more than 0.8 or more than 0.9 as measured according to the K(t) test method. In such embodiments the transient gel blocking is minimum and the liquid exudates are able to travel fast through the void spaces present between the particles throughout all the swelling process and especially in the initial part of the swelling phase which is the most critical for the first gush.

For embodiments having more than one type of superabsorbent polymer particles, the K(t) test method is carried out on a mixture of the more than one type of superabsorbent polymer particles present in their respective proportion as used in the absorbent core.

The superabsorbent polymer particles may further have a permeability at equilibrium expressed as UPM (Urine Permeability Measurement) value of more than 40, or preferably more than 50, or more than 60, or of 50 to 500, or of 55 to 200, or of 60 to 150 UPM units, where 1 UPM unit is $1\times10^{-7}$ (cm$^3\cdot$s)/g. The UPM value is measured according to the UPM Test method set out in WO2012/174,026A1. This method is closely related to the SFC test method of the prior art. The UPM Test method typically measures the flow resistance of a preswollen layer of superabsorbent polymer particles, i.e. the flow resistance is measured at equilibrium. Therefore, such superabsorbent polymer particles having a high UPM value exhibit a high permeability when a significant volume of the absorbent article is already wetted by the liquid exudates. These embodiments exhibit good absorption properties not only at the first gush but also at the subsequent gushes.

The SAP used may also have a FSR (Free Swell Rate) of more than 0.1 g/g/s, or of from 0.1 to 2 g/g/s, or 0.3 to 1 g/g/s, or 0.3 to 0.6 g/g/s, or 0.4 to 0.6 g/g/s. The Free Swell Rate of the SAP is measured according to the FSR test method set out in WO2012/174,026A1. SAP having high free swell rate values will be able to absorb liquid quickly under no confining pressure. Contrary to the K(t) test method, no external pressure is applied to the gel bed in order to measure the free swell rate. SAP having a too low FSR value may require more than 240 s to reach an uptake of 20 g/g as measured according to the K(t) test method of the present invention and will consequently not be able to absorb the liquid exudates as fast as necessary. However, as stated above, superabsorbent polymer particles having a high FSR value do not automatically lead to high uptake values as measured according to the K(t) test method.

The SAP may have a CRC (centrifuge retention capacity) value of more than 18 g/g, or more than 20 g/g, or more than 22 g/g, or more than 24 g/g, for example up to 50 g/g, or up to 40 g/g, or to 30 g/g, as measured according to EDANA method WSP 241.2-05. The CRC measures the liquid absorbed by the superabsorbent polymer particles for free swelling in excess liquid. Superabsorbent polymer particles having a high CRC value may be preferred since less superabsorbent polymer particles are needed to facilitate a required overall capacity for liquid absorption.

At least some of the superabsorbent polymers may be present in the form of agglomerated superabsorbent polymer particles. Agglomerated superabsorbent polymer particles comprise agglomerated precursor particles having a first mass average particle size, and wherein the agglomerated superabsorbent polymer particles have a second mass average particle size which is at least 25% greater than the first mass average particle size. The second mass average particle size may be at least 30%, or at least 40% or at least 50% higher than the first mass average particle size. Mass average particle size may be measured according to Mass Average Particle Size Sieve Test method described below.

The agglomerated superabsorbent polymer particles may be obtained by various methods. Agglomerated particles may be for example obtained by aggregating the precursor particles with an interparticle crosslinking agent reacted with the polymer material of the precursor particles to form crosslink bonds between the precursor particles have been for example disclosed in U.S. Pat. Nos. 5,300,565, 5,180, 622, (both to Berg), U.S. Pat. Nos. 5,149,334, 5,102,597 (both to Roe), U.S. Pat. No. 5,492,962 (Lahrman). Agglomerated superabsorbent polymer particles may also be obtained by a method comprising the steps of providing superabsorbent polymer particles and mixing the superabsorbent polymer particles with a solution comprising water and a multivalent salt having a valence of three or higher. This method is further disclosed in co-pending application number EP14168064.

The superabsorbent polymer particles of the core of the invention may in particular comprise at least 10%, or at least 20% or at least 30% or at least 50% by weight of the agglomerated superabsorbent polymer particles The total amount of SAP present in the absorbent core may also vary according to expected user of the article. Diapers for newborns require less SAP than infant or adult incontinence diapers. The amount of SAP in the core may be for example comprised from about 2 to 50 g, in particular from 5 to 40 g for typical enfant diapers. The average SAP basis weight within the (or "at least one", if several are present) deposition area 8 of the SAP may be for example of at least 50, 100, 200, 300, 400, 500 or more g/m². The material free areas 26 present in the absorbent material deposition area 8 are deduced from the absorbent material deposition area to calculate this average basis weight.

Area(s) 26 Substantially Free of Absorbent Material and Channels 26'

The absorbent core 28 comprises one or more area(s) 26 which is/are substantially free of absorbent material. By "substantially free" it is meant that in each of these areas the basis weight of the absorbent material is at least less than 25%, in particular less than 20%, less than 10%, of the average basis weight of the absorbent material in the rest of the core. In particular there can be no absorbent material in these areas. Minimal amount such as involuntary contaminations with absorbent material that may occur during the making process are not considered as absorbent material. The areas 26 are advantageously surrounded by the absorbent material, when seen in the plane of the core, which means that the area(s) 26 does not extend to any of the edge of the deposition area 8 of the absorbent material.

Figure 7:
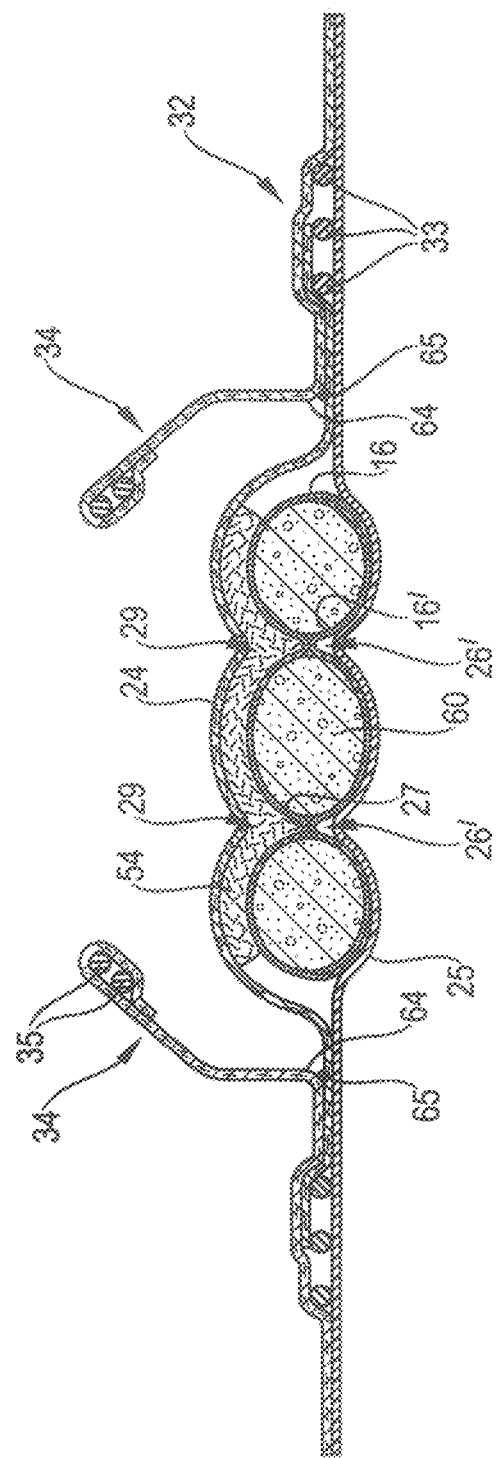
FIG. 7 is a transversal cross-section of the article taken at the same point as FIG. 6 where channels have formed in the core as a result of the diaper being loaded with fluid.

The top side 16 of the core wrap is attached to the bottom side 16' of the core wrap by core wrap bond(s) 27 through these area(s) 26 substantially free of absorbent material. As shown in FIG. 7, when the absorbent material swells upon absorbing a liquid, the core wrap bond remains at least initially attached in the substantially material free area(s) 26. The absorbent material swells in the rest of the core when it absorbs a liquid, so that the core wrap forms one or more channel(s) 26' along the area(s) 26 substantially free of absorbent material comprising the core wrap bond 27. These channels 26' are three dimensional and can serve to distribute an insulting fluid along their length to a wider area of the core. This may provide a quicker fluid acquisition speed and a better utilization of the absorbent capacity of the core. The channels 26' can also provide a deformation of an overlying layer such as a fibrous layer 54 and provide corresponding ditches 29 in the overlying layer. It is not excluded that the absorbent core may comprise other area(s) substantially free of absorbent material but without a core wrap bond, but these non-bonded areas will typically not form a channel when wet.

The top side 16 and the bottom side 16' of the core wrap may be attached together continuously along the area(s) 26 substantially free of absorbent material, but the core wrap bond 27 may also be discontinuous (intermittent) such as series of point bonds. Typically, an adhesive can be used to attach the top side to the bottom of the core wrap, but it is possible to bond via other known attachment means, such as pressure bonding, ultrasonic bonding or heat bonding or combination thereof. The attachment of the top side and bottom side of the core wrap may be provided by one or more adhesive material, in particular one or more layers of auxiliary glue 71, 72 and/or one or more layers of fibrous adhesive material 51, if present in the core, as indicated below. These glues may therefore serve the dual function of immobilizing the absorbent material and attach the top side and the bottom side of the core together.

The following examples of the shape and size of the areas 26 substantially free of absorbent material are not limiting. In general, the core wrap bond 27 may have the same outline but be slightly smaller than the areas 26 due to the tolerance required in some manufacturing process. The substantially material free area(s) 26 may be present within the crotch region of the article, in particular at least at the same longitudinal level as the crotch point C', as represented in FIG. 1 by the two longitudinally extending areas substantially free of absorbent material 26. The absorbent core 28 may also comprise more than two substantially absorbent material free area(s), for example at least 3, or at least 4 or at least 5 or at least 6. The absorbent core may comprise one or more pairs of areas substantially free of absorbent material symmetrically arranged relative to the longitudinal axis 80'. Shorter area(s) substantially free of absorbent material may also be present, for example in the back region or the front region of the core, as seen for example in the Figures of WO2012/170778.

The area(s) 26 substantially free of absorbent material may extend substantially longitudinally, which means typically that each area extends more in the longitudinal direction than in the transverse direction, and typically at least twice as much in the longitudinal direction than in the transverse direction (as measured after projection on the respective axis). The area(s) 26 substantially free of absorbent material may have a length L' projected on the longitudinal axis 80' of the core that is at least 10% of the length L" of the absorbent core, in particular from 20% to 80%. It may be advantageous that at least some or all of the area(s) 26 are not completely or substantially completely transversely oriented channels in the core.

The area(s) 26 substantially free of absorbent material may be completely oriented longitudinally and parallel to the longitudinal axis but also may be curved. In particular some or all these area(s), in particular these area(s) present in the crotch region, may be concave towards the longitudinal axis 80', as for example represented in FIG. 1 for the pair of channels 26'. The radius of curvature may typically be at least equal (and preferably at least 1.5 or at least 2.0 times this average transverse dimension) to the average transverse dimension of the absorbent material deposition area 8; and also straight but under an angle of (e.g. from 5°) up to 30°, or for example up to 20°, or up to 10° with a line parallel to the longitudinal axis. The radius of curvature may be constant for a substantially absorbent material free area(s), or may vary along its length. This may also includes area(s) substantially free of absorbent material with an angle therein, provided said angle between two parts of a channel is at least 120°, preferably at least 150°; and in any of these cases, provided the longitudinal extension of the area is more than the transverse extension. These area(s) may also be branched, for example a central substantially material free area superposed with the longitudinal axis in the crotch region which branches towards the back and/or towards the front of the article.

In some embodiments, there is no area(s) substantially free of absorbent material that coincides with the longitudinal axis 80' of the core. When present as one ore symmetrical pair(s) relative to the longitudinal axis, the area(s) substantially free of absorbent material may be spaced apart from one another over their whole longitudinal dimension. The smallest spacing distance may be for example at least 5 mm, or at least 10 mm, or at least 16 mm.

Furthermore, in order to reduce the risk of fluid leakages, the area(s) substantially free of absorbent material may advantageously not extend up to any of the edges of the absorbent material deposition area 8, and are therefore surrounded by and fully encompassed within the absorbent material deposition area 8 of the core. Typically, the smallest distance between an area(s) substantially free of absorbent material and the closest edge of the absorbent material deposition area is at least 5 mm.

The area(s) substantially free of absorbent material may have a width Wc along at least part of its length which is at least 2 mm, or at least 3 mm or at least 4 mm, up to for example 20 mm, or 16 mm or 12 mm. The width Wc of the area(s) substantially free of absorbent material may be constant through substantially its whole length or may vary along its length.

The channels 26' in the absorbent core start forming when the absorbent material absorbs a liquid such as urine and starts swelling. As the core absorbs more liquid, the depressions within the absorbent core formed by channels will become deeper and more apparent to the eye and the touch. It is possible to create a sufficiently strong core wrap bond combined with a relatively low amount of SAP so that the channels remain permanent until complete saturation of the absorbent material. On the other hand, the core wrap bonds may in some cases also restrict the swelling of the absorbent material when the core is substantially loaded. The inventors have thus found that the core wrap bond 27 may also be designed to open in a controlled manner when exposed to a large amount of fluid. The bonds may thus remain substantially intact at least during a first phase as the absorbent material absorbs a moderate quantity of fluid. In a second phase the core wrap bonds 27 in the channels can start opening to provide more space for the absorbent material to swell while keeping most of the benefits of the channels such as increased flexibility of the core in transversal direction and fluid management. In a third phase, corresponding to a very high saturation of the absorbent core, a more substantial part of the channel bonds can open to provide even more space for the swelling absorbent material to expand. The strength of core wrap bond 27 within the channels can be controlled for example by varying the amount and nature of the glue used for the attaching the two sides of the core wrap, the pressure used to make the core wrap bond and/or the distribution of the absorbent material, as more absorbent material will usually causes more swelling and will put more pressure on the bond. The extensibility of the material of the core wrap may also play a role.

Absorbent Material Deposition Area 8

The absorbent material deposition area 8 can be defined by the periphery of the layer formed by the absorbent material 60 within the core wrap, as seen from the top side of the absorbent core. The absorbent material deposition area 8 can be generally rectangular, for example as shown in FIG. 1, but other shapes can also be used such as a "T" or "Y" or "sand-hour" or "dog-bone" shape. In particular the deposition area may which show a tapering along its width towards the middle or "crotch" region of the core. In this way, the absorbent material deposition area may have a relatively narrow width in an area of the core intended to be placed in the crotch region of the absorbent article. This may provide for example better wearing comfort. The absorbent material deposition area 8 may thus have a width (as measured in the transversal direction) at its narrowest point which is less than about 100 mm, 90 mm, 80 mm, 70 mm, 60 mm or even less than about 50 mm. This narrowest width may further be for example at least 5 mm, or at least 10 mm, smaller than the width of the deposition area at its largest point in the front and/or back regions of the deposition area 8.

The basis weight (amount deposited per unit of surface) of the SAP may also be varied along the deposition area 8 to create a profiled distribution of absorbent material, in particular SAP, in the longitudinal direction (as shown in FIG. 3), in the transversal direction, or both directions of the core. Hence along the longitudinal axis of the core, the basis weight of absorbent material may vary, as well as along the transversal axis, or any axis parallel to any of these axes. The basis weight of SAP in area of relatively high basis weight may thus be for example at least 10%, or 20%, or 30%, or 40%, or 50% higher than in an area of relatively low basis weight. In particular the SAP present in the absorbent material deposition area at the longitudinal position of the crotch point C' may have more SAP per unit of surface deposited as compared to another area of the absorbent material deposition area 8.

The absorbent material may be deposited using known techniques, which may allow relatively precise deposition of SAP at relatively high speed. In particular the SAP printing technology as disclosed for example in US2006/024433 (Blessing), US2008/0312617 and US2010/0051166A1 (both to Hundorf et al.) may be used. This technique uses a transfer device such as a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate in particular to provide one or more area(s) 26 substantially free of absorbent material surrounded by absorbent material. The areas substantially free of absorbent material can be formed for example by modifying the pattern of the grid and receiving drums so that no SAP is applied in the selected areas, as exemplary disclosed in US2012/0312491 (Jackels).

Microfiber Glue 51

The absorbent core may also comprise a fibrous thermoplastic adhesive material 51, in particular a microfiber glue, to further immobilize the absorbent material within the core. The fibrous thermoplastic adhesive material 51 may be useful to immobilize the layer of absorbent materials 61, 62 to their respective substrate, in particular when the absorbent layer(s) comprises land areas separated by junction areas. The fibrous thermoplastic adhesive material 51 may then be at least partially in contact with the absorbent material 61, 62 in the land areas and at least partially in contact with the substrate layer 16, 16' in the junction areas. This imparts an essentially three-dimensional net-like structure to the fibrous layer of thermoplastic adhesive material 51, which in itself is essentially a two-dimensional structure of relatively small thickness, as compared to the dimension in length and width directions. Thereby, the fibrous thermoplastic adhesive material may provide cavities to cover the absorbent material in the land areas, and thereby immobilizes this absorbent material. The microfiber glue 51 may be for example applied by spraying each absorbent layer.

The thermoplastic polymer may typically have a molecular weight (Mw) of more than 10,000 and a glass transition temperature (Tg) usually below room temperature or $-6°$ C.$<$Tg$<16°$ C. Typical concentrations of the polymer in a hotmelt are in the range of about 20 to about 40% by weight. The thermoplastic polymers may be water insensitive. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

The tackifying resin may exemplarily have a Mw below 5,000 and a Tg usually above room temperature, typical concentrations of the resin in a hotmelt are in the range of about 30 to about 60%, and the plasticizer has a low Mw of typically less than 1,000 and a Tg below room temperature, with a typical concentration of about 0 to about 15%.

The thermoplastic adhesive used for the fibrous layer preferably has elastomeric properties, such that the web formed by the fibers on the SAP layer is able to be stretched as the SAP swell. Exemplary elastomeric, hotmelt adhesives include thermoplastic elastomers such as ethylene vinyl acetates, polyurethanes, polyolefin blends of a hard component (generally a crystalline polyolefin such as polypropylene or polyethylene) and a Soft component (such as ethylene-propylene rubber); copolyesters such as poly (ethylene terephthalate-co-ethylene azelate); and thermoplastic elastomeric block copolymers having thermoplastic end blocks and rubbery mid blocks designated as A-B-A block copolymers: mixtures of structurally different homopolymers or copolymers, e.g., a mixture of polyethylene or polystyrene with an A-B-A block copolymer; mixtures of a thermoplastic elastomer and a low molecular weight resin modifier, e.g., a mixture of a styrene-isoprenestyrene block copolymer with polystyrene; and the elastomeric, hot-melt, pressure-sensitive adhesives described herein. Elastomeric, hot-melt adhesives of these types are described in more detail in U.S. Pat. No. 4,731,066 (Korpman).

The thermoplastic adhesive material 51 fibers may exemplarily have an average thickness of about 1 to about 50 micrometers or about 1 to about 35 micrometers and an average length of about 5 mm to about 50 mm or about 5 mm to about 30 mm. To improve the adhesion of the thermoplastic adhesive material to the substrate or to any other layer, in particular any other nonwoven layer, such layers may be pre-treated with an auxiliary adhesive. The fibers adhere to each other to form a fibrous layer, which can also be described as a mesh.

The absorbent core advantageously achieve an SAP loss of no more than about 70%, 60%, 50%, 40%, 30%, 20%, 10% according to the Wet Immobilization Test described in US2010/0051166A1.

Auxiliary Glue 71, 72

The absorbent core of the invention may further comprise an auxiliary glue present on the inner surface of the top side and/or bottom side of the absorbent core, in particular to help immobilizing the SAP within the core wrap, to ensure integrity of the core wrap and/or to form the bond 27 attaching the bottom side of the core wrap to the top side of the core wrap through the one or more area(s) substantially free of absorbent material.

This so-called auxiliary glue 71, 72 can be applied on the inner surface of the top side and/or the bottom side of the core wrap. The auxiliary glue may be any conventional glue used in the field, in particular hotmelt glue. Example of glues are based on an adhesive polymer such SIS (Styrene-Isoprene-Block Co-Polymer), SBS (Styrene-Butadiene-Block Co-polymer) or mPO (metalocine Polyolefine). The glue may also comprise a tackifier such as a hydrogenated hydrocarbon resin, as well as an oil and an antioxidant. Hydrogenated hydrocarbon resins are made from mixed aromatic/aliphatic resins which are subsequently selectively hydrogenated to produce a wide range of materials with low color, high stability and broad compatibility. Examples of commercially available adhesives are available as HL1358L0 and NW1286 (both from HB Fuller) and DM 526 (from Henkel).

The auxiliary glue may be applied on the top side and/or the bottom side of the core wrap in an average amount ranging from 2 gsm to 20 gsm, more particularly from 4 gsm to 10 gsm. The auxiliary glue may be uniformly applied, or discontinuously, in particular as a series of stripes regularly spaced and longitudinally oriented, for example a series of auxiliary glue stripes of about 1 mm width spaced from each other by a distance raging from 1 mm to 3 mm. The auxiliary glue may help forming the core wrap bond 27 if sufficient pressure and glue is applied within the material free area 26 to attach both sides of the core wrap. The auxiliary glue layer may be applied to the inner surface of the bottom side, the inner surface of the top side, or both inner surfaces of the core wrap.

General Description of the Absorbent Article

Figure 5:
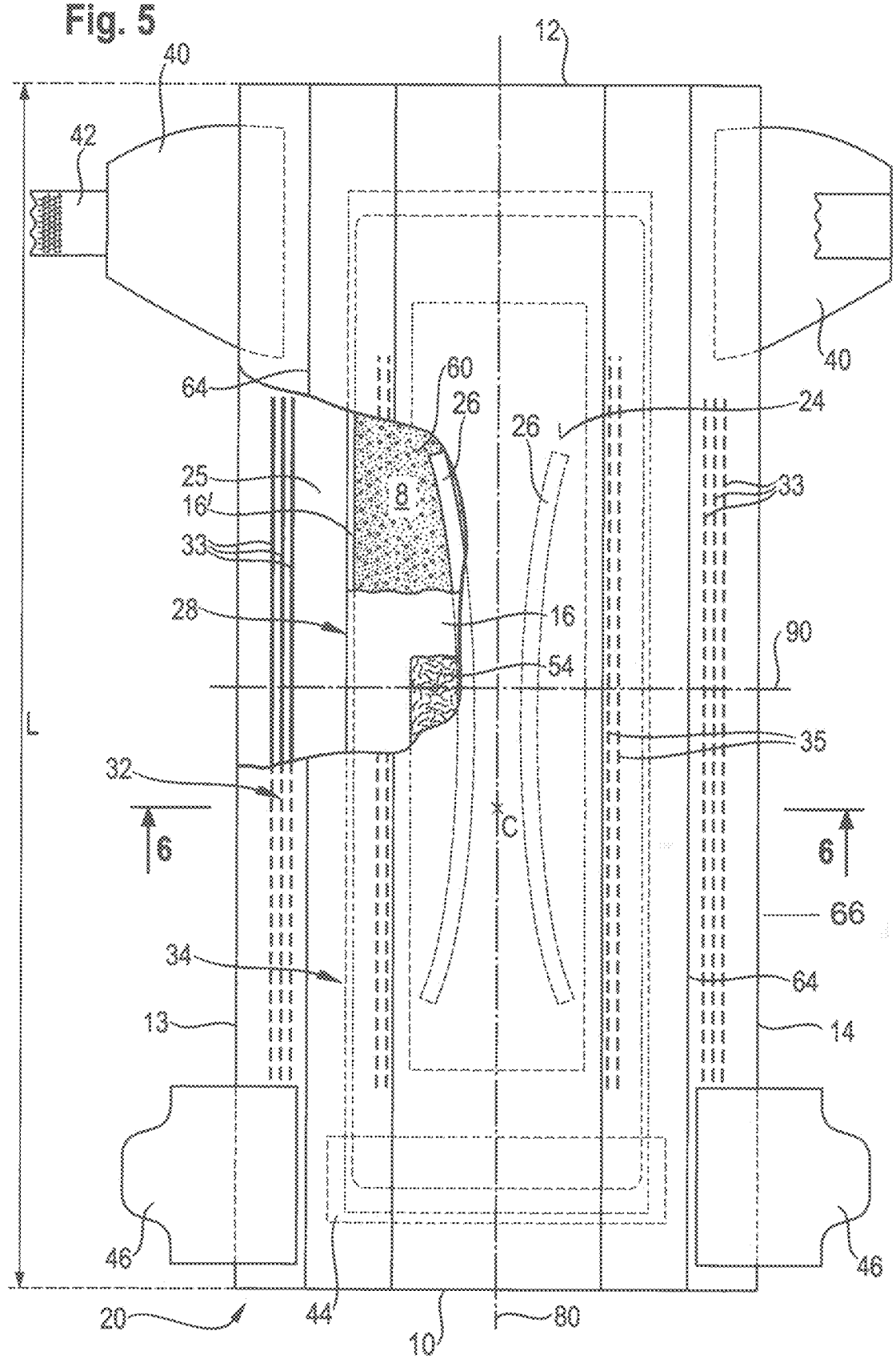
FIG. 5 is a top view of an exemplary absorbent article in the form a diaper with an absorbent core of the invention.
Figure 6:
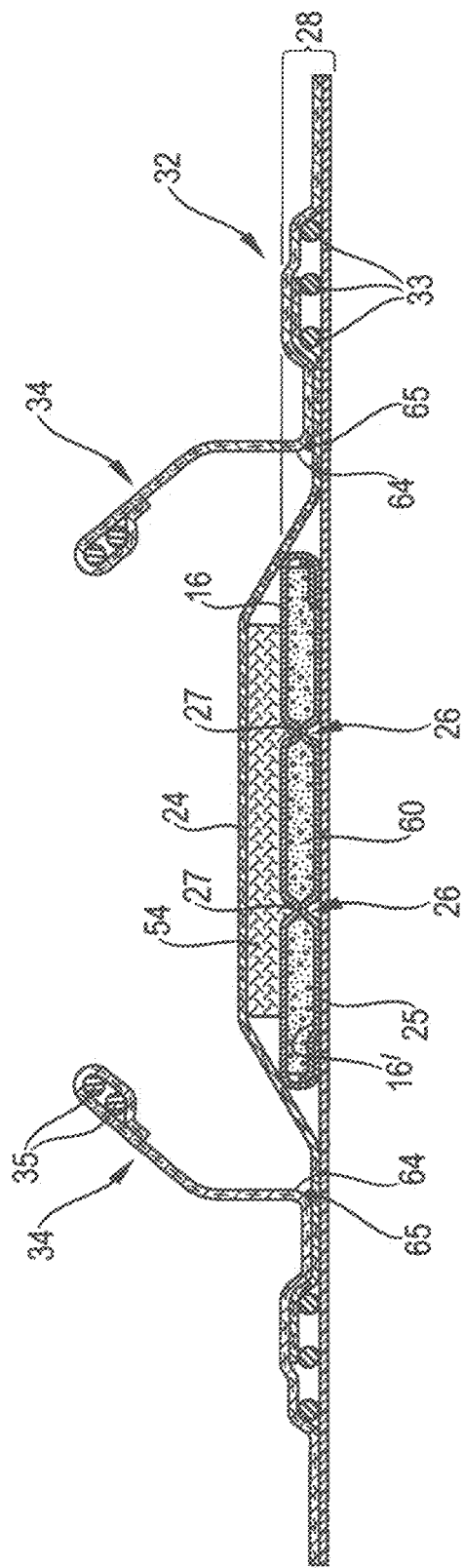
FIG. 6 is a transversal cross-section of the article of FIG. 5.

Having now discussed in quite details certain embodiments of the absorbent cores of the invention, the absorbent articles in which these cores may be used will now be generally discussed and further illustrated in the form of a baby diaper 20 in FIGS. 5-7. FIG. 5 is a plan view of the exemplary diaper 20, in a flattened state, with portions of the structure being cut-away to more clearly show the construction of the diaper 20. This diaper 20 is shown for illustration purpose only as the invention may be used for making a wide variety of diapers or other absorbent articles.

The absorbent article comprises a liquid permeable topsheet 24, a liquid impermeable backsheet 25, and an absorbent core 28 between the topsheet 24 and the backsheet 25. An optional acquisition/distribution layer 54 is represented on FIG. 5, which also shows other typical taped diaper components such as a fastening system comprising adhesive tabs 42 attached towards the back edge of the article and cooperating with a landing zone 44 on the front of the article, barrier leg cuffs 34 and elasticized gasketing cuffs 32 joined to the chassis of the absorbent article, typically via the topsheet and/or backsheet, and substantially planar with the chassis of the diaper. The absorbent article may also comprise other typical elements, which are not represented, such as a back elastic waist feature, a front elastic waist feature, transverse barrier cuff(s), a lotion application, etc. . . . .

The absorbent article 20 comprises a front edge 10, a back edge 12, and two side (longitudinal edges) 13, 14. The front edge 10 of the article is the edge which is intended to be placed towards the front of the user when worn, and the back edge 12 is the opposite edge of the article. The absorbent article may be notionally divided by a longitudinal axis 80 extending from the front edge to the back edge of the article and dividing the article in two substantially symmetrical halves relative to this axis, with article placed flat and viewed from above as in FIG. 5. The length L of the article can be measured along the longitudinal axis 80 from front edge 10 to back edge 12. The article comprises a crotch point C defined herein as the point placed on the longitudinal axis at a distance of two fifth (2/5) of L starting from the front edge 10 of the article 20. The width of the article for a diaper application at the crotch point may in particular be of from 50 mm to 300 mm, or from 80 mm to 250 mm. For adult incontinence products the width may go up to 450 mm.

The crotch region can be defined as the region of the diaper longitudinally centered at the crotch point C and extending towards the front and towards the back of the absorbent article by a distance of one fifth of L (L/5) in each direction. A front region and a back region can be defined as the remaining portions of the diapers placed respectively towards the front and the back edges of the article.

The topsheet 24, the backsheet 25, the absorbent core 28 and the other article components may be assembled in a variety of well known configurations, in particular by gluing or heat embossing. Exemplary diaper configurations are described generally in U.S. Pat. Nos. 3,860,003, 5,221,274, U.S. Pat. Nos. 5,554,145, 5,569,234, 5,580,411, and 6,004, 306. The absorbent article is preferably thin. The caliper at the crotch point C of the article may be for example from 3.0 mm to 12.0 mm, in particular from 4.0 mm to 10.0 mm, as measured with the Absorbent Article Caliper Test described herein.

For most absorbent articles, the liquid discharge occurs predominately in the front half of the article, in particular for diaper. The front half of the article (as defined by the region between the front edge and a transversal line 90 placed at a distance of half L from the front or back edge may therefore comprise most of the absorbent capacity of the core. Thus, at least 60% of the SAP, or at least 65%, 70%, 75% or 80% of the SAP may be present in the front half of the absorbent article, the remaining SAP being disposed in the back half of the absorbent article.

The absorbent article may have an acquisition time for the first gush of less than 30 s, preferably less than 27 s, as measured according to the Flat Acquisition test method set out in WO2012/174026A1. This acquisition time may be in measured in particular on a baby diaper which is designated for wearers having a weight in the range of 8 to 13 kg±20% (such as Pampers Active Fit size 4 or other Pampers baby diapers size 4, Huggies baby diapers size 4 or baby diapers size 4 of most other tradenames).

Topsheet 24

The topsheet 24 is the layer of the absorbent article that is destined to be in contact with the wearer's skin. The topsheet 24 can be joined to the backsheet 25, the core 28 and/or any other layers as is known in the art. Usually, the topsheet 24 and the backsheet 25 may be joined directly to each other on or close to the periphery of the article and are indirectly joined together in other locations by directly joining them to one or more other elements of the article 20. The topsheet may be attached to an underlying layer 54, which may be an acquisition and/or distribution layer, by any conventional means, in particular gluing, mechanical or heat bonding and combinations thereof. The topsheet may in particular be attached directly or indirectly to the fibrous layer 54 in the area where the ditches of the fibrous layer are formed, as exemplarily shown in FIG. 7. This may provide or help the formation of secondary ditches 29 at the surface of the article.

The topsheet 24 is preferably compliant, soft-feeling, and non-irritating to the wearer's skin. Further, at least a portion of the topsheet 24 is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. If the topsheet includes fibers, the fibers may be spunbond, carded, wet-laid, meltblown, hydroentangled, or otherwise processed as is known in the art, in particular spunbond PP nonwoven. A suitable topsheet comprising a web of staple-length polypropylene fibers is manufactured by Veratec, Inc., a Division of International Paper Company, of Walpole, MA under the designation P-8.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643 issued to Curro et al. Such formed films are available from The Procter & Gamble Company of Cincinnati, Ohio as "DRI-WEAVE" and from Tredegar Corporation, based in Richmond, VA, as "CLIFF-T".

Any portion of the topsheet 24 may be coated with a lotion as is known in the art. Examples of suitable lotions include those described in U.S. Pat. Nos. 5,607,760, 5,609,587, 5,635,191, 5,643,588, 5,968,025 and 6,716,441. The topsheet 24 may also include or be treated with antibacterial agents, some examples of which are disclosed in PCT Publication WO95/24173. Further, the topsheet 24, the backsheet 25 or any portion of the topsheet or backsheet may be embossed and/or matte finished to provide a more cloth like appearance.

The topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the total area of the apertures at the surface of a diaper may have an area of between about 10 $cm^2$ and about 50 $cm^2$, in particular between about 15 $cm^2$ and 35 $cm^2$. Examples of apertured topsheet are disclosed in U.S. Pat. No. 6,632,504, assigned to BBA NONWOVENS SIMPSONVILLE. WO2011/163582 also discloses suitable colored topsheet having a basis weight of from 12 to 18 gsm and comprising a plurality of bonded points. Each of the bonded points has a surface area of from 2 $mm^2$ to 5 $mm^2$ and the cumulated surface area of the plurality of bonded points is from 10 to 25% of the total surface area of the topsheet.

Typical diaper topsheets have a basis weight of from about 10 to about 28 gsm, in particular between from about 12 to about 18 gsm but other basis weights are possible.

Backsheet 25

The backsheet 25 is generally that portion of the absorbent article 20 which forms the majority of the external surface of the article when worn by the user. The backsheet is positioned towards the bottom side of the absorbent core and prevents the exudates absorbed and contained therein from soiling articles such as bedsheets and undergarments. The backsheet 25 is typically impermeable to liquids (e.g. urine). The backsheet may for example be or comprise a thin plastic film such as a thermoplastic film having a thickness of about 0.012 mm to about 0.051 mm. Exemplary backsheet films include those manufactured by Tredegar Corporation, based in Richmond, VA, and sold under the trade name CPC2 film. Other suitable backsheet materials may include breathable materials which permit vapors to escape from the diaper 20 while still preventing exudates from passing through the backsheet 25. Exemplary breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, VA, and sold under the designation EXAIRE, and monolithic films such as manufactured by Clopay Corporation, Cincinnati, OH under the name HYTREL blend P18-3097. Some breathable composite materials are described in greater detail in PCT Application No. WO 95/16746 published on Jun. 22, 1995 in the name of E. I. DuPont; U.S. Pat. No. 5,938,648 to LaVon et al., U.S. Pat. No. 4,681,793 to Linman et al., U.S. Pat. No. 5,865,823 to Curro; and U.S. Pat. No. 5,571,096 to Dobrin et al, U.S. Pat. No. 6,946,585B2 to London Brown.

The backsheet 25 may be joined to the topsheet 24, the absorbent core 28 or any other element of the diaper 20 by any attachment means known in the art. Suitable attachment means are described above with respect to means for joining the topsheet 24 to other elements of the article 20. For example, the attachment means may include a uniform continuous layer of adhesive, a patterned layer of adhesive, or an array of separate lines, spirals, or spots of adhesive. Suitable attachment means comprises an open pattern network of filaments of adhesive as disclosed in U.S. Pat. No. 4,573,986. Other suitable attachment means include several lines of adhesive filaments which are swirled into a spiral pattern, as is illustrated by the apparatus and methods shown in U.S. Pat. Nos. 3,911,173, 4,785,996; and 4,842,666. Adhesives which have been found to be satisfactory are manufactured by H. B. Fuller Company of St. Paul, Minnesota and marketed as HL-1620 and HL 1358-XZP. Alternatively, the attachment means may comprise heat bonds, pressure bonds, ultrasonic bonds, dynamic mechanical bonds, or any other suitable attachment means or combinations of these attachment means as are known in the art.

Additional Layer 54

The absorbent article may further comprise one or more additional layer 54 that can serve to acquire and distribute the fluid, as illustrate by layer 54 in the Figures. The additional layer(s) may be present between the topsheet 24 and the absorbent core 28, as represented in the Figures, but it may be also between the backsheet 25 and the absorbent core 28, or both. The additional layer 54 may be at least partially bonded to the top side or the bottom side of the core wrap in the area(s) substantially free of absorbent material. The formation of the channel 26' in the absorbent core as the absorbent material swells may thus provides of one or more corresponding ditches 27 in the additional layer 54.

The additional layer(s) may be of any kind such as nonwoven, a woven material or even loose fibers. The additional layers may in particular be of the type known in the art for acquisition layers and/or distribution layers. Typical acquisition and/or distribution layers do not comprise SAP as this may slow the acquisition and distribution of the fluid, but an additional layer may also comprise SAP if some fluid retention properties are wished. The prior art discloses many type of acquisition and/or distribution layers that may be used, see for example WO2000/59430 (Daley), WO95/10996 (Richards), U.S. Pat. No. 5,700,254 (McDowall), WO02/067809 (Graef).

A distribution layer can spread an insulting fluid liquid over a larger surface within the article so that the absorbent capacity of the core can be more efficiently used. Typically distribution layers are made of a nonwoven material based on synthetic or cellulosic fibers and having a relatively low density. The density of the distribution layer may vary depending on the compression of the article, but may typically range from 0.03 to 0.25 $g/cm^3$, in particular from 0.05 to 0.15 $g/cm^3$ measured at 0.30 psi (2.07 kPa). The distribution layer may also be a material having a water retention value of from 25 to 60, preferably from 30 to 45, measured as indicated in the procedure disclosed in U.S. Pat.

No. 5,137,537. The distribution layer may typically have an average basis weight of from 30 to 400 g/m², in particular from 100 to 300 g/m².

The distribution layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The cross-linked cellulosic fibers provide higher resilience and therefore higher resistance to the first absorbent layer against the compression in the product packaging or in use conditions, e.g. under a baby's weight. This provides the core with a higher void volume, permeability and liquid absorption, and hence reduced leakage and improved dryness.

Exemplary chemically cross-linked cellulosic fibers suitable for a distribution layer are disclosed in U.S. Pat. Nos. 5,549,791, 5,137,537, WO9534329 or US2007/118087. Exemplary cross-linking agents include polycarboxylic acids such as citric acid and/or polyacrylic acids such as acrylic acid and maleic acid copolymers.

The absorbent article may also comprise an acquisition layer as additional layer, whose function can be to quickly acquire the fluid away from the topsheet so as to provide a good dryness for the wearer. Such an acquisition layer is typically placed directly under the topsheet. The absorbent article may also then comprise a distribution layer typically placed between the acquisition layer and the absorbent core.

The acquisition layer may typically be or comprise a non-woven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Non-wovens have the advantage that they can be manufactured outside the converting line and stored and used as a roll of material. Further useful non-wovens are described in U.S. Pat. Nos. 6,645,569, 6,863,933 (both to Cramer), U.S. Pat. No. 7,112,621 (Rohrbaugh), and co patent applications US2003/148684 to Cramer et al. and US2005/008839 (both to Cramer).

Such an acquisition layer may be stabilized by a latex binder, for example a styrene-butadiene latex binder (SB latex). Processes for obtaining such lattices are known, for example, from EP 149 880 (Kwok) and US 2003/0105190 (Diehl et al.). In certain embodiments, the binder may be present in the acquisition layer in excess of about 12%, about 14% or about 16% by weight. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13-22.5 gsm high wet strength made of cellulose fibers from supplier Havix.

If an acquisition layer is present, it may be advantageous that this acquisition layer is larger than or least as large as an underlying distribution layer in the longitudinal and/or transversal dimension. In this way the distribution layer can be deposited on the acquisition layer. This simplifies handling, in particular if the acquisition layer is a nonwoven which can be unrolled from a roll of stock material. The distribution layer may also be deposited directly on the absorbent core's upper side of the core wrap or another layer of the article. Also, an acquisition layer larger than the distribution layer allows to directly glue the acquisition layer to the storage core (at the larger areas). This can give increased patch integrity and better liquid communication.

Fastening System 42, 44

The absorbent article may include a fastening system, for example as is known in taped diapers. The fastening system can be used to provide lateral tensions about the circumference of the absorbent article to hold the absorbent article on the wearer as is typical for taped diapers. This fastening system is not necessary for training pant article since the waist region of these articles is already bonded. The fastening system usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone is normally provided on the front waist region for the fastener to be releasably attached. Some exemplary surface fastening systems are disclosed in U.S. Pat. Nos. 3,848,594, 4,662,875, 4,846,815, 4,894,060, 4,946,527, 5,151,092 and 5,221,274 issued to Buell. An exemplary interlocking fastening system is disclosed in U.S. Pat. No. 6,432,098. The fastening system may also provide a means for holding the article in a disposal configuration as disclosed in U.S. Pat. No. 4,963,140 issued to Robertson et al.

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, 5,507,736, and 5,591,152.

Barrier Leg Cuffs 34

The absorbent article may comprise a pair of barrier leg cuffs 34 and/or gasketing cuffs 32. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. describe disposable diapers having "stand-up" elasticized flaps (barrier leg cuffs) which improve the containment of the leg regions. U.S. Pat. Nos. 4,695,278 and 4,795,454 issued to Lawson and to Dragoo respectively, describe disposable diapers having dual cuffs, including gasketing cuffs and barrier leg cuffs. All or a portion of the barrier leg and/or gasketing cuffs may be treated with a lotion.

The barrier leg cuffs 34 can be formed from a piece of material, typically a nonwoven, which is partially bonded to the rest of the article so that a portion of the material, the barrier leg cuffs, can be partially raised away and stand up from the plane defined by the topsheet when the article is pulled flat as shown e.g. in FIG. 5. The barrier leg cuffs can provide improved containment of liquids and other body exudates approximately at the junction of the torso and legs of the wearer. The barrier leg cuffs extend at least partially between the front edge and the back edge of the diaper on opposite sides of the longitudinal axis and are at least present at the longitudinal position of the crotch point (C). The barrier leg cuffs are delimited by a proximal edge 64 joined to the rest of the article, typically the topsheet and/or the backsheet, and a free terminal edge 66, which is intended to contact and form a seal with the wearer's skin. The barrier leg cuffs are joined at the proximal edge 64 with the chassis of the article by a bond 65 which may be made for example by gluing, fusion bonding or combination of known bonding means. The bond 65 at the proximal edge 64 may be continuous or intermittent. The side of the bond 65 closest to the raised section of the barrier leg cuffs 34 delimits the proximal edge 64 of the standing up section of the leg cuffs.

The barrier leg cuffs 34 can be integral with the topsheet or the backsheet, or more typically be formed from a separate material joined to the rest of the article. Typically the material of the barrier leg cuffs may extend through the whole length of the diapers but is "tack bonded" to the topsheet towards the front edge and back edge of the article so that in these sections the barrier leg cuff material remains flush with the topsheet. Each barrier leg cuff 34 may comprise one, two or more elastic strings 35 close to this free terminal edge 66 to provide a better seal.

In addition to the barrier leg cuffs 34, the article may comprise gasketing cuffs 32 joined to the chassis of absorbent article, in particular the topsheet and/or the backsheet and may be placed externally relative to the barrier leg cuffs. The gasketing cuffs can provide a better seal around the thighs of the wearer. Usually each gasketing leg cuff will comprise one or more elastic string or elastic element 33 comprised in the chassis of the diaper for example between the topsheet and backsheet in the area of the leg openings.

Front and Back Ears 46, 40

The absorbent article may comprise front ears 46 and back ears 40 as is known in the art. The ears can be integral part of the chassis, for example formed from the topsheet and/or backsheet as side panel. Alternatively, as represented on FIG. 5, they may be separate elements attached by gluing and/or heat embossing or pressure bonding. The back ears 40 are advantageously stretchable to facilitate the attachment of the tabs 42 on the landing zone 44 and maintain the taped diapers in place around the wearer's waist. The back ears 40 may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Elastic Waist Feature

The absorbent article may also comprise at least one elastic waist feature (not represented) that helps to provide improved fit and containment. The elastic waist feature is generally intended to elastically expand and contract to dynamically fit the wearer's waist. The elastic waist feature preferably extends at least longitudinally outwardly from at least one waist edge of the absorbent core 28 and generally forms at least a portion of the end edge of the absorbent article. Disposable diapers can be constructed so as to have two elastic waist features, one positioned in the front waist region and one positioned in the back waist region. The elastic waist feature may be constructed in a number of different configurations including those described in U.S. Pat. Nos. 4,515,595, 4,710,189, 5,151,092 and 5,221,274.

Method of Making the Article—Relations Between the Layers

The absorbent articles of the invention may be made by any conventional methods known in the art. In particular the articles may be hand-made or industrially produced at high speed. Typically, adjacent layers and components will be joined together using conventional bonding method such as adhesive coating via slot coating or spraying on the whole or part of the surface of the layer, or thermo-bonding, or pressure bonding or combinations thereof. This bonding is exemplarily represented for the bond between the leg cuffs 65 and the topsheet 24 on FIG. 6, and the auxiliary glues 71, 72 and microfibrous glue 51 on the detail view of the absorbent core on FIG. 4. Other glues or attachments are not represented for clarity and readability but typical bonding between the layers of the article should be considered to be present unless specifically excluded. Adhesives may be typically used to improve the adhesion of the different layers, for example between the backsheet and the core wrap. The glue may be any standard hotmelt glue as known in the art.

The absorbent core and in particular its absorbent material deposition area 8 may advantageously be at least as large and long and advantageously at least partially larger and/or longer than the fibrous layer. This is because the absorbent material in the core can usually more effectively retain fluid and provide dryness benefits across a larger area than the fibrous layer. The absorbent article may have a rectangular SAP layer and a non-rectangular (shaped) fibrous layer. The absorbent article may also have a rectangular (non-shaped) fibrous layer and a rectangular layer of SAP.

Experimental Settings

K(t) Method (Dynamic Effective Permeability and Uptake Kinetics Measurement Test Method)

This method determines the time dependent effective permeability (K(t)) and the uptake kinetics of a gel layer formed from hydrogel-forming superabsorbent polymer particles or of an absorbent structure containing such particles under a confining pressure. The objective of this method is to assess the ability of the gel layer formed from hydrogel-forming superabsorbent polymer particles or the absorbent structure containing them to acquire and distribute body fluids when the polymer is present at high concentrations in an absorbent article and exposed to mechanical pressures as they typically occur during use of the absorbent article. Darcy's law and steady-state flow methods are used to calculate effective permeability (see below). See also for example, "Absorbency," ed. by P. K. Chatterjee, Elsevier, 1982, Pages 42-43 and "Chemical Engineering Vol. II, Third Edition, J. M. Coulson and J. F. Richardson, Pergamon Press, 1978, Pages 122-127.

In contrast to previously published methods, the sample is not preswollen therefore the hydrogel is not formed by preswelling hydrogel-forming superabsorbent polymer particles in synthetic urine, but the measurement is started with a dry structure. This method was also fully disclosed in WO2012/174026A1.

The equipment used for this method is called 'Zeitabhängiger Durchlässigkeitsprüfstand' or 'Time Dependent Permeability Tester', Equipment No. 03-080578 and is commercially available at BRAUN GmbH, Frankfurter Str. 145, 61476 Kronberg, Germany and is described below. Upon request, operating instructions, wiring diagrams and detailed technical drawings are also available.

Dynamic Effective Permeability and Uptake Kinetic Measurement System

Figure 9:
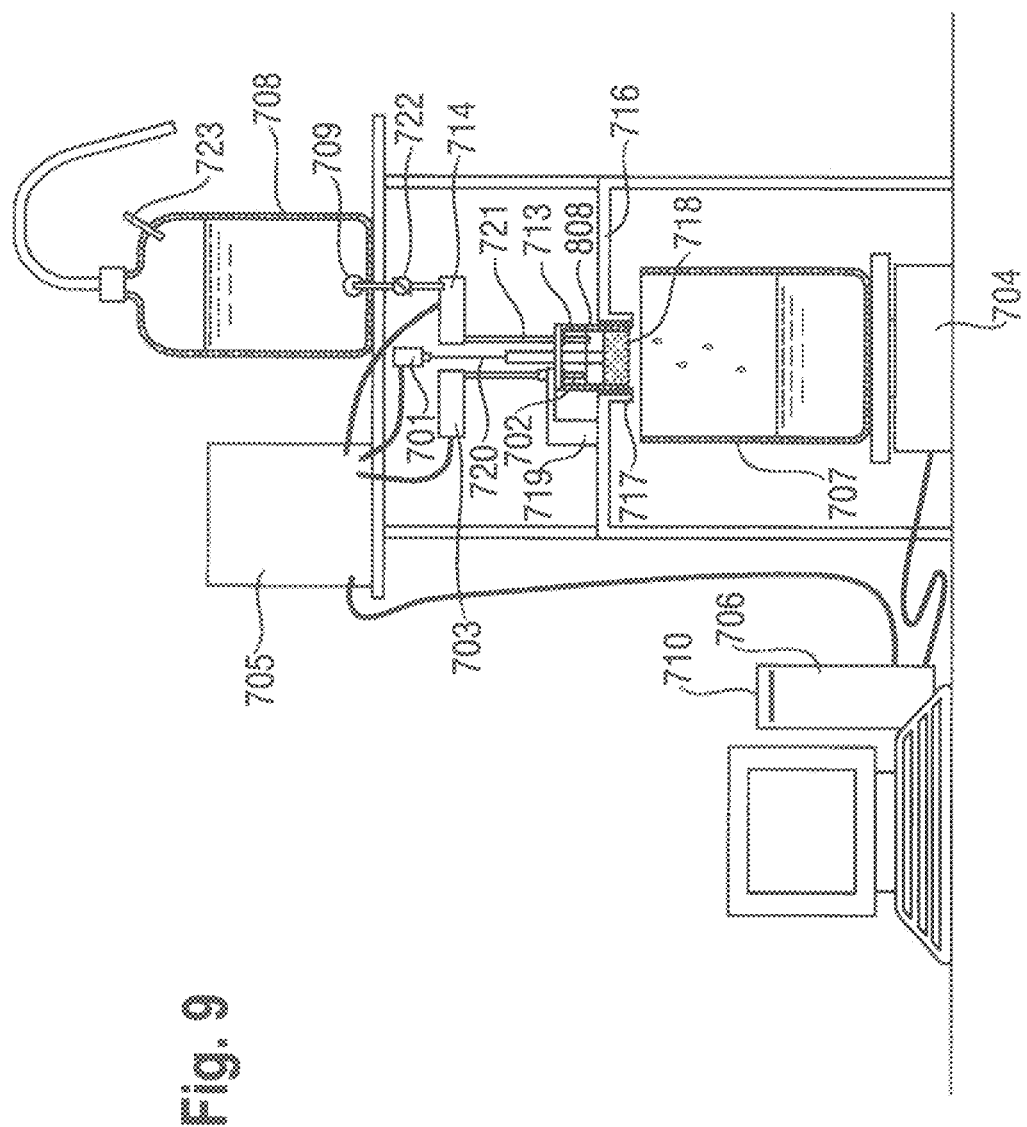
FIG. 9 is a partial cross-sectional side view of a suitable permeability measurement system for conducting the Dynamic Effective Permeability and Uptake Kinetics Measurement Test.

FIG. 9 shows the dynamic effective permeability and uptake kinetic measurement system, called 'Time Dependent Permeability Tester' herein. The equipment consists of the following main parts:

M11 Digital Laser Sensor for caliper measurement 701 (MEL Mikroelektronik GmbH, 85386 Eching, Germany Fiber for Liquid Level Detection 702 (FU95, Keyence Corp., Japan)

Digital Fiber Sensor 703 (FS-N10, Keyence Corp., Japan)

Precision Balance 704 (XP6002MDR, Mettler Toledo AG, 8606 Greifensee, Switzerland)

Power Unit Logo!Power (C98130-A7560-A1-5-7519, Siemens AG)

Labview Software License 706 (National Instruments, Austin, Tx, USA)

Receiving Vessel 707 (5 L Glass Beaker, Roth)

Reservoir 708 (5 L Glass bottle, VWR) with joint 709 and open-end tube for air admittance 723

Operating unit and console 705 (Conrad Electronics)

Computerized data acquisition system 710

A piston/cylinder assembly 713 as described herein

A controlled valve 714 (Bürkert)

Figure 11:
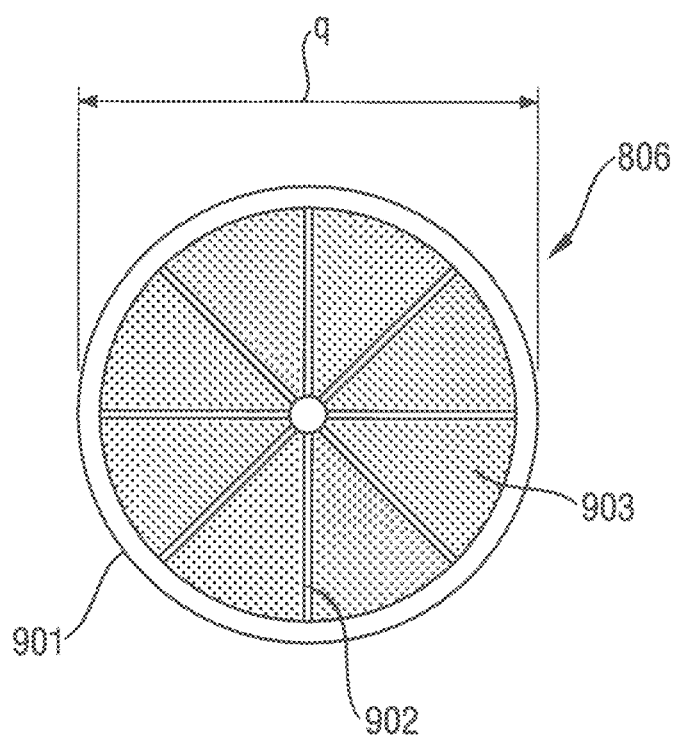
FIG. 11 is a top view of a piston head suitable for use in the piston/cylinder assembly shown in FIG. 10.

FIG. 10 shows the piston/cylinder assembly 713 comprising piston guiding lid 801, piston 802 and cylinder 803. The cylinder 803 is made of transparent polycarbonate (e.g., Lexan®) and has an inner diameter p of 6.00 cm (area=28.27 cm$^2$). The inner cylinder walls 850 are smooth; the height of the cylinder r is about 7.50 cm. The bottom 804 of the cylinder 803 is faced with a US. Standard 400 mesh stainless-steel screen cloth (not shown) (e.g. from Weisse and Eschrich) that is bi-axially stretched to tautness prior to attachment to the bottom 804 of the cylinder 803. The piston 802 is composed of a stainless steel piston body 805 and a stainless steel head 806. The piston head 806 diameter q is slightly less than 6 cm so as to slide freely into the cylinder 803 without leaving any gap for the hydrogel-forming particle to pass trough. The piston body 805 is firmly attached perpendicularly at the center of the piston head 806. The piston body diameter t is about 2.2 cm. The piston body 805 is then inserted into a piston guiding lid 801. The guiding lid 801 has a POM (Polyoxymethylene) ring 809 with a diameter allowing a free sliding of the piston 802 yet keeping the piston body 805 perfectly vertical and parallel to the cylinder walls 850 once the piston 802 with the guiding lid 801 are positioned on top of the cylinder 803. The top view of the piston head 806 is shown in FIG. 11. The piston head 806 is meant to apply the pressure homogeneously to the sample 718. It is also highly permeable to the hydrophilic liquid so as to not limit the liquid flow during measurement. The piston head 806 is composed of a US. standard 400 mesh stainless steel screen cloth 903 (e.g. from Weisse and Eschrich) that is bi-axially stretched to tautness and secured at the piston head stainless steel outer ring 901. The entire bottom surface of the piston is flat. Structural integrity and resistance to bending of the mesh screen is then ensured by the stainless steel radial spokes 902. The height of the piston body 805 is selected such that the weight of the piston 802 composed of the piston body 805 and the piston head 806 is 596 g (±6 g), this corresponds to 0.30 psi over the area of the cylinder 803.

The piston guiding lid 801 is a flat circle of stainless steel with a diameter s of about 7.5 cm held perpendicular to the piston body 805 by the POM ring 809 in its center. There are two inlets in the guiding lid (810 and 812).

The first inlet 812, allows the Fiber for Liquid Level Detection 702 to be positioned exactly 5 cm above the top surface of the screen (not shown) attached to the bottom (804) of the cylinder 803 once the piston 802 is assembled with the cylinder 803 for the measurement.

The second inlet 810 allows connecting a liquid tube 721 providing the liquid to the experiment. To make sure that the assembly of the piston 802 with the cylinder 803 is done consistently a slit 814 is made on the cylinder 803 matching a position marker 813 in the guiding lid 801. In this way the rotation angle of the cylinder and the guiding lid is always the same.

Prior to every use, the stainless steel screen cloth 903 of the piston head 806 and cylinder 803 should be inspected for clogging, holes or over-stretching and replaced when necessary. A K(t) apparatus with damaged screen can deliver erroneous K(t) and uptake kinetic results, and must not be used until the screen has been replaced.

A 5 cm mark 808 is scribed on the cylinder at a height k of 5.00 cm (±0.02 cm) above the top surface of the screen attached to the bottom 804 of the cylinder 803. This marks the fluid level to be maintained during the analysis. The Fiber for Liquid Level Detection 702 is positioned exactly at the 5 cm mark 808. Maintenance of correct and constant fluid level (hydrostatic pressure) is critical for measurement accuracy A reservoir 708 connected via tubing to the piston/cylinder assembly 713 holding the sample and a controller valve 714 are used to deliver salt solution to the cylinder 803 and to maintain the level of salt solution at a height k of 5.00 cm above the top surface of screen attached to the bottom of the cylinder 804. The valve 714, the Fiber for Liquid Level Detection 702 and the Digital Fiber Sensor 703 are connected to the computerized acquisition system 710 trough the operating unit 705. This allows the Dynamic Effective Permeability and Uptake Kinetic Measurement System to use the information from the Fiber for Liquid Level Detection 702 and the Digital Fiber Sensor 703 to control the valve 714 and ultimately maintain the level of the liquid at the 5 cm mark 808.

The reservoir 708 is placed above the piston/cylinder assembly 713 in such a manner as to allow a 5 cm hydrohead to be formed within 15 seconds of initiating the test, and to be maintained in the cylinder throughout the test procedure. The piston/cylinder assembly 713 is positioned on the support ring 717 of the cover plate 716 and the first inlet 812 is held in place with the docking support 719. This allows only one position of the guiding lid 801. Furthermore, due to the position marker 813, there is also only one position for the cylinder 803. The screen attached to the bottom of the cylinder 804 must be perfectly level and horizontal. The supporting ring 717 needs to have an internal diameter small enough, so to firmly support cylinder 803 but larger than 6.0 cm so to lay outside of the internal diameter of the cylinder once the cylinder is positioned on the supporting ring 717. This is important so to avoid any interference of the supporting ring 717 with the liquid flow.

The salt solution, applied to the sample 718 with a constant hydrohead of 5 cm can now freely flow from the piston/cylinder assembly 713 into a receiving vessel 707 positioned on the balance 704 which is accurate within ±0.01 g. The digital output of the balance is connected to a computerized data acquisition system.

The caliper (thickness) of the sample is constantly measured with a Digital Laser Sensor for caliper measurement 701. The laser beam 720 of the digital laser sensor 701 is directed at the center of the POM cover plate 811 of the piston body. The accurate positioning of all the parts of the piston/cylinder assembly 713 allows the piston body 805 to be perfectly parallel to the laser beam 720 and as a result an accurate measure of the thickness is obtained.

Test Preparation

The reservoir 708 is filled with test solution. The test solution is an aqueous solution containing 9.00 grams of sodium chloride and 1.00 grams of surfactant per liter of solution. The preparation of the test solution is described below. The receiving vessel 707 is placed on the balance 704 which is connected to a computerized data acquisition system 710. Before the start of the measurement the balance is reset to zero.

Preparation of Test Liquid:

Chemicals needed:

Sodium Chloride (CAS #7647-14-5, eg: Merck, cat #1.06404.1000)

Linear $C_{12}$-$C_{14}$ alcohol ethoxylate (CAS #68439-50-9, eg. Lorodac®, Sasol, Italy)

Deionized $H_2O$

Ten liters of a solution containing 9.00 grams per litre of NaCl and 1.00 grams per liter linear C12-C14 alcohol ethoxalate in distilled water is prepared and equilibrated at 23° C.±1° C. for 1 hour. The surface tension is measured on 3 individual aliquots and should be 28±0.5 mN/m. If the surface tension of the solution is different from 28±0.5 mN/m, the solution is discarded and a new test solution is prepared. The test solution has to be used within 36 hours from its preparation and is considered expired afterwards.

K(t) Sample Preparation

A 10 grams representative sample of the superabsorbent polymer particles is obtained. This is then dried in an uncovered 10 cm diameter Petri dish in a vacuum chamber at 23±2° C. and 0.01 Torr or lower for 48 hours prior to use. The sample is removed from the vacuum chamber and immediately stored in a tightly sealed 20 mL glass airtight container at 23±2° C. until further use.

2.0 g (±0.02 g) of superabsorbent polymer particles are weighed onto a suitable weighing paper using an analytical balance and transferred to the cylinder 803 with the particles distributed evenly on the screen (not shown) attached to the bottom 804 of the cylinder 803. This is done via sprinkling the superabsorbent polymer, while at the same time turning the cylinder clockwise (e.g. on a circular turning table schuett petriturn-M available at Schuett-biotec GmbH, Rudolf-Wissell-Str. 13 D-37079 Göttingen Germany). An even distribution of the superabsorbent polymer particles is critical for the measurements accuracy.

K(t) Procedure

The measurement is carried out at Tappi lab conditions: 23° C.±1° C./50% RH±2%. The empty piston/cylinder assembly 713 is mounted in the circular opening in the cover plate 716 and is supported around its lower perimeter by the supporting ring 717. The piston/cylinder assembly 713 is held in place with the docking support 719 with the cylinder 803 and piston 802 aligned at the proper angle. The reference caliper reading ($r_r$) is measured by Digital Laser sensor. After this, the empty piston/cylinder assembly 713 is removed from the cover plate 716 and supporting ring 717 and the piston 802 is removed from the cylinder 803.

The sample 718 is positioned (absorbent structure) or sprinkled (superabsorbent polymer particles) on the cylinder screen as explained above. After this, the piston 802 assembled with the guiding lid 801 is carefully set into the cylinder 803 by matching the position marker 813 of the guiding lid 801 with the slit 814 made in the cylinder 803

The piston/cylinder assembly is held in place with the docking support 719 with the cylinder and piston aligned at the proper angle This can be only done in one way. The liquid tube 721 connected to the reservoir 708 and the Digital Fiber Sensor 703 are inserted into the piston/cylinder assembly 713 via the two inlets 810 and 812 in the guiding lid 801.

The computerized data acquisition system 710 is connected to the balance 704 and to the digital laser sensor for caliper measurement 701. Fluid flow from the reservoir 708 to the cylinder 803 is initiated by the computer program by opening valve 714. The cylinder is filled until the 5 cm mark 808 is reached in 5 to 15 seconds, after which the computer program regulates the flow rate to maintain a constant 5 cm hydrohead. The quantity of solution passing through the sample 718 is measured by the balance 704 and the caliper increase is measured by the laser caliper gauge. Data acquisition is started when the fluid flow is initiated specifically when the valve 714 is opened for the first time, and continues for 21 minutes or until the reservoir runs dry so that the 5 cm hyrdrohead is no longer maintained. The duration of one measurement is 21 min, laser caliper and balance readings are recorded regularly with an interval that may vary according to the measurement scope from 2 to 10 sec, and 3 replicates are measured.

After 21 min, the measurement of the $1^{st}$ replicate is successfully completed and the controlled valve 714 closes automatically. The piston/cylinder assembly 713 is removed and the measurements of the $2^{nd}$ and $3^{rd}$ replicates are done accordingly, always following the same procedure. At the end of the measurement of the $3^{rd}$ replicate, the controlled valve 714 stops the flow of liquid and stopcock 722 of the reservoir 708 is closed. The collected raw data is stored in the form of a simple data table, which then can be imported easily to a program for further analysis e.g. Excel 2003, SP3.

In the data table the following relevant information is reported for each reading:

Time from the beginning of the experiment

Weight of the liquid collected by the receiving vessel 707 on the balance 704

Caliper of the sample 718

The data from 30 seconds to the end of the experiment are used in the K(t) and uptake kinetics calculation. The data collected in the first 30 seconds are not included in the calculation. The effective permeability K(t) and the uptake kinetics of the absorbent structure are then determined using the equation sets below.

Used Equations:

The table below describes the notation used in the equations.

| | |
|---|---|
| A | x-section of the absorbent structure sample which corresponds to the cylinder inner radius: 28.27 $cm^2$ |
| h | height of water column, 5.0 cm |
| Δp | driving pressure applied by the 5.00 cm hydrohead (h) : 4929.31 g/(cm $s^2$) |
| G | gravity constant: 981 cm/$s^2$ |
| η | Temperature dependent effective viscosity of the liquid in g/(cm s) |
| T | Temperature in ° C. |
| ρ | density of the liquid: 1.0053 g/$cm^3$ |
| $ρ_s^A$ | Apparent sample density of the porous medium or powder in g/$cm^3$ |
| $ρ_s$ | Average density of the solid part of the dry sample in g/$cm^3$ |
| $ρ_{s,k}$ | Density of the component k of the dry sample in g/$cm^3$ |
| M | dry mass of the sample in g: 2.00 g if measuring superabsorbent particles |
| $m_k$ | Mass of the component k of the dry sample in g |
| $V_s$ | Dry sample volume in $cm^3$ |
| $t_i$ | time at step i of N discrete points in s |

| | |
|---|---|
| $d_i$ | caliper of the absorbent structure sample at time $t_i$ in cm |
| $r_i$ | reading of caliper instrument at time $t_i$ in cm |
| $r_r$ | reference reading of caliper instrument (reading of the piston/cylinder assembly without sample) in cm |
| $m_{out\,i}$ | balance reading at time $t_i$; mass of the liquid that left the sample at time $t_i$ in g |
| $U(t_i)$ | Sample uptake at time $t_i$ in g |
| T20 | time required to reach an uptake of 20 g/g, starting at 0 s ($t_0$) in s |
| U20 | Sample uptake after 20 minutes in g/g |
| T80% | Time required to reach an uptake of 80% of U20 starting at 0 s ($t_0$) in s |
| K20 | Sample permeability at 20 minutes in cm² |
| Kmin | the minimum value of the permeability during the experiment in m² |
| Kmin/K20 | the ratio of Kmin and K20 |

The driving pressure is calculated from the hydro head as follows:

$$\Delta p = h \cdot G \cdot \rho = 4929.31 \text{ g/(cm·s}^{-2})$$

The caliper at each time $t_i$ is calculated as the difference of the caliper sensor reading at time $t_i$ and the reference reading without sample:

$$d_i = r_i - r_r \text{ [cm]}$$

For superabsorbent particles samples the caliper of the sample at time $t_i = 0$ ($d_0$) is used to evaluate the quality of the particle sprinkling.

An apparent sample density inside the cylinder can be in fact calculated as:

$$\rho_s^A = \frac{m}{d_0 \cdot A} \text{ [g/cm}^3\text{]}$$

If this apparent density inside the cylinder differs from the apparent density of the powder by more than ±40% the measurement has to be considered invalid and eliminated.

The apparent density can be measured according EDANA method 406.2-02 ("Superabsorbent materials—Polyacrylate superabsorbent powders—GRAVIMETRIC DETERMINATION OF DENSITY")

The rate of change with time of the balance reading at time $t_i$ is calculated as follows:

$$\frac{dm_{out}(t_i)}{dt} = \frac{m_{out_{i+1}} - m_{out_{i-1}}}{t_{i+1} - t_{i-1}} \text{ [g/sec]}$$

The rate of change with time of the caliper reading at time $t_i$ is calculated as follows:

$$\frac{dd(t_i)}{dt} = \frac{d_{i+1} - d_{i-1}}{t_{i+1} - t_{i-1}} \text{ [cm/sec]}$$

The uptake Kinetics is calculated as follows:

$$U(t_i) = \frac{(A \cdot d_i - V_s) \cdot \rho}{m} \text{ [g/g]}$$

By dry sample volume ($V_s$) is intended the skeletal volume of the sample therefore $V_s$ is the actual volume occupied by the solid material in the dry sample excluding pores and interstitials that might be present.

$V_s$ can be calculated or measured by different methods known by the skilled person for example, knowing the exact composition and the skeletal density of the components it can be determined as follows:

$$V_S = \sum_k V_k = \sum_k \frac{m_k}{\rho_{Sk}} \text{ [cm}^3\text{]}$$

Alternatively for an unknown material composition $V_s$ can be easily calculated as follow:

$$V_s = \frac{m}{\rho_S} \text{ [cm}^3\text{]}$$

The average density $\rho_s$ can be determined by pycnometry with a suitable non-swelling liquid of known density. This technique cannot be performed on the same samples subsequently used for the K(t) measure therefore a suitable additional representative set of samples should be prepared for this experiment measurement.

From U(t) at the different time steps calculated as explained above, one can determine the uptake at any specific time by linear interpolation. For example one of the important outputs is the uptake at 20 minutes also called U20 (in g/g).

From U(t) at the different time steps one can also determine the time required to reach a certain uptake by linear interpolation. The time where the uptake of 20 g/g is first reached is called T20. Similarly the time to reach any other uptakes can be calculated accordingly (e,g T5 or T10). Knowing U20 it is possible to determine from U(t) at the different time steps also the time to reach 80% of U20, this property is called T80%.

The Effective Permeability is calculated as follows from the rates of mass change and caliper change:

$$K(t_i) = \eta \frac{d_i}{\Delta p} \cdot \left( \frac{1}{\rho \cdot A} \cdot \frac{dm_{out}(t_i)}{dt} + \frac{dd(t_i)}{dt} \right) \text{[cm}^2\text{]}$$

The effective viscosity of the liquid depends on the temperature and in the interval of the experiment (23° C.±1° C.) is calculated according the following empirical equation:

$$\eta = -2.36 \cdot 10^{-4} \cdot T + 1.479 \cdot 10^{-2} \text{ [g/(cm s)]}$$

From $K(t_i)$ one can determine the effective permeability at a certain time by linear interpolation. For example one of the important outputs is the permeability at 20 minutes or K20 (cm²). Similarly the Permeability at any other time can be calculated accordingly (e.g. K5 or K10).

Another parameter to be derived from the data is Kmin, which is the minimum K(t) value measured over the whole curve in the interval from $t_i = 30$ s to $t_i = 1200$ s. This value is useful to calculate Kmin/K20 which is the ratio between the minimum effective permeability and the permeability at 20 minutes. This parameter express the temporary gel blocking that might occur in some of the samples. If the value is close to 1 there is no temporary gel blocking if the value is close to 0 it is an indication that the material goes through a strong effective permeability drop when initially loaded with liquid.

The average values for T20, T80%, K20, U20 and Kmin/K20 are reported from 3 replicates according to the accuracy required as known by the skilled man.

Centrifuge Retention Capacity (CRC)

The CRC measures the liquid absorbed by the superabsorbent polymer particles for free swelling in excess liquid. The CRC is measured according to EDANA method WSP 241.2-05.

Dry Absorbent Core Caliper Test

This test may be used to measure the caliper of the absorbent core (before use i.e. without fluid loading) in a standardized manner at the crotch point C' of the core or any other point.

Equipment: Mitutoyo manual caliper gauge with a resolution of 0.01 mm—or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second

Sample preparation: The core is conditioned at least 24 hours as indicated above.

Measurement procedure: The core is laid flat with the bottom side, i.e. the side intended to be placed towards the backsheet in the finished article facing down. The point of measurement (e.g. the crotch point C corresponding to this point in the finished article) is carefully drawn on the top side of the core taking care not to compress or deform the core.

The contact foot of the caliper gauge is raised and the core is placed flat on the base plate of the caliper gauge with the top side of the core up so that when lowered, the center of the foot is on the marked measuring point.

The foot is gently lowered onto the article and released (ensure calibration to "0" prior to the start of the measurement). The caliper value is read to the nearest 0.01 mm, 10 seconds after the foot is released.

The procedure is repeated for each measuring point. If there is a fold at the measuring point, the measurement is done in the closest area to this point but without any folds. Ten articles are measured in this manner for a given product and the average caliper is calculated and reported with an accuracy of one tenth mm.

Absorbent Article Caliper Test

The Absorbent Article Caliper Test can be performed as for the Dry Absorbent Core Caliper Test with the difference that the caliper of the finished absorbent article is measured instead of the caliper of the core. The point of measurement may be the intersection of the longitudinal axis (80) and transversal axis (90) of the absorbent article or the crotch point C of the article. If the absorbent articles were provided folded and/or in a package, the articles to be measured are unfolded and/or removed from the center area of the package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package, unfolded and conditioned. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles. Care is taken to avoid touching and/or compressing the area of measurement.

Speed of Absorption Test

This test quantifies the speed of absorption of saline solution at different times. The absorbent core to be tested is weighted to the nearest 0.1 g and the weight recorded as Dry Core Weight. The core is then immerged flat in a container containing an excess of 0.9% saline solution with the body-facing side of the core facing down in direct contact with liquid. The core is left in the solution for exactly 90 s. The core is then removed and the excess of saline is removed via gravity for 20 seconds by hanging the core vertically with the back edge of the core up. The wet core is then weighted again to the nearest 0.1 g and the weight recorded as the 90 s Wet Weight. The core is then laid flat again for 20 minutes on the lab bench with the body-facing side down.

At this point, the core is immerged again for 90 s in an excess of fresh 0.9% saline solution again with the body-facing side facing down. The core is then again hanged vertical from the back of the core for 20 seconds to let any excess solution drip. After this the core is weighted again to the nearest 0.1 g and the weight recorded as 180 s Wet Weight. The following values are then calculated from the data:

$$\text{Speed of absorption in g/s@90 s} = (90 \text{ s Wet Weight} - \text{Dry Core Weight})/90$$

$$\text{Speed of absorption in g/s@180 s} = (180 \text{ s Wet Weight} - \text{Dry Core Weight})/180$$

Mass Average Particle Size Via Sieve Test 10 g (weighed to an accuracy of at least 0.01 g) of a representative sample of the respective superabsorbent polymer particles or agglomerated superabsorbent polymer particles are sieved via sieves of about 10 cm in diameter (available e.g. from Retsch GmbH, Haan, Germany; DIN/ISO 3310-1). A stack of sieve with the following mesh sizes (sequence from top to bottom) is used: 850 µm, 800 µm, 710 µm, 600 µm, 500 µm, 425 µm, 300 µm, 212 µm, 150 µm, pan (taken herein as equivalent to 0 µm). The weight of each empty sieve is noted down, to an accuracy of 0.01 g.

The 10 g sample is loaded to the top sieve (i.e. 850 µm) and sieved via a sieve machine ("AS 400 control" available from Retsch GmbH, Haan, Germany) for 3 min at 250 rpm. The weight of each sieve after sieving is noted down, to an accuracy of 0.01 g. The difference between the weight of loaded sieve and the empty sieve for each size gives the weight of particles per mesh size.

As size of the sieve $D_i$ the sieve notation is taken, e.g. on sieve 500 µm is the fraction with D500 to an amount of m500, with D500=500 µm.

The mass average particle size (mAvPS) herein is calculated as $$mAvPS = \frac{\sum_i m_i \cdot D_i}{m_{total}} \text{ with } m_{total} = \sum_i m_i$$

EXPERIMENTALS

Example of SAP Preparation: SAP1

Examples SAP1, SAP2 and SAP3 below exemplify the preparation of SAP having a T20 below 240 s. The process for making these superabsorbent polymer particles can be summarize as comprising the subsequent steps of:
providing a polyacrylic acid polymer gel; preferably wherein the acrylic acid monomers have been polymerized at 50% to 95% neutralization, typically using NaOH to raise the pH;
submitting the gel to a first grinding process and drying the gel to obtain a base polymer;
rewetting, grinding, drying and sieving the resulting material,
optionally making a post-treatment of the resulting superabsorbent particles such as surface cross-linking the superabsorbent particles.

Other examples of method for making SAP having a T20 below 240 s are disclosed in WO2012/174,026A1. The fourth, comparative, example SAP4 exemplifies the making of SAP having a T20 of 341 s and did not have the re-wetting step.

The first SAP example (SAP1) was made by preparing a polyacrylic acid base polymer, followed by a rewet and grinding step and a further surface cross-linking step. In more details, the base polymer can be obtained according to the following procedure.

A 20000 ml resin kettle (equipped with a four-necked glass cover closed with septa, suited for the introduction of a thermometer, syringe needles) is charged with about 1.5 kg ice (1458.19 g) (prepared from de-ionized water). Typically, a magnetic stirrer, capable of mixing the whole content (when liquid), is added. An amount of glacial acrylic acid (AA) (appr. 423 g) is taken from 4000.00 g AA (for synthesis, from Merck) to dissolve 25.68 g MethyleneBisAcrylAmide (MBAA) (for molecular biology, for electrophoresis from Sigma Aldrich). The remaining AA is added to the ice in 6 portions of about 250-1060 g while stirring is continued. A thermometer is introduced and 3330.56 g 50% NaOH solution (for analysis, from Merck) and 5944.72 g ice (prepared from de-ionized water) are added as follows such that the temperature is in the range of 15-25° C.: The NaOH is added to the ice/AA mixture in 8 portions of about 215-550 g with addition of ice in 7 portions of about 420-1510 g between the addition of NaOH and addition of 965.52 g deionized water after about half of the NaOH solution is added. The MBAA solution is added to the mixture while stirring is continued. Deionized water (the required amount to achieve in total 12639.70 g (ice+water) minus the amount to dissolve the initiator "V50") is added. Then, the resin kettle is closed, and a pressure relief is provided e.g. by puncturing two syringe needles through the septa. The solution is then purged vigorously with argon via an 80 cm injection needle while stirring at about 400-1200 RPM. The argon stream is placed close to the stirrer for efficient and fast removal of dissolved oxygen. After about 120 min of Argon purging and stirring 4064 mg initiator "V50" (=2,2'-azobis (N,N'-dimethyleneisobutyramidine) dihydrochloride, from Waco Chemicals) dissolved in appr. 89.74 g deionized water is added to the reaction mixture while stirring and Argon purging is continued. After the initiator solution is mixed with the reaction mixture (typically about 3-5 min stirring and Argon purging), two photo lamps (e.g. Kaiser ProVision 2.55 HF equipped with 2 lamps Osram Dulux L 55 W/830) are placed on either side of the vessel. The solution typically starts to become turbid or a sudden increase in viscosity is observed after about 5-20 min, typically at temperatures about room temperature. Then, the argon injection needle is raised above the surface of the gel and purging with argon is continued at a reduced flow rate. The temperature is monitored; typically it rises from about 20° C. to about 60-75° C. within 60-120 minutes. Once the temperature reaches about 60° C. or after about 105 min after the reaction mixture becomes turbid or viscous, the lamps are switched off. Once the temperature starts to drop, the resin kettle is transferred into a circulation oven (e.g. Binder FED 720) and kept at about 60° C. for 15-18 hours. After this time, the resin kettle is allowed to cool at room temperature to about 20-40° C., and the gel is removed and broken manually or cut with scissors into smaller pieces. The gel is grinded with a grinder (e.g. meat grinder X70G from Sharpen with Unger R70 plate system equipped with pre-cutter kidney plate with straight holes at 17 mm diameter), put onto perforated stainless steel dishes (hole diameter 4.8 mm, 50 cm×50 cm, 0.55 mm caliper, 50% open area, from RS) and transferred into a circulation oven (Binder FED 720) at about 80° C. for about 20 hours, resulting in base polymer 1.

The base polymer 1 thus obtained can then be wet grinded according to the following process. 800.2 g of dried and grinded polymer resulting from the synthesis above were added to a 3000 ml glass beaker. A mixture of 801.3 g of dionized water and 50 ml Ethanol (e.g. for analysis from Merck) was quickly added to the glass beaker and the mixture was stirred quickly manually with a large lab spoon for about 5 mins. After the mixing, the wetted base polymer was kept in the glass beaker for another 30 mins. Following, the polymer mixture was grinded three times through 3 connected mincer plates (e.g. meat grinder X70G from Sharpen with Unger R70 plate system equipped with a) pre-cutter kidney plate with straight holes at 17 mm diameter, b) plate with 20 8 mm diameter holes and c) plate with 176 3 mm diameter holes). The feeding rate for grinding was about 300-600 g per minute. During grinding, the wetted polymer heats up and water and ethanol evaporates resulting in 498.2 g wetted and grinded base polymer. The wetted and grinded polymer is spread on a 50×50 cm perforated stainless steel dish (5 mm diameter) and dried in a circulation over at 120° C. for 12 hrs. The resulting dried polymer is broken manually and ground with a cutting-grinding mill (e.g. IKA MF 10 basic grinding drive with the MF 10.1 cutting-grinding head and an outlet sieve with 1.5 mm diameter holes) and sieved to 150-710 µm (e.g. with AS 400 control from Retsch). The fraction above 710 µm is ground again through the cutting-grinding mill through an outlet sieve with 1.0 mm diameter holes and again sieved through 150-710 µm. The grinding and sieving yields in 584.2 g grinded base polymer 1 particles of 150-710 µm.

The grinded base polymer 1 particles can then be surface cross-linked as follows. 500.0 g grinded superabsorbent base polymer 1 is added to a Lödige Ploughshare Laboratory Mixer, Type L5 and mixed at rotary speed setting 6. 30.05 g of Al lactate solution (15 w % Al lactate in deionized water (Aluminium L-lactate 95% from Sigma-Aldrich)) is added via the peristaltic pump (e.g. Ismatec MCP Standard with Tygon MHLL tube, inner diameter e.g. 1.52 mm) via a spray nozzle (spray nozzle of Mini Spray Dryer B-290 from Büchi with nozzle disc diameter 1.5 mm) at a spray pressure of about 2 bar, at a flow rate of about 3 g solution/min, at a starting temperature of about 23° C. After about 10 min the addition of Al lactate is completed, at a temperature of about 24° C. After Al solution addition is completed, 5.01 g of Denacol EX 810 solution (16 w % solution of Denacol EX 810 (=EthyleneGlycolDiGlycidylEther=EGDGE) from Nagase in 1,2-propanediol (suitable for use as excipient, from Merck)) is added via the peristaltic pump and the spray nozzle at a spray pressure of about 2 bar at a flow rate of about 3 g solution/min. During the addition of the Denacol EX 810 solution, the temperature stays in the range of about 23° C. After the addition is completed after about 2 min, 62.5 g of deionized water is added via the peristaltic pump and the spray nozzle at a spray pressure of about 2 bar at a flow rate of about 10 g solution/min. During the addition of the deionized water, the temperature stay at about room temperature. After about 7 min the addition of deionized water is completed. Then, the bottom outlet of the Lödige mixer is opened and the material that comes out of the bottom outlet pushed out only by the Ploughshare mixer rotation is collected and evenly distributed onto two Teflon coated baking trays (e.g. Kaiser 7509960, 41×31×10 cm). The baking trays are covered with aluminum foil and maintained at room temperature for about 15-18 hours. After that the covered baking trays are heated at 120° C. for 2 h 20 min in the oven (e.g. Binder APT.Line FD 240). After the heating time, the baking trays are taken out of the oven, the aluminium foil is cut, so about 3-6 slits of about 3 cm length and about 3 mm width are created. The samples are put under a fume hood and let cool down to room temperature. Afterwards, the samples are manually broken and sieved to 150-710 µm (with sieves DIN/ISO 3310-1 e.g. from Retsch) to get the final material SAP1 in yield of 379.4 g.

Examples of SAP Preparation: SAP2

SAP2 was made starting from the base polymer 1 used for making SAP1 as described above. The further wet grinding and surface cross-linking steps were then conducted as follows. 1998.5 g of dried and grinded base polymer 1 were added to a 5000 ml glass beaker and 2000 ml dionized water was quickly added to the glass beaker. The mixture was stirred quickly manually with a large lab spoon for about 10 mins. After the mixing, the wetted base polymer was kept in the glass beaker for another 30 mins. Following, the polymer mixture was grinded four times through a meat grinder (e.g. meat grinder X70G from Sharpen with Unger R70 plate system equipped with a) plate with 20 8 mm diameter holes, b) 3 shafted cutter knife and c) plate with 176 3 mm diameter holes). The feeding rate for grinding was about 300-600 g per minute. During grinding, the wetted polymer heats up and water evaporates. The wetted and grinded polymer is spread on three 50×50 cm perforated stainless steel dish (5 mm diameter) and dried in a circulation over at 120° C. for 12 hrs. The resulting dried polymer is broken manually and ground with a cutting-grinding mill (e.g. IKA MF 10 basic grinding drive with the MF 10.1 cutting-grinding head and an outlet sieve with 1.0 mm diameter holes) and sieved to 150-710 µm (e.g. with AS 400 control from Retsch). The fraction above 710 µm is ground again through the cutting-grinding mill and sieved. The grinding and sieving yields in 1348.4 g grinded base polymer 2 of 150-710 µm, which was cross-linked as follows.

600.3 g grinded superabsorbent base polymer 2 is added to a Lödige Ploughshare Laboratory Mixer, Type L5 and mixed at rotary speed setting 6. 27.9 g of Al lactate solution (15 w % Al lactate in deionized water (Aluminium L-lactate 95% from Sigma-Aldrich)) is added via the peristaltic pump (e.g. Ismatec MCP Standard with Tygon MHLL tube, inner diameter e.g. 1.52 mm) via a spray nozzle (spray nozzle of Mini Spray Dryer B-290 from Büchi with nozzle disc diameter 1.5 mm) at a spray pressure of about 2 bar, at a flow rate of about 3 g solution/min, at room temperature. After about 9 min the addition of Al lactate is completed. After Al solution addition is completed, 4.88 g of Denacol EX 810 solution (16 w % solution of Denacol EX 810 (=EthyleneGlycolDiGlycidylEther=EGDGE) from Nagase in 1,2-propanediol (suitable for use as excipient, from Merck)) is added via the peristaltic pump and the spray nozzle at a spray pressure of about 2 bar at a flow rate of about 3 g solution/min. During the addition of the Denacol EX 810 solution, the temperature stays around room temperature. After the addition is completed after about 2 min, 75.2 g of deionized water is added via the peristaltic pump and the spray nozzle at a spray pressure of about 2 bar at a flow rate of about 10 g solution/min. During the addition of the deionized water, the temperature rises to about 26° C. After about 7 min the addition of deionized water is completed. Then, the bottom outlet of the Lödige mixer is opened and the material that comes out of the bottom outlet pushed out by the Ploughshare mixer rotation is collected and evenly distributed onto one Teflon coated baking tray (e.g. Kaiser 7509960, 41×31×10 cm). Afterwards, the mixer is opened all other material is removed from the mixer and placed onto another Teflon coated baking tray. The baking trays are covered with aluminum foil and maintained at room temperature for about 14 hours. After that the covered baking trays are heated at 180° C. for 2 h in the oven (e.g. Binder APT.Line FD 240). After the heating time, the baking trays are taken out of the oven, the aluminium foil is cut, so about 3-6 slits of about 3 cm length and about 3 mm width are created. The samples in the baking trays are put under a fume hood and let cool down to room temperature. The samples are manually broken and sieved to 150-710 µm (with sieves DIN/ISO 3310-1 e.g. from Retsch) to get the final material SAP2 in yield of 503.2 g.

Example of SAP Preparation: SAP3

This SAP was made as SAP2 except for the surface crosslinking of the grinded base polymer which was made as follows. 600.4 g grinded superabsorbent base polymer 2 is added to a Lödige Ploughshare Laboratory Mixer, Type L5 and mixed at rotary speed setting 6. 35.8 g of Al lactate solution (15 w % Al lactate in deionized water (Aluminium L-lactate 95% from Sigma-Aldrich)) is added via the peristaltic pump (e.g. Ismatec MCP Standard with Tygon MHLL tube, inner diameter e.g. 1.52 mm) via a spray nozzle (spray nozzle of Mini Spray Dryer B-290 from Büchi with nozzle disc diameter 1.5 mm) at a flow rate of about 3 g solution/min, at room temperature. After about 12 min the addition of Al lactate is completed. After Al solution addition is completed, 4.5 g of Denacol EX 810 solution (16 w % solution of Denacol EX 810 (=Ethylene-GlycolDiGlycidylEther=EGDGE) from Nagase in 1,2-propanediol (suitable for use as excipient, from Merck)) is added via the peristaltic pump and the spray nozzle at a flow rate of about 3 g solution/min. During the addition of the Denacol EX 810 solution, the temperature stays around room temperature. After the addition is completed after about 2 min, 76.2 g of deionized water is added via the peristaltic pump and the spray nozzle at a flow rate of about 10 g solution/min. During the addition of the deionized water, the temperature rises to about 25° C. After about 7 min the addition of deionized water is completed. Then, the Lödige mixer is opened all other material is removed from the mixer and placed onto two Teflon coated baking trays (e.g. Kaiser 7509960, 41×31×10 cm). The baking trays are covered with aluminum foil and maintained at room temperature for about 14 hours. After that the covered baking trays are heated at 180° C. for 2 h in the oven (e.g. Binder APT.Line FD 240). After the heating time, the baking trays are taken out of the oven, the aluminium foil is cut, so about 3-6 slits of about 3 cm length and about 3 mm width are created. The samples in the baking trays are put under a fume hood and let cool down to room temperature. The samples are manually broken and sieved to 150-710 μm (with sieves DIN/ISO 3310-1 e.g. from Retsch) to get the final SAP3 in yield of 512.8 g.

Examples SAP1, SAP2 and SAP3 all had a T20 below 240 s. Comparative example SAP4 below describes a SAP having a T20 above 240 s.

Example of SAP Preparation: Comparative SAP4

The comparative SAP (SAP4) was made according the following steps, which comprised a polymerization step and a surface cross-linking step. A 20000 ml resin kettle (equipped with a four-necked glass cover closed with septa, suited for the introduction of a thermometer, syringe needles) is charged with about 3 kg ice (2921.94 g) (prepared from de-ionized water). Typically, a magnetic stirrer, capable of mixing the whole content (when liquid), is added. 1178.26 g 50% NaOH solution (for analysis, from Merck) is added to the ice and the resulting slurry is stirred. Another portion of 647.81 g ice (prepared from de-ionized water) is added to the stirred slurry. Subsequently, 2152.34 g 50% NaOH solution (for analysis, from Merck) is added to the stirred slurry, typically in portions of about 600-650 g. An amount of glacial acrylic acid (AA) (appr. 481 g) is taken from 4000.02 g AA (for synthesis, from Merck) to dissolve 25.68 g MethyleneBisAcrylAmide (MBAA) (for molecular biology, for electrophoresis from Sigma Aldrich). The MBAA solution is added to the mixture. A thermometer is introduced and the remaining AA and ice are added as follows such that the temperature is in the range of 15-25° C.: The remaining AA is added to the ice/NaOH mixture in 8 portions of about 210-715 g with addition of 6145.77 g ice (prepared from de-ionized water) in 6 portions of about 770-1600 g between the addition of AA while stirring is continued. Deionized water (the required amount to achieve in total 12639.80 g (ice+water) minus the amount to dissolve the initiator "V50") is added. Then, the resin kettle is closed, and a pressure relief is provided e.g. by puncturing two syringe needles through the septa. The solution is then purged vigorously with argon via an 80 cm injection needle while stirring at about 400-1200 RPM. The argon stream is placed close to the stirrer for efficient and fast removal of dissolved oxygen. After about 60 min of Argon purging and stirring 4014 mg initiator "V50" (=2,2'-azobis (N,N'-dimethyleneisobutyramidine) dihydrochloride, from Waco Chemicals) dissolved in appr. 36.45 g deionized water is added to the reaction mixture while stirring and Argon purging is continued. After the initiator solution is mixed with the reaction mixture (typically about 3-5 min stirring and Argon purging), two photo lamps (e.g. Kaiser ProVision 2.55 HF equipped with 2 lamps Osram Dulux L 55 W/830) are placed on either side of the vessel. The solution typically starts to become turbid or a sudden increase in viscosity is observed after about 5-20 min, typically at temperatures about room temperature. Then, the argon injection needle is raised above the surface of the gel and purging with argon is continued at a reduced flow rate. The temperature is monitored; typically it rises from about 20° C. to about 60-70° C. within 60-120 minutes. Once the temperature reaches about 60° C. or after about 105 min after the reaction mixture becomes turbid or viscous, the lamps are switched off. Once the temperature starts to drop, the resin kettle is transferred into a circulation oven (e.g. Binder FED 720) and kept at about 60° C. for 15-18 hours. After this time, the resin kettle is allowed to cool at room temperature to about 20-40° C., and the gel is removed and broken manually or cut with scissors into smaller pieces. The gel is grinded with a grinder (e.g. meat grinder X70G from Sharpen with Unger R70 plate system equipped with pre-cutter kidney plate with straight holes at 17 mm diameter), put onto perforated stainless steel dishes (hole diameter 4.8 mm, 50 cm×50 cm, 0.55 mm caliper, 50% open area, from RS) and transferred into a circulation oven (Binder FED 720) at about 80° C. for about 40 hours. Once the gel has reached a constant weight (usually 2 days drying), it is ground using a centrifuge mill (e.g. Retsch ZM 200 with vibratory feeder DR 100, interchangeable sieve with 1.5 mm opening settings, rotary speed 8000 RPM), and sieved to 150-850 μm (e.g. with AS 400 control from Retsch, with sieves DIN/ISO 3310-1 e.g. from Retsch). The remaining fraction >850 μm is again milled and sieved to 150-850 μm. Typically, the milling step is repeated with remaining fractions >850 μm about 1-3 times. All fractions 150-850 μm are collected and combined to form the base polymer sample. In case the residual moisture is more than about 6% by weight, the sample is again dried, e.g. in a circulation oven (e.g. Binder FED 720) at about 80° C. for about 5 hours. This drying step might be repeated until the residual moisture is about 6% by weight or lower, e.g. about 1-5%, yielding comparative base polymer 2.

The obtained comparative base polymer 2 can then surface cross-linked to obtain comparative SAP4. 1000.11 g superabsorbent base polymer 2 as above is added to a Lödige Ploughshare Laboratory Mixer, Type L5 and mixed at rotary speed setting 6. 60.05 g of Al lactate solution (15 w % Al lactate in deionized water (Aluminium L-lactate 95% from Sigma-Aldrich)) is added via the peristaltic pump (e.g. Ismatec MCP Standard with Tygon MHLL tube, inner diameter e.g. 1.52 mm) via a spray nozzle (spray nozzle of Mini Spray Dryer B-290 from Büchi with nozzle disc diameter 1.5 mm) at a spray pressure of about 2 bar, at a flow rate of about 3 g solution/min, at a starting temperature of about 30° C. After about 20 min the addition of Al lactate is completed, at a temperature of about 35° C. After Al solution addition is completed, 9.99 g of Denacol EX 810 solution (16 w % solution of Denacol EX 810 (=Ethylene-GlycolDiGlycidylEther=EGDGE) from Nagase in 1,2-propanediol (suitable for use as excipient, from Merck)) is added via the peristaltic pump and the spray nozzle at a spray pressure of about 2 bar at a flow rate of about 3 g solution/min. During the addition of the Denacol EX 810 solution, the temperature is in the range of about 32° C. After the addition is completed after about 4 min, 125 g of deionized water is added via the peristaltic pump and the spray nozzle at a spray pressure of about 2 bar at a flow rate of about 10 g solution/min. During the addition of the deionized water, the temperature is in the range of about 32° C. After about 12.5 min the addition of deionized water is completed. Then, the bottom outlet of the Lödige mixer is opened and the material that comes out of the bottom outlet pushed out only by the Ploughshare mixer rotation is collected and evenly distributed onto two Teflon coated baking trays (e.g. Kaiser 7509960, 41×31×10 cm). The baking trays are covered with aluminum foil and maintained at room temperature for about 15-18 hours. After that the covered baking trays are heated at 120° C. for 2 h 20 min in the oven (e.g. Binder APT.Line FD 240). After the heating time, the baking trays are taken out of the oven, the aluminium foil is cut, so about 3-6 slits of about 3 cm length and about 3 mm width are created. The samples are put under a fume hood and let cool down to room temperature. Afterwards, the samples are manually broken and sieved to 150-850 um (with sieves DIN/ISO 3310-1 e.g. from Retsch) to get the final comparative SAP4.

Base Polymer 3:

A 20 000 ml resin kettle (equipped with a four-necked glass cover closed with septa, suited for the introduction of a thermometer, syringe needles) is charged with about 5089.0 g of ice (ca. 30-40% of the total amount of ice: 12128.0 g ice prepared from deionized water). A magnetic stirrer, capable of mixing the whole content (when liquid), is added and stirring is started.

An 45.7 g of deionized water is taken to dissolve 4.516 g of "V50" (=2,2'-azobis (N,N'-dimethyleneisobutyramidine) dihydrochloride, from Waco Chemicals) e.g. in a glass vessel with plastic snap-on cap. The vessel with the "V50" solution is closed and set aside in a fridge at about 4° C.

312.5 g of glacial acrylic acid (AA; e.g. Acrylic Acid for synthesis, from Merck) is taken from the total amount of 4000.1 g AA to dissolve 25.67 g of MBAA e.g. in a glass beaker. The beaker with the MBAA solution is covered e.g. with parafilm and set aside.

The remaining AA is added to the ice in the resin kettle while stirring is continued.

A thermometer is introduced and in total 3330.7 g of 50% NaOH solution (for analysis, from Merck) and the remaining amount of ice (prepared from de-ionized water) are added subsequently in portions such that the temperature is in the range of about 15-30° C.

The MBAA solution is added to the mixture of AA, NaOH solution and ice at a temperature of about 15-30° C. while stirring is continued. The beaker that contained the MBAA solution is washed 2× with deionized water in an amount of about 10% of the MBAA solution volume per wash. The wash water of both washing steps is added to the stirred mixture.

Deionized water (the remaining amount required to achieve the total amount of (ice+water) of 12639.3 g minus the amount to wash the "V50" containing vessel 2× with deionized water in an amount of about 10% of the "V50" solution volume per wash) is added to the stirred mixture.

Then, the resin kettle is closed, and a pressure relief is provided e.g. by puncturing two syringe needles through the septa. The solution is then purged vigorously with argon via an 80 cm injection needle at about 0.4 bar while stirring at about 400-1200 RPM. The argon stream is placed close to the stirrer for efficient and fast removal of dissolved oxygen.

After about min 1 hour and max 2 hours of Argon purging and stirring the "V50" solution is added to the reaction mixture at a temperature of about 20-25° C. via a syringe while stirring and Argon purging is continued. The vessel that contained the "V50" solution is washed 2× with deionized water in an amount of about 10% of the "V50" solution volume per wash. The wash water of both washing steps is added to the stirred mixture via a syringe through the septa.

After the initiator solution is mixed with the reaction mixture, stirring and Argon purging is continued for about 5 min. After that, while the reaction mixture has a temperature of about 20-25° C., two photo lamps (Kaiser ProVision 2.55 HF equipped with 2 lamps Osram Dulux L 55 W/830, at max. intensity) are placed on either side of the vessel and switched on. The solution typically starts to become turbid or a sudden increase in viscosity is observed after about 5-20 min, typically at temperatures about room temperature. Then, the argon injection needle is raised above the surface of the gel and purging with argon is continued at a reduced flow rate (0.2 bar).

The temperature is monitored; typically it rises from about 23° C. to about 60° C. within 60 minutes. Once the temperature reaches about 60° C., the lamps are switched off. Once the temperature starts to drop, the resin kettle is transferred into a circulation oven (Binder FED 720) and kept at about 60° C. for about 18 hours.

After this time, the oven is switched off and the resin kettle is allowed to cool down to about 20-40° C. while remaining in the oven. After that, the gel is removed and broken manually or cut with scissors into smaller pieces. The gel is grinded with a grinder (X70G from Scharfen with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720) at about 105° C. for about 18 hours.

The residual moisture of the dried gel is about 6.2% by weight.

In four baking trays (e.g. e.g. Kaiser 7509960, 41×31×10 cm) an amount of the dried gel per tray is placed and an amount of deionized water (see table below) is added at once and the solution manually stirred for about 10 mins.

|  | Tray 1 | Tray 2 | Tray 3 | Tray 4 |
|---|---|---|---|---|
| AGM amount | 1500.1 g | 1500.1 g | 1500.2 g | 714.5 g |
| Water amount | 3000.0 g | 3000.1 g | 3005.0 g | 1430.6 g |

After the mixing, the wetted base polymer was kept in the trays for another 30 mins. Following, the wetted base polymer of the four trays is combined and grinded four times through a meat grinder (Grinder X70G from Sharpen with Unger R70 plate system equipped with a) plate with 20 8 mm diameter holes, b) 3 shafted cutter knife and c) plate with 176 3 mm diameter holes). The feeding rate for grinding was about 300-600 g per minute. During grinding, the wetted polymer heats up and water evaporates. The wetted and grinded polymer is spread on several 50×50 cm perforated stainless steel dish (hole diameter 4.8 mm, 50 cm×50 cm, 0.55 mm caliper, 50% open area, from RS) at max gel height of about 3 cm and dried in a circulation oven (Binder FED 720) at 105° C. for 18 hours and subsequently for 2.5 hours at 105° C. and for 14 hours in an vacuum oven (e.g. Vacutherm, VT6130 P-BL, Heraeus equipped with vapour trap e.g. Titan Vapor Trap, Kinetics, and/or equipped with vacuum pump e.g. Trivac®, Leybold) at 80° C. at max. about 80 mbar.

The residual moisture of the dried gel is about 3.1% by weight.

The dried gel is then ground using a centrifuge mill (Retsch ZM 200 with vibratory feeder DR 100 (setting 50-60), interchangeable sieve with 1.5 mm opening settings, rotary speed 8000 rpm). The milled polymer is again dried in an oven (e.g. Binder APT.Line FD 240) for 12 hours at 120° C. and then sieved via a sieving machine (AS 400 control from Retsch with sieves DIN/ISO 3310-1 at about 200-280 rpm for about for 5-10 min) to the following particle size cuts with the following yields:

| Code  | BP 3.1   | BP 3.2     | BP 3.3     | BP 3.4     | BP 3.5     | BP 3.6   |
|-------|----------|------------|------------|------------|------------|----------|
| cut   | <150 μm  | 150-300 μm | 300-425 μm | 425-600 μm | 600-710 μm | >710 μm  |
| Yield | 1026.9 g | 1217.0 g   | 876.1 g    | 769.9 g    | 447.1 g    | 789.9 g  |

Base Polymer 4:

A 20 000 ml resin kettle (equipped with a four-necked glass cover closed with septa, suited for the introduction of a thermometer, syringe needles) is charged with about 5388.3 g of ice (ca. 30-45% of the total amount of ice: 12149.9 g ice prepared from deionized water). A magnetic stirrer, capable of mixing the whole content (when liquid), is added and stirring is started.

An 43.0 g of deionized water is taken to dissolve 4.516 g of "V50" (=2,2'-azobis (N,N'-dimethyleneisobutyramidine) dihydrochloride, from Waco Chemicals) e.g. in a glass vessel with plastic snap-on cap. The vessel with the "V50" solution is closed and set aside in a fridge at about 4° C.

299.5 g of glacial acrylic acid (AA; e.g. Acrylic Acid for synthesis, from Merck) is taken from the total amount of 4000.7 g AA to dissolve 25.67 g of MBAA e.g. in a glass beaker. The beaker with the MBAA solution is covered e.g. with parafilm and set aside.

The remaining AA is added to the ice in the resin kettle while stirring is continued.

A thermometer is introduced and in total 3330.6 g of 50% NaOH solution (for analysis, from Merck) and the remaining amount of ice (prepared from de-ionized water) are added subsequently in portions such that the temperature is in the range of about 15-30° C.

The MBAA solution is added to the mixture of AA, NaOH solution and ice at a temperature of about 15-30° C. while stirring is continued. The beaker that contained the MBAA solution is washed 2× with deionized water in an amount of about 10% of the MBAA solution volume per wash. The wash water of both washing steps is added to the stirred mixture.

Deionized water (the remaining amount required to achieve the total amount of (ice+water) of 12639.3 g minus the amount to wash the "V50" containing vessel 2× with deionized water in an amount of about 10% of the "V50" solution volume per wash) is added to the stirred mixture.

Then, the resin kettle is closed, and a pressure relief is provided e.g. by puncturing two syringe needles through the septa. The solution is then purged vigorously with argon via an 80 cm injection needle at about 0.4 bar while stirring at about 400-1200 RPM. The argon stream is placed close to the stirrer for efficient and fast removal of dissolved oxygen.

After about min 1 hour and max 2 hours of Argon purging and stirring the "V50" solution is added to the reaction mixture at a temperature of about 20-25° C. via a syringe while stirring and Argon purging is continued. The vessel that contained the "V50" solution is washed 2× with deionized water in an amount of about 10% of the "V50" solution volume per wash. The wash water of both washing steps is added to the stirred mixture via a syringe through the septa.

After the initiator solution is mixed with the reaction mixture, stirring and Argon purging is continued for about 5 min. After that, while the reaction mixture has a temperature of about 20-25° C., two photo lamps (Kaiser ProVision 2.55 HF equipped with 2 lamps Osram Dulux L 55 W/830, at max. intensity) are placed on either side of the vessel and switched on. The solution typically starts to become turbid or a sudden increase in viscosity is observed after about 5-20 min, typically at temperatures about room temperature. Then, the argon injection needle is raised above the surface of the gel and purging with argon is continued at a reduced flow rate (0.2 bar).

The temperature is monitored; typically it rises from about 23-24° C. to about 60° C. within 60 minutes. Once the temperature reaches about 60° C., the lamps are switched off. Once the temperature starts to drop, the resin kettle is transferred into a circulation oven (Binder FED 720) and kept at about 60° C. for about 18 hours.

After this time, the oven is switched off and the resin kettle is allowed to cool down to about 20-40° C. while remaining in the oven. After that, the gel is removed and broken manually or cut with scissors into smaller pieces. The gel is grinded with a grinder (X70G from Scharfen with Unger R70 plate system: 3 pre-cutter kidney plates with straight holes at 17 mm diameter), put onto perforated stainless steel dishes (hole diameter 4.8 mm, 50 cm×50 cm, 0.55 mm caliper, 50% open area, from RS; max. height of gel before drying: about 3 cm) and transferred into a circulation oven (Binder FED 720) at about 120° C. for about 20 hours.

The residual moisture of the dried gel is about 5.8% by weight.

In four baking trays (e.g. e.g. Kaiser 7509960, 41×31×10 cm) an amount of the dried gel per tray is placed and an amount of deionized water (see table below) is added at once and the solution manually stirred for about 10 mins.

|              | Tray 1   | Tray 2   | Tray 3   | Tray 4   |
|--------------|----------|----------|----------|----------|
| AGM amount   | 1500.1 g | 1500.4 g | 1500.1 g | 675.7 g  |
| Water amount | 3000.1 g | 3002.1 g | 3000.1 g | 1353.8 g |

After the mixing, the wetted base polymer was kept in the trays for another 30 mins. Following, the wetted base polymer of the four trays is combined and grinded four times through a meat grinder (Grinder X70G from Sharpen with Unger R70 plate system equipped with a) plate with 20 8 mm diameter holes, b) 3 shafted cutter knife and c) plate with 176 3 mm diameter holes). The feeding rate for grinding was about 300-600 g per minute. During grinding, the wetted polymer heats up and water evaporates. The wetted and grinded polymer is spread on several 50×50 cm perforated stainless steel dish (hole diameter 4.8 mm, 50 cm×50 cm, 0.55 mm caliper, 50% open area, from RS) at max gel height of about 3 cm and dried in a circulation oven (Binder FED 720) at 120° C. for 20 hours.

The residual moisture of the dried gel is about 2.7% by weight.

The dried gel is then ground using a centrifuge mill (Retsch ZM 200 with vibratory feeder DR 100 (setting 50-60), interchangeable sieve with 1.5 mm opening settings, rotary speed 8000 rpm). The milled polymer is again dried in an oven (e.g. Binder APT.Line FD 240) for 12 hours at 120° C. and then sieved via a sieving machine (AS 400 control from Retsch with sieves DIN/ISO 3310-1 at about 200-280 rpm for about for 5-10 min) to the following particle size cuts with the following yields:

| Code  | BP 4.1   | BP 4.2     | BP 4.3     | BP 4.4     | BP 4.5     | BP 4.6   |
|-------|----------|------------|------------|------------|------------|----------|
| cut   | <150 μm  | 150-300 μm | 300-425 μm | 425-600 μm | 600-710 μm | >710 μm  |
| yield | 996.4 g  | 1128.8 g   | 822.8 g    | 829.3 g    | 419.2 g    | 750.3 g  |

The surface-crosslinked and agglomerated superabsorbent polymers SAP 5-9 were made as follows:

600.0 g base polymer (see table) is added to a Lödige Ploughshare Laboratory Mixer, Type L5 and mixed at rotary speed setting 6. The amount of Al lactate solution (see table) (15 w % Al lactate in deionized water (Aluminium L-lactate 95% from Sigma-Aldrich)) is added via the peristaltic pump (e.g. Ismatec MCP Standard with Tygon MHLL tube, inner diameter e.g. 1.52 mm) via a spray nozzle (spray nozzle of Mini Spray Dryer B-290 from Büchi with nozzle disc diameter 1.5 mm) at a spray pressure of about 2 bar, at a flow rate of about 4.3 g solution/min, at a starting temperature of about 23° C. After about 12.5 min the addition of Al lactate is completed. After Al solution addition is completed, the liquid hose is disconnected, cleaned and flushed with Denacol solution (solution of Denacol EX 810 (=EthyleneGlycolDiGlycidylEther=EGDGE) from Nagase in 1,2-propanediol (suitable for use as excipient, from Merck)—see table below) and connected to the spraying unit.

The amount of Denacol EX 810 solution (see table) is added via the peristaltic pump and the spray nozzle at a spray pressure of about 2 bar at a flow rate of about 4.0 g solution/min. After the addition of Denacol EX 810 solution is completed, the liquid hose is disconnected, cleaned and flushed with deionized water and connected again to the spraying unit. After that, the amount of deionized water (see table) is added via the peristaltic pump and the spray nozzle at a spray pressure of about 2 bar at a flow rate of about 13.6 g solution/min. After the addition of deionized water is completed, the bottom outlet of the Lödige mixer is opened and the material that comes out of the bottom outlet pushed out only by the Ploughshare mixer rotation is collected and evenly distributed onto Teflon coated baking trays (e.g. Kaiser 7509960, 41×31×10 cm) into layers of about 2-3 cm thickness. The baking trays are covered with aluminum foil and maintained at room temperature for about 20-24 hours. After that the covered baking trays are heated at 120° C. for 2 h 20 min in the oven (e.g. Binder APT.Line FD 240). After the heating time, the baking trays are taken out of the oven, the aluminium foil is cut, so about 3-6 slits of about 3 cm length and about 3 mm width are created. The samples are put under a fume hood and let cool down to room temperature. Afterwards, the samples are manually broken and sieved (with sieves DIN/ISO 3310-1 e.g. from Retsch) to get the final materials as seen in the table below.

| Final Code | SAP 5 | SAP 6 | SAP 7 | SAP 8 | SAP 9 | SAP 10 |
|---|---|---|---|---|---|---|
| BP code | BP 3.1 | BP 4.1 | BP 4.2 | BP 3.2 | 1:1 mix of BP 3.2 & 4.2 | 1:1 mix of BP 3.3 & 4.3 |
| Al lactate solution | 72.06 | 54.03 g | 54.03 g | 72.02 g | 54.01 g | 54.03 g |
| Concentration (w %) of Denacol EX 810 solution | 24 w % | 24 w % | 24 w % | 24 w % | 16 w % | 16 w % |

-continued

| Final Code | SAP 5 | SAP 6 | SAP 7 | SAP 8 | SAP 9 | SAP 10 |
|---|---|---|---|---|---|---|
| Denacol EX 810 solution | 6.05 | 6.01 g | 6.04 g | 6.00 g | 6.02 g | 6.04 g |
| Deionized water | 75.09 | 75.06 g | 75.02 g | 75.02 g | 72.08 g | 75.09 g |
| Sieve cut [μm] | 150-850 | 150-850 | 300-850 | 300-850 | 300-850 | 425-850 |
| yield | 460.5 g | 507.7 g | 519.1 g | 352.3 g | 423.5 g | 289.2 g |

The superabsorbent polymers SAP 11-12 were made by mixing two superabsorbent polymers as follows:

The amount of the first superabsorbent polymer (agglomerated) and the amount of the second superabsorbent polymer (see table below) were placed in a wide-necked 100 ml PE bottle (e.g. from VWR, Art. No. 215-5631). The bottle is closed with the cap and then gently moved by hand in a rotation movement (e.g. clockwise) upside down and up again, avoiding vibrational movements (e.g. shaking). The rotational movement is continued for about 1 min, performing about 40-60 rotations.

| Final Code | SAP 11 | SAP 12 |
|---|---|---|
| First SAP | SAP 5 | SAP 6 |
| Amount of first SAP | 8.0 g | 8.0 g |
| Second SAP | SAP 2 | SAP 2 |
| Amount of Second SAP | 12.0 g | 12.0 g |

Properties of the SAPs Exemplified:

The properties of the SAP were measured and the results are as follows. T20 and U20 were measured with 3 replicates, except otherwise indicated (n=).

SAP 1-3 and SAP 7-12 are examples having a T20 below 240 s.

SAP 4 is a Comparative example.

SAP 7-12 contain agglomerated superabsorbent polymer particles.

| | T20 (s) | CRC (g/g) | FSR (g/g/s) | UPM ($10^{-7}$ cm$^3$ · s/g) | U20 (g/g) |
|---|---|---|---|---|---|
| SAP1 (used in Core Example 1) | 194 | 25.4 | 0.27 | 64 | 28.3 |
| SAP2 | 211 | 26.1 | 0.19 | 99 | 29.7 |
| SAP3 | 188 | 27.7 | 0.24 | 41 | 31 |

|  | T20 (s) | CRC (g/g) | FSR (g/g/s) | UPM ($10^{-7}$ cm$^3 \cdot$ s/g) | U20 (g/g) |
|---|---|---|---|---|---|
| SAP4 (used in Comparative Core Examples 1 and 2) | 341 | 26.7 | 0.15 | 55 | 27.3 |
| SAP 7 | 117 | 24.3 | 0.55 | 71 | 27.9 |
| SAP 8 | 108 (n = 4) | 23.2 | 0.55 | 90 | 25.9 (n = 4) |
| SAP 9 | 104 | 25.2 | 0.59 | 49 | 29.3 |
| SAP 10 | 199 | 29.1 | 0.29 | 58 | 30.9 |
| SAP 11 | 192 (n = 1) | 23.1 | 0.62 | 53 | 27.0 (n = 1) |
| SAP 12 | 164 (n = 2) | 24.0 | 0.61 | 47 | 28.0 (n = 2) |

SAP1 and comparative SAP4 were used in the core examples described in more details below.

Absorbent Core Examples:

Invention example 1, described in details below, is an absorbent core which illustrates the present invention. The core of example 1 comprised two channels similar to those shown in FIG. 1 and the SAP described above having a T20 of 194 s. Comparative example 1 comprised the SAP having a T20 of 341 s and no channels. Comparative example 2 comprised the same channels as example 1 and the same SAP as comparative core example 1 (SAP4).

Figure 8:
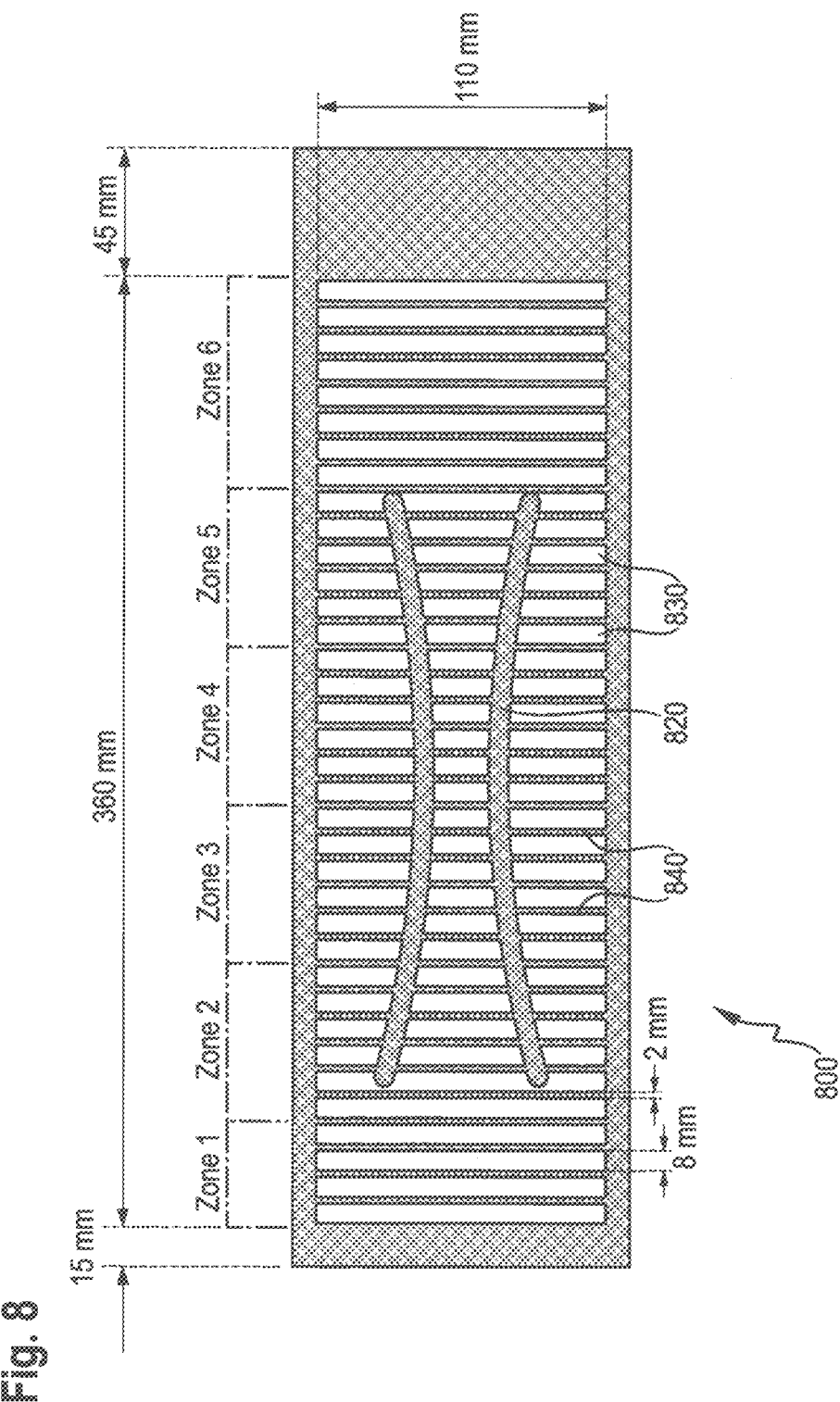
FIG. 8 is a sketch of a vacuum table which was used to make the exemplary absorbent cores 1 and 3 described below.

The core of example 1 was made by combining two absorbent layers. The first absorbent layer comprised as first substrate a 420 mm long and 165 mm wide hydrophilic nonwoven web (SMS, i.e. spunbond-meltblown-spunbond layers) made of polypropylene and having a basis weight of 10 g/m². This substrate was positioned on a vacuum table 800 as shown schematically on FIG. 8. The table comprises a rigid support comprising a series of transversal support ridges 840 and two channel shaped ridges 820. The vacuum holes 830 are formed between these ridges. The vacuum areas were each 8 mm wide (MD) and 110 mm long (CD), except in the area where the channel shaped ridges were present, the width of the transversal ridges was 2 mm (MD) for a total of 36 parallel stripes.

The nonwoven substrate was positioned on the vacuum table. A net of Microfiber glue (NW1151ZP ex. FULLER ADHESIVES) was evenly applied on the substrate at an average basis weight of about 10 g/m² and a width of 110 mm, covering the whole length of the substrate. The vacuum pattern was divided in 6 zones starting from the 1$^{st}$ stripe. Area 1 was 40 mm long in MD. Zones 2 to 5 are 60 mm wide and zone 6 was 80 mm wide. With vacuum helping immobilizing the SAP in the desired regions, the SAP was homogeneously distributed within each zone according to the below table. The pre-determined amount of SAP was distributed for each zone with the aid of shaped silicon paper matching exactly the vacuum table design.

| Zone | 1 | 2 | 3 | 4 | 5 | 6 | Total |
|---|---|---|---|---|---|---|---|
| Length (mm) | 40 | 60 | 60 | 60 | 60 | 80 | 360 |
| SAP amount (g) | 0.81 | 1.37 | 1.71 | 1.58 | 0.97 | 0.61 | 7.05 |

As a result, the SAP was applied in stripes matching the pattern of the vacuum table. The overall amount of superabsorbent polymer material in the first absorbent layer was 7.05 g. Subsequent to the application of the SAP, a net of Microfiber glue (first adhesive) was evenly applied, at an average basis weight of about 10 g/m² and a width of 110 mm, covering the whole length of the first absorbent layer. The two curved SAP free materials area were further fitted with a double side adhesive (1524-3M transfer adhesive with a width 6.4 mm) along the channel area on the nonwoven. This was to ensure sufficient bond strength of the channels during the further testing of these hand-made absorbent cores. In an industrial process, the pressure and the adhesive used as auxiliary glue is normally sufficient to ensure a strong bond without the need of a double sided tape.

The second absorbent layer comprised as second substrate a 420 mm long and 130 mm wide SMS nonwoven web made of polypropylene and having a basis weight of 10 g/m². The second absorbent layer was formed using a similar vacuum table and absorbent material and glue as the first absorbent layer, with the transversal ridges shifted by a few mm so that the land and junction areas of the opposed absorbent layer match each other.

The first and the second absorbent layers were combined by placing them together such that the sides of both carrier substrates, which were not covered by superabsorbent polymer material were facing outwardly. Thereby the laminate absorbent core is formed with the superabsorbent polymer material enclosed between the first and second carrier substrate. The first and second absorbent layers were combined such that each SAP stripe was placed to match the gap between the stripes of the absorbent layer directly opposed. Hence, each SAP stripe of the upper layer is placed centrally in the respective gap between two superabsorbent polymer material stripes of the lower laminate layer and vice versa in order to provide a substantially continuous combined absorbent layer.

After the two absorbent layers are combined, the external edges of the first substrate were folded over the second substrate so that the combined core structure had a width of 120 mm. In these hand-made samples, the flaps on each side were fixed with a stripe of double side adhesive (1524-3M transfer adhesive with a width 6.4 mm) of 420 mm, but in an industrial process a standard hotmelt glue can be used to seal the longitudinal sides of the core.

Comparative Example 1

Comparative example 1 was made as example 1 with the differences that the vacuum table did not comprise channel forming ridges and that the SAP4 having a T20 of 341 s was used. Thus this absorbent core did not form channels when absorbing a liquid. The same amount of SAP and their repartition in the zones was used.

Comparative Example 2

Comparative example 2 was made as example 1 using the same vacuum table to form the same areas free of SAP as Invention Example 1. The SAP used for this absorbent core was the same SAP4 as in Comparative Example 1 having a T20 of 341 s.

Test Results

The Speed of Absorption Test described above was conducted on five samples. The results were averaged and are reported in the Table below.

|  | Speed g/s @ 90 s | Speed g/s @ 180 s |
|---|---|---|
| Comparative Example 1 (without channels) | 1.74 | 1.55 |

|  | Speed g/s @ 90 s | Speed g/s 180 @ s |
| --- | --- | --- |
| Comparative Example 2 (with channels) | 1.73 | 1.50 |
| Invention Example 1 | 2.26 | 1.79 |

Comparative examples 1 and 2 show that for the first 90 s of the test, the presence or absence of the channels did not significantly influence the speed of absorption. At 180 s however, the speed of acquisition of the core with the channels was significantly worse (minus 0.05 g/s) than the same core without the channels (at 95% confidence with t-Student test). The core of the invention example 1 showed an acquisition speed at 180 s of 1.79 g/s, which was significantly higher than the speed of the conventional AGM at 180 s or even at 90 s.

MISC

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for personal hygiene comprising:
a liquid permeable topsheet;
a liquid impermeable backsheet;
an absorbent core disposed between the topsheet and the backsheet; and
an acquisition/distribution layer disposed between the absorbent core and the topsheet;
wherein the absorbent core comprises:
a core wrap enclosing an absorbent material comprising a combination of superabsorbent polymer particles and airfelt, the core wrap comprising a top side and a bottom side;
one or more pairs of areas substantially free of absorbent material through which the top side of the core wrap is attached to the bottom side of the core wrap, so that when the absorbent material swells the core wrap forms one or more pairs of channels along the areas substantially free of absorbent material;
wherein at least one pair of the one or more pairs of areas substantially free of absorbent material is arranged symmetrically relative to a longitudinal axis;
wherein the superabsorbent polymer particles have a time to reach an uptake of 20 g/g (T20) of less than 240s, as measured according to a K(t) test method; and
wherein the attachment between the top side core wrap and the bottom side core wrap is achieved through adhesive bonding, pressure bonding, ultrasonic bonding, heat bonding, or combinations thereof.

2. The absorbent article of claim 1, wherein the top side of the core wrap is continuously attached to the bottom side of the core wrap.

3. The absorbent article of claim 1, wherein the top side of the core wrap is discontinuously attached to the bottom side of the core wrap.

4. The absorbent article of claim 3, wherein the top side of the core wrap is discontinuously attached to the bottom side of the core wrap with a series of point bonds.

5. The absorbent article of claim 1, wherein the superabsorbent polymer particles have a time to reach an uptake of 20 g/g (T20) of from about 40s to less than about 240s.

6. The absorbent article of claim 1, wherein the superabsorbent polymer particles comprise agglomerated superabsorbent polymer particles.

7. The absorbent article of claim 1, wherein the absorbent core comprises from about 2 g to about 50 g of superabsorbent polymer particles.

8. The absorbent article of claim 7, wherein the absorbent core comprises from about 5 g to about 40 g of superabsorbent polymer particles.

9. The absorbent article of claim 1, wherein at least one of the one or more pairs of areas substantially free of absorbent material has a length (L') projected on the longitudinal axis of the core which is at least 10% of the length (L") of the absorbent core.

10. The absorbent article of claim 1, wherein at least one of the one or more pairs of areas substantially free of absorbent material has a width (W c) at least in some part of the area substantially free of absorbent material of at least about 2 mm.

11. The absorbent article of claim 1, wherein the superabsorbent polymer particles have an UPM value of from about 40.10-7 cm3·s/g to about 500.10-7 cm3·s/g and/or the superabsorbent polymer particles have a CRC value of from about 18 g/g to about 40 g/g.

12. The absorbent article of claim 1, comprising an auxiliary glue between the absorbent material and the top side and/or the bottom side of the core wrap.

13. The absorbent article of claim 1, wherein the absorbent core has a caliper measured at the core's crotch point (C') of from about 0.2 to about 4 mm.

14. The absorbent article of claim 1, wherein the at least one pair of areas substantially free of absorbent material are curved such that a region of each area of the pair of areas substantially free of absorbent material disposed in a crotch region of the absorbent article is concave toward the longitudinal axis.

15. An absorbent article for personal hygiene comprising:
a liquid permeable topsheet;
a liquid impermeable backsheet;
an absorbent core disposed between the topsheet and the backsheet; and
an acquisition/distribution layer disposed between the absorbent core and the topsheet;

wherein the absorbent core comprises:
- a core wrap enclosing an absorbent material comprising a combination of superabsorbent polymer particles and airfelt, the core wrap comprising a top side and a bottom side;
- a pair of areas substantially free of absorbent material disposed symmetrically relative to a longitudinal axis through which the top side of the core wrap is attached to the bottom side of the core wrap, so that when the absorbent material swells the core wrap forms a pair of channels along the areas substantially free of absorbent material and corresponding ditches;
- wherein the superabsorbent polymer particles have a time to reach an uptake of 20 g/g (T20) of less than 240 s, as measured according to the K(t) test method; and
- wherein the attachment between the top side core wrap and the bottom side core wrap is achieved through adhesive bonding, pressure bonding, ultrasonic bonding, heat bonding, or combinations thereof.

16. The absorbent article of claim 15, wherein the top side of the core wrap is attached to the bottom side of the core wrap continuously along the pair of areas substantially free of absorbent material.

17. The absorbent article of claim 15, wherein the top side of the core wrap is attached to the bottom side of the core wrap discontinuously along the pair of areas substantially free of absorbent material.

18. The absorbent article of claim 15, wherein the top side of the core wrap is attached to the bottom side of the core wrap with a series of point bonds.

19. The absorbent article of claim 15, wherein the core wrap comprises a first nonwoven substantially forming the top side of the core wrap and a second nonwoven substantially forming the bottom side of the core wrap.

20. The absorbent article of claim 15, wherein the pair of areas substantially free of absorbent material are curved such that a region of each area of the pair of areas substantially free of absorbent material disposed in a crotch region of the absorbent article is concave toward the longitudinal axis.

* * * * *